United States Patent
Murakami et al.

(10) Patent No.: US 11,147,464 B2
(45) Date of Patent: Oct. 19, 2021

(54) PULSE WAVE MEASURING APPARATUS AND PULSE WAVE MEASURING METHOD

(71) Applicant: Panasonic Intellectual Property Management Co., Ltd., Osaka (JP)

(72) Inventors: Kenta Murakami, Osaka (JP); Jun Ozawa, Nara (JP); Mototaka Yoshioka, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 777 days.

(21) Appl. No.: 15/725,162

(22) Filed: Oct. 4, 2017

(65) Prior Publication Data

US 2018/0110428 A1 Apr. 26, 2018

(30) Foreign Application Priority Data

Oct. 20, 2016 (JP) .............................. JP2016-205859
Jun. 23, 2017 (JP) .............................. JP2017-122794

(51) Int. Cl.
*A61B 5/024* (2006.01)
*A61B 5/02* (2006.01)
(Continued)

(52) U.S. Cl.
CPC ............ *A61B 5/02433* (2013.01); *A61B 5/02* (2013.01); *A61B 5/0261* (2013.01); *A61B 5/18* (2013.01);
(Continued)

(58) Field of Classification Search
CPC ...... A61B 5/02433; A61B 5/0261; A61B 5/18; A61B 5/6893; A61B 5/7246;
(Continued)

(56) References Cited

U.S. PATENT DOCUMENTS 6,400,835 B1 * 6/2002 Lemelson ............ B60Q 1/0023
382/118
7,199,767 B2 * 4/2007 Spero ........................ G02B 5/20
345/7
(Continued)

FOREIGN PATENT DOCUMENTS

JP 2006-248365 9/2006
JP 2007-249477 9/2007
(Continued)

OTHER PUBLICATIONS

Machine translation of JP2006248365 (Year: 2006).*
(Continued)

*Primary Examiner* — Carolyn A Pehlke
(74) *Attorney, Agent, or Firm* — Wenderoth, Lind & Ponack, L.L.P.

(57) ABSTRACT

A pulse wave measuring apparatus includes a visible light receiver having a first surface and a pulse wave calculator. When a vehicle with the visible light receiver is viewed from a side, the first surface is in a first region between a first optical path of first reflection light and a second optical path of second reflection light, first light comes from an eye of a user on a seat of the vehicle, second light comes from a cheek of the user, an upper end of a rearview mirror of the vehicle reflects the first light to produce the first reflection light and reflects the second light to produce the second
(Continued)

reflection light, and the pulse wave calculator calculates a pulse wave of the user on the basis of a waveform of visible light received by the visible light receiver via the first surface and outputs the calculated pulse wave.

4 Claims, 31 Drawing Sheets

(51) Int. Cl.
*A61B 5/18* (2006.01)
*A61B 5/026* (2006.01)
*G06K 9/00* (2006.01)
*A61B 5/00* (2006.01)

(52) U.S. Cl.
CPC .......... *A61B 5/6893* (2013.01); *A61B 5/7246* (2013.01); *A61B 5/7278* (2013.01); *G06K 9/00838* (2013.01); *A61B 2503/22* (2013.01)

(58) Field of Classification Search
CPC .............. A61B 5/7278; A61B 2503/22; G06K 9/00838; G06K 9/00832; G06K 9/00845; G06K 9/2036; G06K 9/20; G06K 9/2027; G06K 9/2054; G06K 9/00221; G06K 9/00228; G06K 9/00255; G06K 9/00362
See application file for complete search history.

(56) References Cited

U.S. PATENT DOCUMENTS

| | | | |
|---|---|---|---|
| 2011/0313259 A1* | 12/2011 | Hatakeyama | B60K 28/06 600/300 |
| 2014/0276090 A1* | 9/2014 | Breed | A61B 5/14546 600/473 |
| 2015/0363986 A1* | 12/2015 | Hoyos | H04W 4/40 340/5.61 |

FOREIGN PATENT DOCUMENTS

| | | |
|---|---|---|
| JP | 2010-125882 | 6/2010 |
| JP | 2011-019973 | 2/2011 |
| JP | 2014-198201 | 10/2014 |

OTHER PUBLICATIONS

Machine translation of JP2010125882 (Year: 2010).*
Reflection and the Ray Model of Light—Lesson 1—Reflection and its Importance, https://www.physicsclassroom.com/class/refln/Lesson-1/Specular-vs-Diffuse-Reflection, retrieved Aug. 13, 2020).*
English Translation of Chinese Search Report dated May 25, 2021 for related Chinese Patent Application No. 201710820357.8.
Yutao Ba et al., "The effect of communicational signals on drivers' subjective appraisal and visual attention during interactive driving scenarios", Behaviour & Information Technology, vol. 34 Issue 11, pp. 1107-1118, 2015.
Gao Zhenhua, "Mysterious Fatigue Monitoring", Automotive Observer, pp. 112-113, Aug. 31, 2014 with English translation.

* cited by examiner

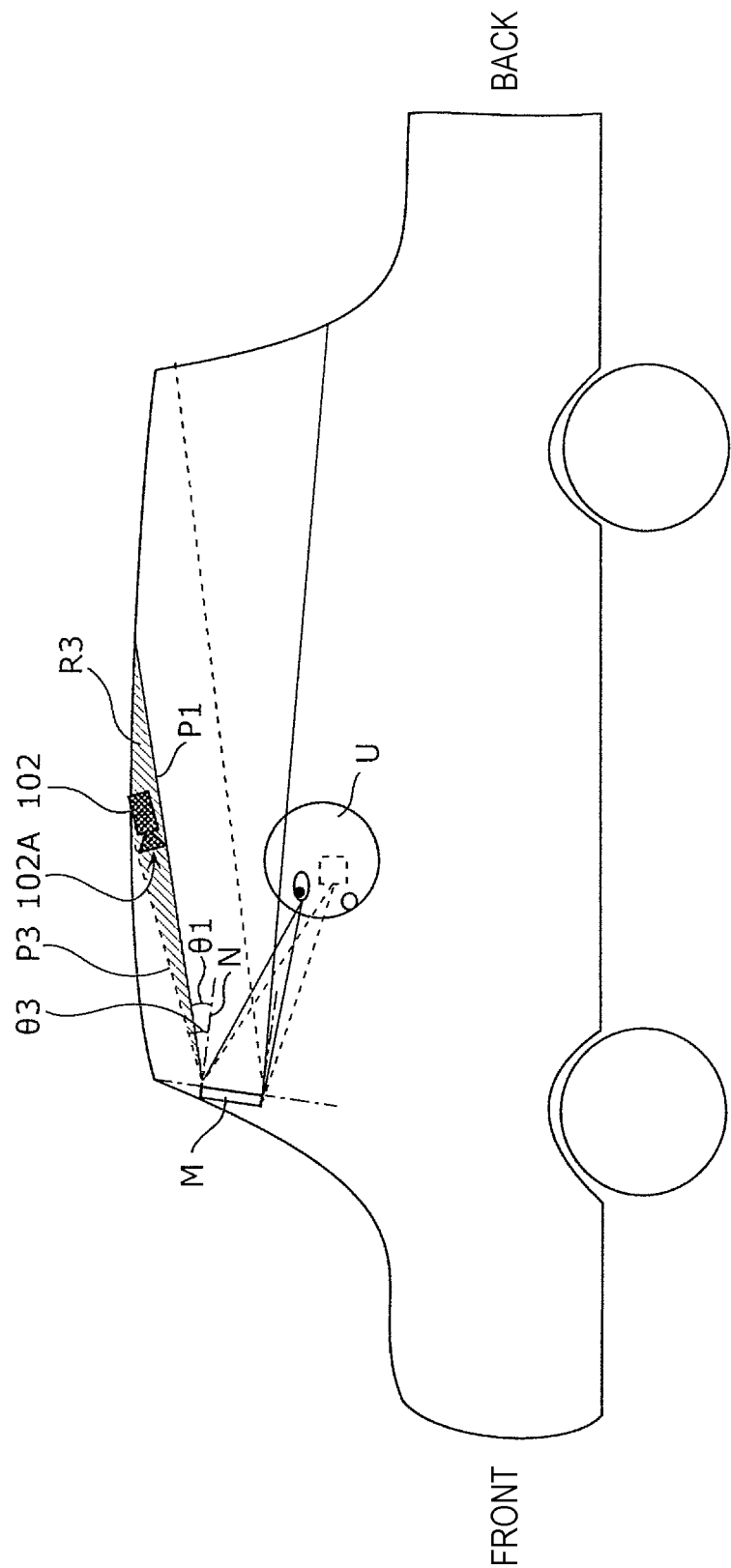

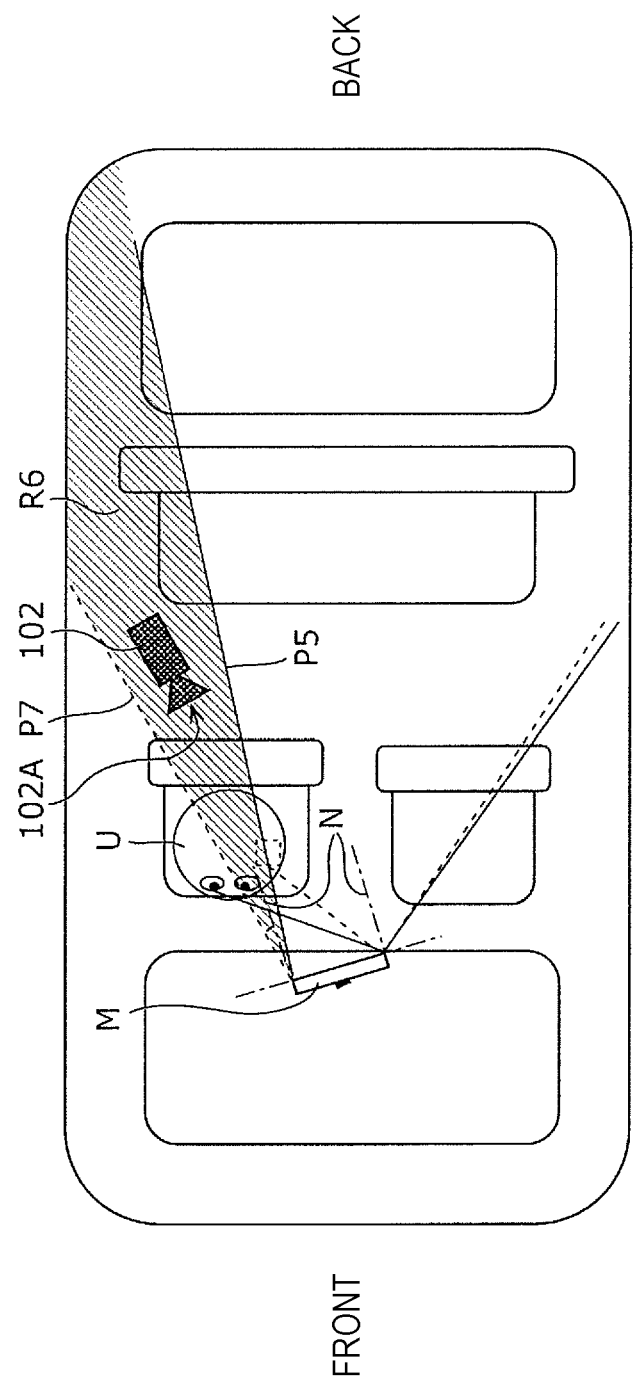

PULSE WAVE MEASURING APPARATUS AND PULSE WAVE MEASURING METHOD

BACKGROUND

1. Technical Field

The present disclosure relates to pulse wave measuring apparatuses and pulse wave measuring methods.

2. Description of the Related Art

Japanese Unexamined Patent Application Publication No. 2006-248365 discloses a technique for capturing an infrared image of the vicinity of the eyes of a user by using superposed two mirrors as a rearview mirror in an automobile. In this technique, the mirror that is closer to the user reflects visible light and transmits infrared light, and the mirror that is farther from the user reflects infrared light; thus, an infrared image of the vicinity of the eyes of the user is captured. This configuration keeps the user from visually recognizing a camera via the mirrors.

However, in the existing technique disclosed in Japanese Unexamined Patent Application Publication No. 2006-248365, two mirrors are used in order to capture an image centered on the eyes of the user. The configuration in which the two mirrors are used is complicated and leads to an increase in the cost.

SUMMARY

One non-limiting and exemplary embodiment provides a pulse wave measuring apparatus that measures a pulse wave by capturing an image of a user with a simpler configuration.

In one general aspect, the techniques disclosed here feature a pulse wave measuring apparatus that includes a visible light receiver having a first surface, and a pulse wave calculator. When a vehicle provided with the visible light receiver is viewed from a side, the first surface is located in a first region between a first optical path of first reflection light and a second optical path of second reflection light, first light comes from an eye of a user sitting on a seat of the vehicle, second light comes from a cheek of the user, an upper end of an interior front mirror of the vehicle reflects the first light to produce the first reflection light, the upper end reflects the second light to produce the second reflection light, and the pulse wave calculator calculates a pulse wave of the user on the basis of a waveform of visible light received by the visible light receiver via the first surface and outputs the calculated pulse wave.

According to the present disclosure, the pulse wave can be measured by capturing an image of the user with a simpler configuration.

It is to be noted that general or specific embodiments of the above may be implemented in the form of a system, a method, an integrated circuit, a computer program, or a computer-readable recording medium, or through any desired combination of an apparatus, a system, a method, an integrated circuit, a computer program, and a recording medium. Examples of the computer-readable storage medium include a nonvolatile storage medium, such as a Compact Disc-Read Only Memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 6A is a descriptive diagram, as the vehicle is viewed from a side, illustrating a region in which a visible light imaging unit can be installed and in which the visible light imaging unit can capture an image of a cheek of a user via a rearview mirror and is not visually recognized by the user according to an embodiment;

FIG. 9A is a diagram, as the vehicle is viewed from the above, illustrating a region in which a visible light imaging unit can be installed according to an embodiment;

DETAILED DESCRIPTION

Figure 1:
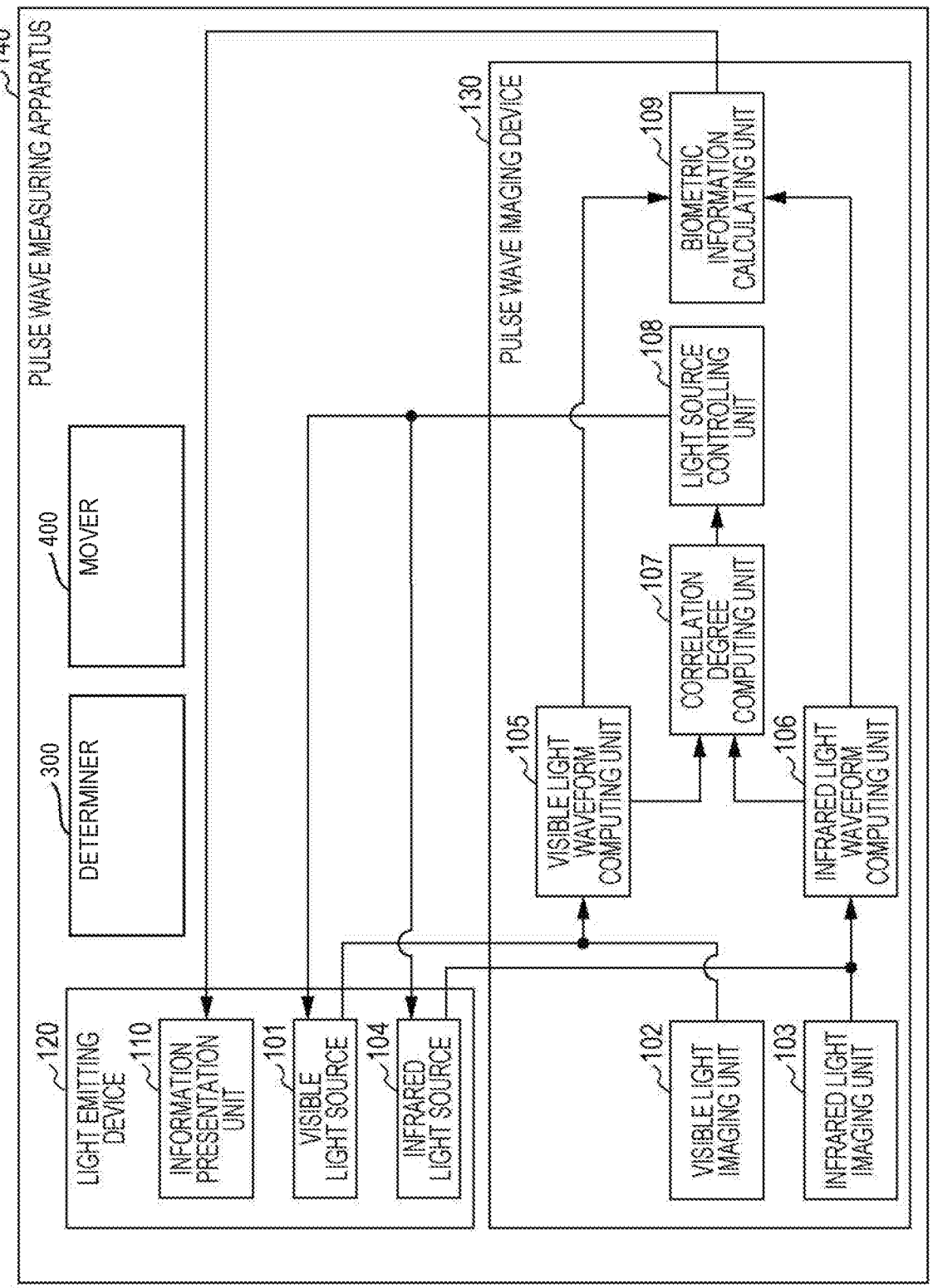
FIG. 1 is a block diagram illustrating a configuration of a pulse wave measuring apparatus according to an embodiment.

To address the problem described above, a pulse wave measuring apparatus according to an aspect of the present disclosure includes a visible light receiver that is provided in a region including a region in an optical path of light coming from a user and reflected by a rearview mirror of a vehicle and excluding a region that the user can see via the rearview mirror, and a pulse wave calculator that calculates a pulse wave of the user on the basis of a waveform of visible light received by the visible light receiver and outputs the calculated pulse wave.

With this configuration, the visible light receiver can acquire an image of the user via the rearview mirror, and the user does not visually recognize the visible light receiver. Thus, the user can drive without being distracted by a camera constituted by the visible light receiver, and the pulse wave measuring apparatus can acquire the pulse wave of the user while driving. Here, the rearview mirror is adjusted by the user typically for driving (specifically, in order to ensure the rearward field of view or the like). Thus, the user does not need to adjust the attitude of the rearview mirror in order to acquire the pulse wave. In addition, the rearview mirror is a typical rearview mirror mounted in a vehicle and is not a rearview mirror providing any special performance or function exceeding that of a typical rearview mirror. In this manner, the pulse wave measuring apparatus can measure the pulse wave by capturing an image of the user with a simpler configuration.

For example, the pulse wave measuring apparatus further includes an infrared light receiver that is provided in a region including a region in an optical path of light coming from the user and reflected by the rearview mirror and excluding a region that the user can see via the rearview mirror, and the pulse wave calculator calculates the pulse wave on the basis of a waveform of visible light received by the visible light receiver and a waveform of infrared light received by the infrared light receiver.

According to the above aspect, in a similar manner to the visible light receiver, the infrared light receiver can acquire an image of the user via the rearview mirror, and the user does not visually recognize the infrared light receiver. Thus, the user can drive without being distracted by a camera constituted by the infrared light imaging unit, and the pulse wave measuring apparatus can acquire the pulse wave of the user while driving.

In addition, a pulse wave measuring apparatus according to an aspect of the present disclosure includes a visible light receiver having a first surface, and a pulse wave calculator. When a vehicle provided with the visible light receiver is viewed from a side, the first surface is located in a first region between a first optical path of first reflection light and a second optical path of second reflection light, first light comes from an eye of a user sitting on a seat of the vehicle, second light comes from a cheek of the user, an upper end of an interior front mirror of the vehicle reflects the first light to produce the first reflection light, the upper end reflects the second light to produce the second reflection light, and the pulse wave calculator calculates a pulse wave of the user on the basis of a waveform of visible light received by the visible light receiver via the first surface and outputs the calculated pulse wave.

According to the above aspect, the feature that the visible light receiver can acquire an image of a cheek of the user via a rearview mirror and the user does not visually recognize the visible light receiver is achieved specifically by the installation position of the visible light receiver as the vehicle is viewed from a side.

For example, the pulse wave measuring apparatus further includes an infrared light receiver having a second surface located in the first region, and the pulse wave calculator calculates the pulse wave on the basis of further a waveform of infrared light received by the infrared light receiver via the second surface.

According to the above aspect, the feature that the infrared light receiver can acquire an image of a cheek of the user via a rearview mirror and the user does not visually recognize the infrared light receiver is achieved specifically by the installation position of the infrared light receiver as the vehicle is viewed from a side.

In addition, a pulse wave measuring apparatus according to an aspect of the present disclosure includes a visible light receiver having a first surface, and a pulse wave calculator. When (a) a vehicle with a right-hand steering wheel provided with the visible light receiver is viewed from the above, the first surface is located in a first region between a first optical path of first reflection light and a second optical path of second reflection light, first light comes from a left eye of a user sitting on a seat closest to the right-hand steering wheel of the vehicle, second light comes from a left cheek of the user, a right end of an interior front mirror of the vehicle reflects the first light to produce the first reflection light, the right end reflects the second light to produce the second reflection light, and the right end is closer to the right-hand steering wheel than a left end of the interior front mirror of the vehicle is; or when (b) a vehicle with a left-hand steering wheel provided with the visible light receiver is viewed from the above, the first surface is located in a second region between a third optical path of third reflection light and a fourth optical path of fourth reflection light, third light comes from a right eye of the user sitting on a seat closest to the left-hand steering wheel of the vehicle, fourth light comes from a right cheek of the user, the left end reflects the third light to produce the third reflection light, the left end reflects the fourth light to produce the fourth reflection light, the left end is closer to the left-hand steering wheel than the right end is; and the pulse wave calculator calculates a pulse wave of the user on the basis of a waveform of visible light received by the visible light receiver via the first surface and outputs the calculated pulse wave.

According to the above aspect, the feature that the visible light receiver can acquire an image of a cheek of the user via a rearview mirror and the user does not visually recognize the visible light receiver is achieved specifically by the installation position of the visible light receiver as the vehicle is viewed from the above.

For example, the pulse wave measuring apparatus further includes an infrared light receiver having a second surface located in the first region, and the pulse wave calculator calculates the pulse wave on the basis of further a waveform of infrared light received by the infrared light receiver via the second surface.

According to the above aspect, the feature that the infrared light receiver can acquire an image of a cheek of the user via a rearview mirror and the user does not visually recognize the infrared light receiver is achieved specifically by the installation position of the infrared light receiver as the vehicle is viewed from the above.

For example, the pulse wave measuring apparatus further includes an infrared light source disposed at a position closer to the center of the vehicle in the right and left direction than to a seat on which the user sits.

According to the above aspect, the pulse wave measuring apparatus can irradiate, of the face of the user, a region suitable for measuring the pulse wave of the user with irradiation light (infrared light) for capturing an image of the user with infrared light by the infrared light receiver. The region suitable for measuring the pulse wave of the user is a region that includes, for example, a cheek within the face of the user. In addition, typically, a controller or the like for a car navigation device or for an air conditioner is disposed at the center of the vehicle in the right and left direction. Thus, there is an advantage in that it is relatively easy to add the infrared light source to such devices or to dispose the infrared light source in the vicinity of such devices. Another reason is that the signal wires and the electric power wires of the vehicle are integrated.

For example, the position of the first surface is a position that is above the first optical path and that is to the front of the vehicle by a first distance, as the vehicle is viewed from a side.

According to the above aspect, the feature that the visible light receiver can acquire an image of a cheek of the user via a rearview mirror and the user does not visually recognize the visible light receiver can be achieved specifically. In particular, the position in an optical path of light coming from an eye of the user and reflected by the upper end portion of the rearview mirror is the position on which the user can place a mark by checking the rearview mirror. Thus, there is an advantageous effect that the user can determine the position of the visible light receiver with ease.

For example, the pulse wave measuring apparatus further includes a determiner that determines whether the user wears eyeglasses through image processing, and a mover that moves the first surface to a position that is above the first optical path and that is to the front of the vehicle by a second distance greater than the first distance, as the vehicle is viewed from a side, in a case in which the determiner has determined that the user wears the eyeglasses.

According to the above aspect, even in a case in which the user wears eyeglasses, the pulse wave of the user can be measured appropriately. When the user wears eyeglasses, the frame of the eyeglasses may overlap the cheeks in an image for measuring the pulse wave, and the stated configuration is for preventing such an overlap.

In addition, a pulse wave measuring method according to an aspect of the present disclosure includes (a) receiving, with a visible light receiver having a first surface, visible light via the first surface, wherein when a vehicle provided with the visible light receiver is viewed from a side, the first surface is located in a first region between a first optical path of first reflection light and a second optical path of second reflection light, first light comes from an eye of a user sitting on a seat of the vehicle, second light comes from a cheek of the user, an upper end of an interior front mirror of the vehicle reflects the first light to produce the first reflection light, and the upper end reflects the second light to produce the second reflection light; and (b) calculating, with a pulse wave calculator, a pulse wave of the user on the basis of a waveform of the received visible light and outputting the calculated pulse wave.

According to the above, an advantageous effect similar to that of the pulse wave measuring apparatus described above is obtained.

In addition, a pulse wave measuring method according to an aspect of the present disclosure includes (a) receiving, with a visible light receiver having a first surface, visible light via the first surface, wherein (a-1) when a vehicle with a right-hand steering wheel provided with the visible light receiver is viewed from the above, the first surface is located in a first region between a first optical path of first reflection light and a second optical path of second reflection light, first light comes from a left eye of a user sitting on a seat closest to the right-hand steering wheel of the vehicle, second light comes from a left cheek of the user, a right end of an interior front mirror of the vehicle reflects the first light to produce the first reflection light, the right end reflects the second light to produce the second reflection light, and the right end is closer to the right-hand steering wheel than a left end of the interior front mirror of the vehicle is, or (a-2) when a vehicle with a left-hand steering wheel provided with the visible light receiver is viewed from the above, the first surface is located in a second region between a third optical path of third reflection light and a fourth optical path of fourth reflection light, third light comes from a right eye of a user sitting on a seat closest to the left-hand steering wheel of the vehicle, fourth light comes from a right cheek of the user, the left end reflects the third light to produce the third reflection light, the left end reflects the fourth light to produce the fourth reflection light, and the left end is closer to the left-hand steering wheel than the right end is; and (b) calculating, with a pulse wave calculator, a pulse wave of the user on the basis of a waveform of the visible light received via the first surface and outputting the calculated pulse wave.

According to the above, an advantageous effect similar to that of the pulse wave measuring apparatus described above is obtained.

It is to be noted that general or specific embodiments of the above may be implemented in the form of a system, a method, an integrated circuit, a computer program, or a computer-readable recording medium, such as a CD-ROM, or through any desired combination of a system, a method, an integrated circuit, a computer program, and a recording medium.

Hereinafter, embodiments will be described in concrete terms with reference to the drawings.

It is to be noted that the embodiments described hereinafter merely illustrate general or specific examples. The numerical values, the shapes, the materials, the constituent elements, the arrangement and the positions of the constituent elements, the connection modes of the constituent elements, the steps, the order of the steps, and so forth illustrated in the embodiments hereinafter are examples and are not intended to limit the present disclosure. In addition, among the constituent elements described in the embodiments hereinafter, a constituent element that is not described in an independent claim indicating the broadest concept is described as an optional constituent element.

Embodiments

In the present embodiment, a pulse wave measuring apparatus that measures a pulse wave by capturing an image of a user with a simple configuration and a pulse wave measuring method (in other words, a method of controlling the pulse wave measuring apparatus) will be described. Specifically, the pulse wave measuring apparatus according to the present embodiment contactlessly acquires the pulse wave of a user in a visible light range and an infrared light range by using a rearview mirror installed in a vehicle. The pulse wave measuring apparatus may be implemented as a pulse wave measuring system constituted by a plurality of apparatuses.

In the present embodiment, the premise is that the attitude of the rearview mirror is adjusted by the driver (the user) of the vehicle. This adjustment is typically performed by the driver in order to ensure the field of view behind the vehicle and is not performed for the purpose of using the pulse wave measuring apparatus illustrated in the present embodiment.

Figure 2:
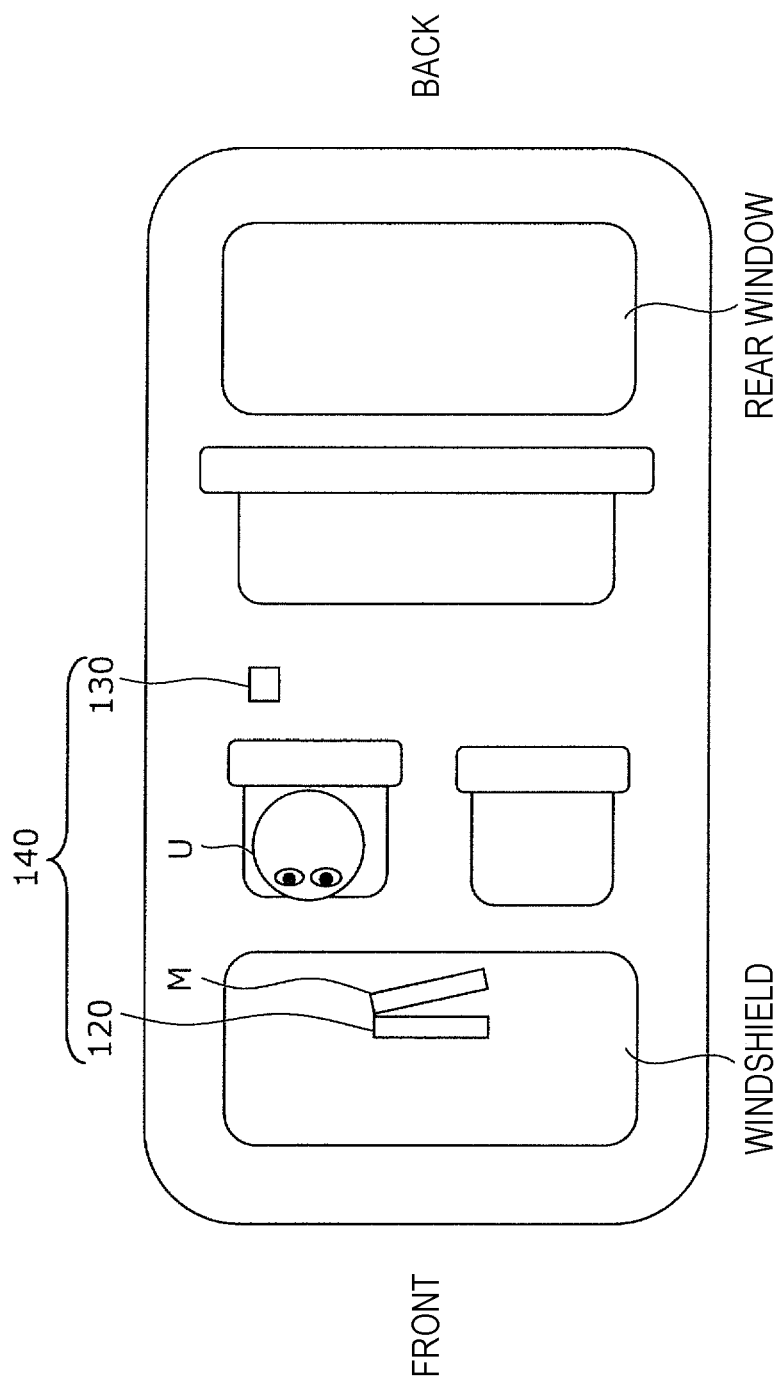
FIG. 2 is a schematic diagram, as viewed from the above, of the interior of a vehicle in which a pulse wave measuring apparatus according to an embodiment is disposed.
Figure 3:
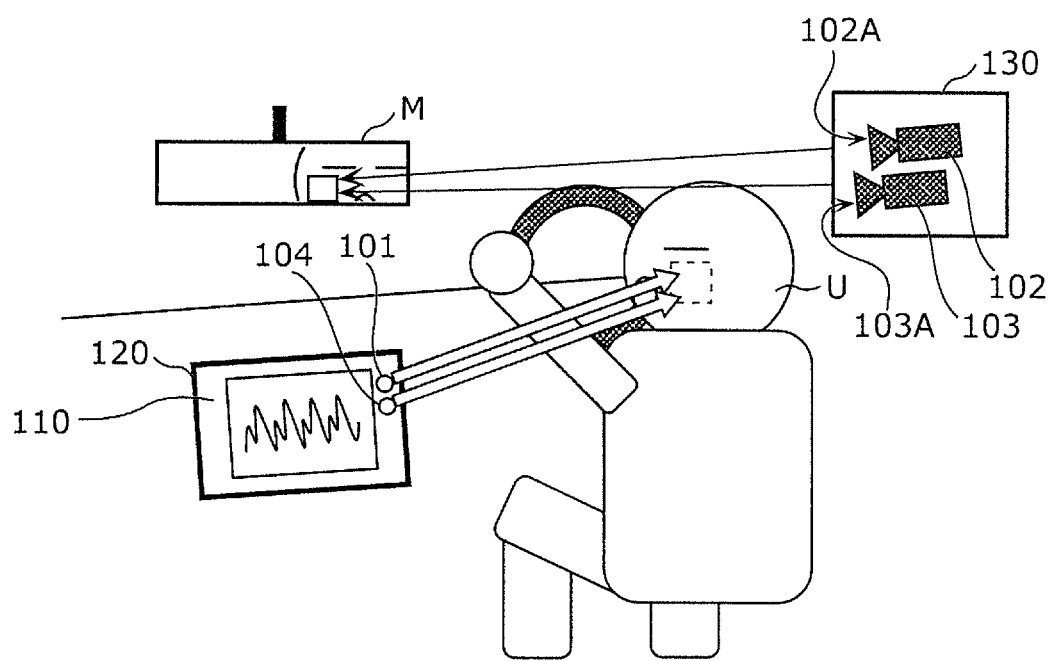
FIG. 3 is a descriptive diagram illustrating a situation in which the pulse wave of a user is measured with a pulse wave measuring apparatus according to an embodiment.
Figure 4:
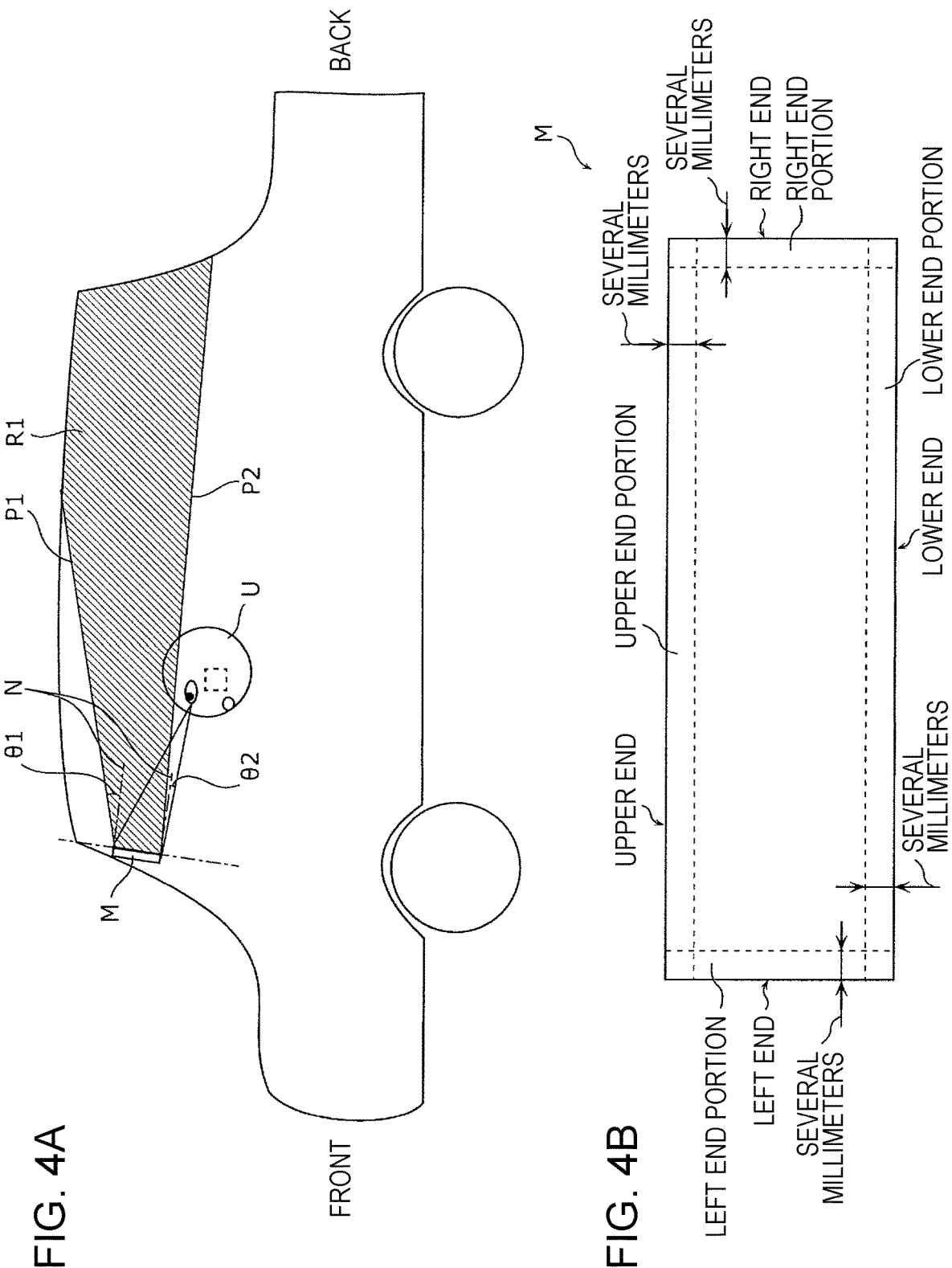
FIG. 4A is a descriptive diagram, as the vehicle is viewed from a side, illustrating a region that a user can visually recognize via a rearview mirror according to an embodiment.
FIG. 4B is a descriptive diagram of an upper end portion, a lower end portion, a left end portion, and a right end portion of a rearview mirror according to an embodiment.

A pulse wave measuring apparatus 140 according to the present embodiment will be described. FIG. 1 is a block diagram illustrating a configuration of the pulse wave measuring apparatus 140 according to the present embodiment. FIG. 2 and FIG. 3 are schematic diagrams illustrating a situation in which the pulse wave measuring apparatus 140 according to the present embodiment is used by a user.

As illustrated in FIG. 1, the pulse wave measuring apparatus 140 includes a visible light source 101, a visible light imaging unit 102, an infrared light imaging unit 103, an infrared light source 104, a visible light waveform computing unit 105, an infrared light waveform computing unit 106, a correlation degree computing unit 107, a light source controlling unit 108, a biometric information calculating unit 109, and an information presentation unit 110.

The visible light source 101 emits visible light and irradiates the skin (the body surface) of the user with the visible light.

The visible light imaging unit 102 captures an image of the skin of the user in a visible light range. The visible light imaging unit 102 corresponds to a visible light receiver. A portion of the surface of the visible light imaging unit 102 corresponds to a first surface of the visible light receiver. The visible light imaging unit 102 takes in the visible light through this portion of the surface.

The infrared light imaging unit 103 captures an image of the skin of the user in an infrared light range. The infrared light imaging unit 103 corresponds to an infrared light receiver. A portion of the surface of the infrared light imaging unit 103 corresponds to a second surface of the infrared light receiver. The infrared light imaging unit 103 takes in the infrared light through this portion of the surface.

The infrared light source 104 irradiates the skin of the user with infrared light.

The visible light waveform computing unit 105 extracts a waveform of a pulse wave from an image captured by the visible light imaging unit 102 with visible light.

The infrared light waveform computing unit 106 extracts a waveform of a pulse wave from an image captured by the infrared light imaging unit 103 with infrared light.

The correlation degree computing unit 107 compares the waveform of the pulse wave obtained with visible light (hereinafter, also referred to as a visible light pulse wave) with the waveform of the pulse wave obtained with infrared light (hereinafter, also referred to as an infrared light pulse wave) and computes the degree of correlation therebetween.

The light source controlling unit 108 controls the visible light source 101 and the infrared light source 104 on the basis of the waveform extracted from the visible light received by the visible light imaging unit 102 and the waveform extracted from the infrared light received by the infrared light imaging unit 103.

The biometric information calculating unit 109 calculates pulse wave information that indicates the pulse wave of the user from the visible light pulse wave and the infrared light pulse wave.

The information presentation unit 110 presents the pulse wave information calculated by the biometric information calculating unit 109.

The configuration may also be as follows. Specifically, the pulse wave measuring apparatus 140 includes a light emitting device 120 and a pulse wave imaging device 130; the light emitting device 120 includes the visible light source 101, the infrared light source 104, and the information presentation unit 110 that are described above; and the pulse wave imaging device 130 includes the visible light imaging unit 102, the infrared light imaging unit 103, the visible light waveform computing unit 105, the infrared light waveform computing unit 106, the correlation degree computing unit 107, the light source controlling unit 108, and the biometric information calculating unit 109 that are described above. Hereinafter, this configuration will be described.

These functional block diagrams illustrated in FIG. 1 will be described later in detail.

FIG. 2 and FIG. 3 illustrate an example of a method of installing the pulse wave measuring apparatus 140 inside a vehicle. FIG. 2 is a schematic diagram, as viewed from the above, of the interior of the vehicle in which the pulse wave measuring apparatus 140 is disposed. FIG. 3 is a descriptive diagram illustrating a situation in which the pulse wave of a user U is measured with the pulse wave measuring apparatus 140 according to the present embodiment.

The direction in which the vehicle travels may be referred to as "front" or "forward," and the direction opposite to the direction in which the vehicle travels may be referred to as "back" or "rearward." In addition, the left, the right, and the right and left direction as viewed from the driver of the vehicle may be referred as the left, the right, and the right and left direction, respectively, and the upper side, the lower side, and the up and down direction as viewed from the driver of the vehicle may be referred to simply as the upper side, the lower side, and the up and down direction, respectively.

As illustrated in FIG. 2, the light emitting device 120 and the pulse wave imaging device 130 included in the pulse wave measuring apparatus 140 are disposed inside the vehicle.

As described above, the light emitting device 120 includes the visible light source 101, the infrared light source 104, and the information presentation unit 110. In particular, the visible light source 101 and the infrared light source 104 may be embedded, for example, in an edge (bezel) portion of a display screen of a car navigation device or the like. The information presentation unit 110 does not need to be included inside the light emitting device 120. In that case, a display screen of a mobile terminal, such as a smartphone, communicably connected to the light emitting device 120 may be used as the information presentation unit 110. In addition, the visible light source 101 may, for example, be a display screen of a car navigation device that emits visible light. In that case, the luminance of the display screen of the car navigation device may be modified as desired in order to acquire the pulse wave of the user U.

As illustrated in FIG. 2, the light emitting device 120 is installed in the front of the vehicle, and the pulse wave imaging device 130 is installed in the vicinity of the center of the interior of the vehicle.

As illustrated in FIG. 3, the visible light source 101 and the infrared light source 104 are located, for example, on the edge portion of the display screen of the car navigation device at positions relatively close to the user U. The pulse wave measuring apparatus 140 captures an image of one of the cheeks of the user U via a rearview mirror M (in the rearview mirror M). The pulse wave measuring apparatus 140 captures an image of either one of the right and left cheeks of the user U that is closer to the rearview mirror M (i.e., the left cheek when the vehicle is a right-hand drive vehicle or the right cheek when the vehicle is a left-hand drive vehicle). This provides an advantage in that the cheek of the user U that is closer to the rearview mirror M can be irradiated with ease as the visible light source 101 and the infrared light source 104 are located on the car navigation device at positions closer to the user U, instead of the center of the car navigation device in the right and left direction. Thus, the visible light source 101 and the infrared light source 104 can irradiate more reliably the cheek of the user U from which the pulse wave can be acquired more easily with light beams in the respective wavelength bands. The rearview mirror M is also referred to as an interior front mirror.

Referring to FIG. 3, the pulse wave imaging device 130 includes two image sensors: the visible light imaging unit 102 and the infrared light imaging unit 103. The visible light imaging unit 102 takes in visible light through a first surface (a surface 102A) constituted by a portion of the surface of the visible light imaging unit 102, and the infrared light imaging unit 103 takes in infrared light through a second surface (a surface 103A) constituted by a portion of the surface of the infrared light imaging unit 103. The first surface and the second surface may or may not include regions that overlap each other. The first surface and the second surface may completely coincide with each other. The first surface is located in a first region between a first optical path of first reflection light and a second optical path of second reflection light. First light comes from an eye of the user sitting on a seat of the vehicle, and second light comes from a cheek of the user. An upper end of the interior front mirror of the vehicle reflects the first light to produce the first reflection light, and the stated upper end reflects the second light to produce the second reflection light.

In the pulse wave imaging device 130, when a vehicle with a right-hand steering wheel provided with the visible light imaging unit 102 is viewed from the above, the first surface may be located in a first region between a first optical path of first reflection light and a second optical path of second reflection light. First light comes from the left eye of the user sitting on the seat closest to the right-hand steering wheel of the vehicle, and second light comes from the left cheek of the user. A right end of the interior front mirror of the vehicle reflects the first light to produce the first reflection light, and the stated right end reflects the second light to produce the second reflection light. The stated right end is closer to the right-hand steering wheel than a left end of the interior front mirror of the vehicle is.

In the pulse wave imaging device 130, when a vehicle with a left-hand steering wheel provided with the visible light imaging unit 102 is viewed from the above, the first surface is located in a second region between a third optical path of third reflection light and a fourth optical path of fourth reflection light, third light comes from the right eye of the user sitting on the seat closest to the left-hand steering wheel of the vehicle, and fourth light comes from the right cheek of the user. The aforementioned left end reflects the third light to produce the third reflection light, and the stated left end reflects the fourth light to produce the fourth reflection light. The stated left end is closer to the left-hand steering wheel than the right end is.

The pulse wave imaging device 130 includes, inside a housing thereof, the visible light waveform computing unit 105, the infrared light waveform computing unit 106, the correlation degree computing unit 107, the light source controlling unit 108, and the biometric information calculating unit 109. The pulse wave imaging device 130 transmits obtained information to the light emitting device 120, and thus the biometric information and so on are displayed on the information presentation unit 110 of the light emitting device 120.

Each of the constituent elements described above will be described in detail, hereinafter.

Visible Light Source 101

The visible light source 101 irradiates the user U with light in the visible light range. The quantity of light that the visible light source 101 emits is adjusted by the light source controlling unit 108. Specifically, the visible light source 101 emits light in the wavelength range of from 400 nm to 800 nm. The visible light source 101 is implemented, for example, by a white light emitting diode (LED) or the like or by the display screen of the car navigation device.

The light emitting device 120 that includes the visible light source 101 is installed in the vicinity of the center of the dashboard of the vehicle, in a similar manner to a conventional car navigation device. In this case, when the visible light source 101 installed in the vicinity of the center of the dashboard emits visible light, the light illuminates an area around a cheek of the user U. A cheek of the user U is a site, among the face of the user U, from which the pulse wave can be acquired accurately with ease. Thus, irradiating a cheek with visible light as described above provides an advantage in that the pulse wave of the user U can be acquired accurately.

Specifically, the light emitting device 120 irradiates one of the right half and the left half of the face of the user U. For example, when the user U is the driver and the vehicle is a right-hand drive vehicle, the light emitting device 120 irradiates the left half of the face of the user U (when the vehicle is a left-hand drive vehicle, the light emitting device 120 irradiates the right half of the face of the user U) with light. When the visible light imaging unit 102 captures an image of the face of the user U via the rearview mirror M, the image is captured from a position slightly to the side of the user U with respect to the front of the user U. This configuration provides an advantage in that a more accurate pulse wave of the user U can be acquired with ease since no characteristic site such as an eye or a nose is in the imaging target.

Although the irradiation amount of the visible light source 101 is controlled by the light source controlling unit 108, this is not a limiting example. For example, the user U may manually control the irradiation amount of light by using a controller. In addition, the user U may adjust the direction of light emitted from the visible light source 101. For example, in order to allow the user U to adjust the orientation of the light emitting device 120 and to direct the emitted visible light and infrared light to hit the user U, the light emitting device 120 may include a universal joint mechanism or the like provided on the back side thereof to allow the user U to manually change the attitude of the light emitting device 120. This configuration allows the pulse wave measuring apparatus 140 to handle a situation in which the position of the face of the driver of the vehicle varies. In particular, the position of the face with respect to the vehicle while driving often differs between men and women. Therefore, allowing the driver to freely modify the attitude of the light emitting device 120 enables the pulse wave measuring apparatus 140 to measure the pulse wave of the user U more accurately.

In addition, although the visible light source 101 is installed on the edge portion of the display screen of the car navigation device in the present embodiment, the display screen of the car navigation device may serve as the visible light source 101. Typically, a display screen of a car navigation device is often used to check a map and/or the current location, and the car navigation device is often installed at the center position inside the vehicle as the vehicle is viewed from the above. Therefore, while the user U is driving, visible light emitted from the car navigation device primarily illuminates a side portion of the face of the user U.

In a case in which the pulse wave cannot be acquired from a cheek of the user U with the quantity of light emitted from the display screen during a navigation by a typical car navigation device, the quantity of light from the display screen of the car navigation device may be increased. Thus, even while the user U is checking a map with the car navigation device, the pulse wave measuring apparatus 140 can more easily acquire the pulse wave more accurately with the visible light from the car navigation device.

Although the light emitting device 120 is installed in the vicinity of the center of the dashboard of the vehicle, this is not a limiting example. For example, the light emitting device 120 may be installed in front of the user U. In this case, the visible light source 101 may irradiate the entire face, instead of either of the left half and the right half of the face, with light from the front of the user U. This increases the area of the face of the user U from which the pulse wave can be acquired, and the pulse wave measuring apparatus 140 can acquire the visible light pulse wave and the infrared light pulse wave more accurately.

For example, when the light emitting device 120 is installed in the vicinity of the center of the dashboard, of the right and left sides of the face of the user U, primarily only the one closer to the center of the vehicle in the right and left direction (i.e., the side farther from the window of the vehicle) is irradiated, which may not enable the pulse wave of the user U to be acquired due to an insufficient irradiation amount of light. In this case, if the light emitting device 120 is installed in front of the user U, of the right and left sides of the face of the user U, even the one farther from the center of the vehicle in the right and left direction (i.e., the side closer to the window of the vehicle) can also serve as the target region from which the pulse wave is acquired, which thus provides an advantage in that the measured pulse wave is more accurate.

The quantity of light emitted by the visible light source 101 will be described. The visible light source 101 is started when the engine of the vehicle is started while the brightness of the surroundings is insufficient for acquiring the pulse wave from the face of the user U with visible light (e.g., at night or while the vehicle is located inside a tunnel) or when the brightness of the surroundings has become insufficient for acquiring the pulse wave from the face of the user U with visible light while the user U is driving.

For example, in a case in which the visible light source 101 is started when the engine is started, the quantity of light emitted by the visible light source 101 prior to being started is zero. Then, as the engine is started, the visible light source 101 raises the quantity of light until the illuminance inside the vehicle reaches, for example, 1000 lux, and the quantity of light of each light source is controlled so that the visible light pulse wave acquired by the visible light waveform computing unit 105 and the infrared light pulse wave acquired by the infrared light waveform computing unit 106 coincide with each other. The method of computing the degree of correlation between the visible light pulse wave and the infrared light pulse wave and a specific method of controlling the light sources will be described later along with the correlation degree computing unit 107 and the light source controlling unit 108.

For example, when the surroundings become dark while the user U is driving and it becomes impossible to acquire the visible light pulse wave, the illuminance within the vehicle before the surroundings become dark is approximately 50 lux. This is an example of the illuminance in a case in which the user U uses the navigation function of the car navigation device. When the visible light waveform computing unit 105 becomes unable to acquire the visible light pulse wave in this state, the light source controlling unit 108 raises the quantity of light of the visible light source 101 until the illuminance within the vehicle reaches, for example, 1000 lux. Thereafter, in a similar manner to when the engine is started, the waveforms of the visible light pulse wave and the infrared light pulse wave are compared, and the visible light source 101 and the infrared light source 104 are controlled so that the infrared light pulse wave can be acquired. Thus, the pulse wave measuring apparatus 140 can detect the pulse wave even in a tunnel or an indoor parking in which the outside light is less likely to enter the interior of the vehicle. In particular, the heartbeat information of the user U can be extracted when the vehicle is located inside a tunnel for a relatively long period of time (specifically, when the vehicle is traveling inside a relatively long tunnel or when the vehicle is traveling at a low speed or at halt inside a tunnel due to traffic congestion regardless of the length of the tunnel).

Although the visible light source 101 is controlled so that the illuminance inside the vehicle reaches 1000 lux when the surrounding environment is dark when the engine is started, this is not a limiting example. The illuminance may take a smaller value (e.g., 500 lux) as long as the pulse wave can be acquired from the face of the user U at a given illuminance. Meanwhile, when the illuminance is too high, the interior of the vehicle is too bright to cause glare to the user U, which can cause an accident. In consideration of the above, the brightness inside the vehicle from the light emitted by the visible light source 101 preferably falls within a range from approximately 500 lux to 2500 lux. In the case of the user U of whom the pulse wave has been acquired previously, the illuminance at which the pulse wave has been acquired under the control of the visible light waveform computing unit 105 and the light source controlling unit 108 may be stored, and the quantity of light of the visible light source 101 may be set so as to achieve the stored illuminance. This provides an advantage in that the time it takes to acquire the pulse wave can be reduced and the process of adjusting the quantity of light every time can be reduced. When the user U is the same, it is highly likely that the features and so on of the color of the surface of the face are the same every time. Thus, it is highly likely that the pulse wave can be acquired by illuminating the face of the user U at the previously stored illuminance.

The visible light source 101 can acquire the visible light pulse wave with the visible light waveform computing unit 105. The quantity of light of the visible light source 101 when the slope between a peak and a bottom of the acquired pulse wave is greatest may be stored, and the quantity of light of the visible light source 101 may be brought to the stored value each time the quantity of light of the visible light source 101 is raised to acquire the pulse wave.

Although the visible light source 101 illuminates the face of the user U with light as the user U adjusts the attitude and the like of the light emitting device 120, this is not a limiting example. When the light emitted by the visible light source 101 is directed toward the eyes of the user U while the user U is driving, this causes glare to the user U, which can cause an accident. Therefore, for example, if the user U has an opportunity to adjust the attitude of the light emitting device 120 in advance, the user U may set the attitude such that a cheek of the user U is illuminated at a relatively high illuminance and the vicinity of the eyes of the user U is illuminated at a relatively low illuminance. The attitude of the light emitting device 120 may be set such that the center of the light beam emitted by the visible light source 101 is located underneath the center portion of a cheek. This makes it possible to adjust the illuminance without interfering with the driving of the user U.

In a case in which the quantity of light increases sharply while the user U is driving the vehicle, the face may be recognized in advance with the visible light imaging unit 102, an area from a cheek to the chin of the user U may first be irradiated with visible light on the basis of the result of the face recognition, the irradiation range may then be moved upward gradually, and the movement of the irradiation range may be stopped before the eyes of the user U are irradiated. This can be achieved by preventing the base of a signal of the luminance value of the position corresponding to the eyes obtained as the result of the face recognition from increasing.

Visible Light Imaging Unit 102

The visible light imaging unit 102 captures an image of an irradiation target irradiated by the visible light source 101 with visible light in the visible light range. The visible light imaging unit 102 is provided in a region including a region in an optical path of light coming from the user U and reflected by the rearview mirror M of the vehicle and excluding a region that the user U can see via the rearview mirror M. This can be rephrased as follows. That is, the visible light imaging unit 102 is provided at a position in an optical path of light coming from a cheek of the user U and reflected by the rearview mirror M of the vehicle excluding a position in an optical path of light coming from the eyes of the user U and reflected by the rearview mirror M. The visible light imaging unit 102 corresponds to a visible light receiver.

Specifically, the visible light imaging unit 102 outputs a visible light image obtained by capturing an image of an imaging target in the visible light range (e.g., in color) to the visible light waveform computing unit 105 of the pulse wave measuring apparatus 140. The visible light imaging unit 102 outputs, for example, a skin image obtained by capturing an image of the imaging target as the visible light image. The skin image is an image obtained by capturing images of a given site on the imaging target at a plurality of temporally successive timings and is constituted, for example, by a moving image or a plurality of still images.

The visible light imaging unit 102 may acquire the skin image by capturing the images or may acquire the skin image by acquiring data of the skin image captured by another device or the like. In the case in which the visible light imaging unit 102 captures the images, the visible light imaging unit 102 is implemented, for example, by a visible light camera or the like that includes an image sensor, such as a charge-coupled device (CCD) or a complementary metal-oxide semiconductor (CMOS) image sensor.

The visible light imaging unit 102 applies a filter to the image sensor to thus take in visible light, that is, light in the wavelength band of from 400 nm to 800 nm and acquires three types of signals in RGB (Red, Green, and Blue).

The visible light imaging unit 102 is provided in the pulse wave imaging device 130 installed at approximately the center position inside the vehicle. Hereinafter, the installation position of the visible light imaging unit 102 will be described in each of the cases in which the vehicle is viewed from a side and from the above.

First, the installation position of the visible light imaging unit 102 as the vehicle is viewed from a side will be described with reference to FIGS. 4A to 6B.

FIG. 4A is a descriptive diagram, as the vehicle is viewed from a side, illustrating a region that the user U can visually recognize via the rearview mirror M. The rearview mirror M is installed typically at a position higher than the position of the head of the user U serving as the driver. In addition, typically, the rearview mirror M is oriented downward, or in other words, the vector normal to the reflective surface of the rearview mirror M is directed downward with respect to the horizontal direction. This is because the driver sees the rearward of the vehicle through the rear window.

In FIG. 4A, the region that the user U can visually recognize via the rearview mirror M is a region R1 between an optical path P1 and an optical path P2. In other words, the user U can visually recognize the area inside the region R1 via the rearview mirror M and cannot visually recognize the area outside the region R1.

The optical path P1 is an optical path of light coming from the eyes of the user U and reflected by the upper end of the rearview mirror M. The optical path P1 and the normal N of the rearview mirror M form an angle having an angle θ1. In addition, the optical path P2 is an optical path of light coming from the eyes of the user U and reflected by the lower end of the rearview mirror M. The optical path P2 and the normal N of the rearview mirror M form an angle having an angle θ2.

The upper end and the lower end of the rearview mirror M may, respectively, be an upper end portion and a lower end portion thereof. The upper end portion and the lower end portion of the rearview mirror M refer to the areas extending several millimeters from the upper end and the lower end, respectively, on the reflective surface of the rearview mirror M (refer to FIG. 4B).

Figure 5:
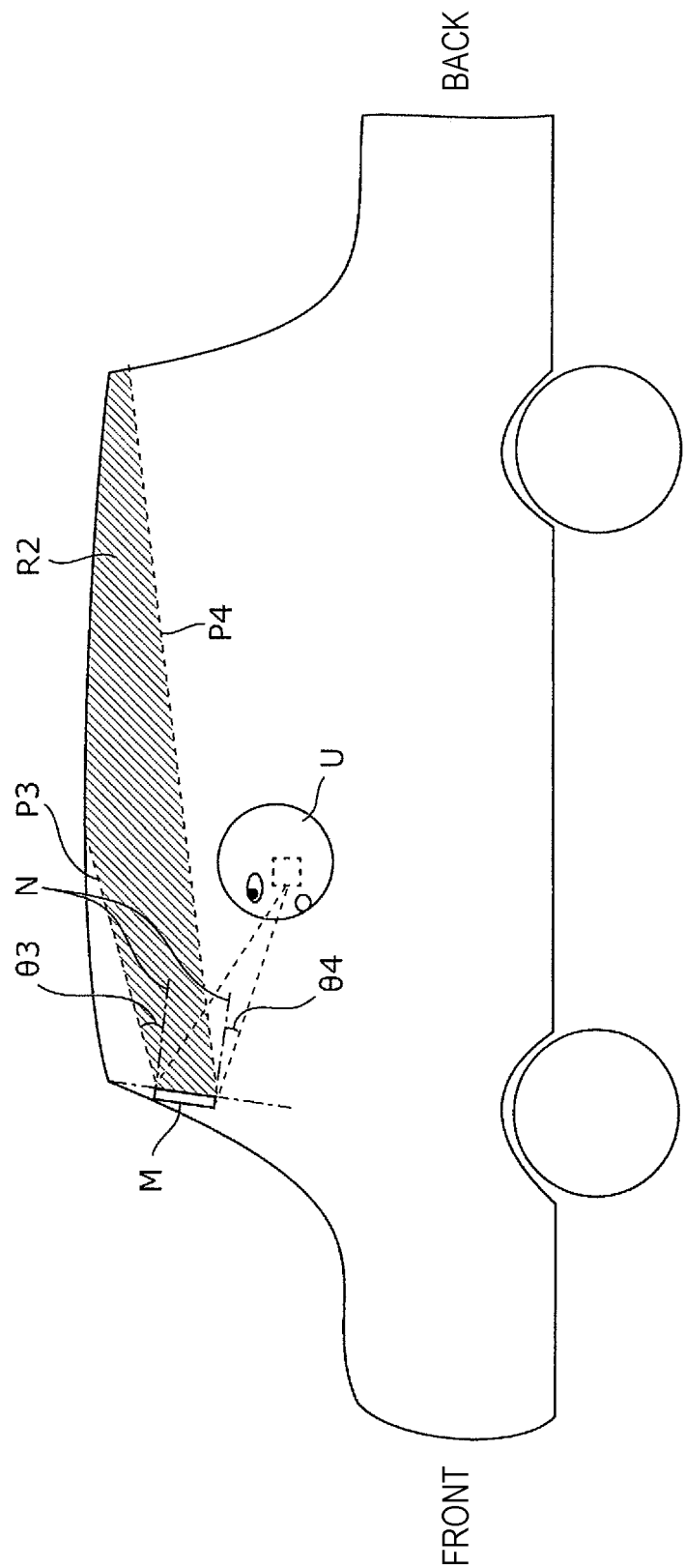
FIG. 5 is a descriptive diagram, as the vehicle is viewed from a side, illustrating a region in which a visible light imaging unit can be installed and in which the visible light imaging unit can capture an image of a cheek of a user via a rearview mirror according to an embodiment.

FIG. 5 is a descriptive diagram, as the vehicle is viewed from a side, illustrating a region in which the visible light imaging unit 102 can be installed and in which the visible light imaging unit 102 can capture an image of a cheek of the user U via the rearview mirror M according to the present embodiment.

In FIG. 5, the position of the visible light imaging unit 102 at which the visible light imaging unit 102 can capture an image of a cheek of the user U is in a region R2 between an optical path P3 and an optical path P4. In other words, the visible light imaging unit 102 installed within the region R2 can capture an image of a cheek of the user U.

The optical path P3 is an optical path of light coming from a cheek of the user U and reflected by the upper end portion of the rearview mirror M. The optical path P3 and the normal N of the rearview mirror M form an angle having an angle θ3. In addition, the optical path P4 is an optical path of light coming from a cheek of the user U and reflected by the lower end portion of the rearview mirror M. The optical path P4 and the normal N of the rearview mirror M form an angle having an angle θ4.

FIG. 6A is a descriptive diagram, as the vehicle is viewed from a side, illustrating a region in which the visible light imaging unit 102 (to be more specific, the first surface, or the surface 102A) can be installed and in which the visible light imaging unit 102 can capture an image of a cheek of the user U via the rearview mirror M and is not visually recognized by the user U according to the present embodiment. The optical paths, the angles, and the region illustrated in FIG. 6A are identical to those indicated by the identical reference characters in FIG. 4A and FIG. 5.

In FIG. 6A, the region in which an image of a cheek of the user U can be captured via the rearview mirror M and that is not visually recognized by the user U is a region R3 between the optical path P1 and the optical path P3. In other words, the region R3 is a region within the region R2 excluding the region R1.

Thus, when the visible light imaging unit 102 is installed within the region R3, the visible light imaging unit 102 can capture an image of a cheek of the user U via the rearview mirror M, and the user U does not visually recognize the visible light imaging unit 102. Therefore, the user U can drive without being distracted by the visible light imaging unit 102, and the pulse wave measuring apparatus 140 can acquire the pulse wave of the user U while driving.

Although FIG. 6A illustrates a case in which the eyes and the cheeks of the user are regarded as points, when the eyes and the cheeks of the user are each regarded as a region having a finite size, the following description holds.

Figure 6B:
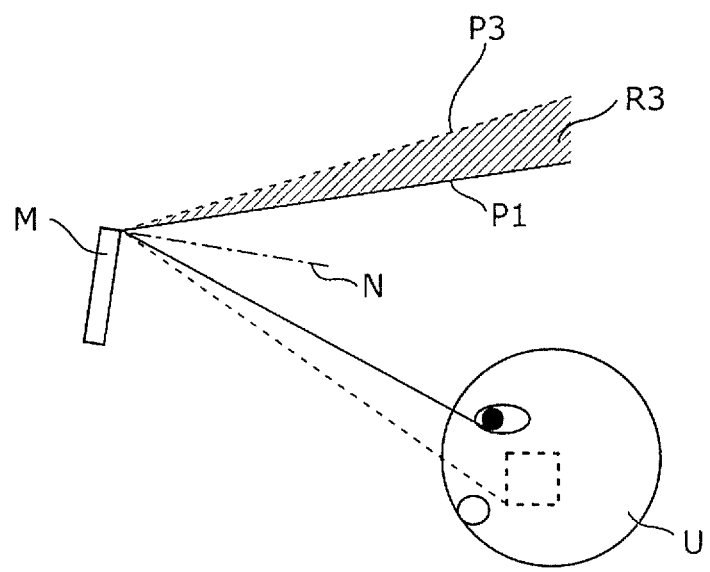
FIG. 6B is a descriptive diagram illustrating a case in which, with regard to the region illustrated in FIG. 6A, the eyes and the cheek of the user are each regarded as a region having a finite size.

FIG. 6B is a descriptive diagram illustrating a case in which, with regard to the region illustrated in FIG. 6A, the eyes and the cheeks of the user are each regarded as a region having a finite size.

In a case in which the eyes and the cheeks of the user are each regarded as a region having a finite size, the optical path P1 in the above description is considered to be an optical path of light coming from the lower ends of the eyes of the user U and reflected by the upper end of the rearview mirror M. In addition, the optical path P3 in the above description is considered to be an optical path of light coming from the lower end of a cheek of the user U and reflected by the upper end portion of the rearview mirror M. With the optical paths P1 and P3 set in this manner, the region R3 serving as a suitable region is set.

Next, the installation position of the visible light imaging unit 102 as the vehicle is viewed from the above will be described with reference to FIG. 7 to FIG. 9C. Here, a case in which the vehicle is a right-hand drive vehicle will be described. When the vehicle is a left-hand drive vehicle, the right and the left in the following description are to be switched.

Figure 7:
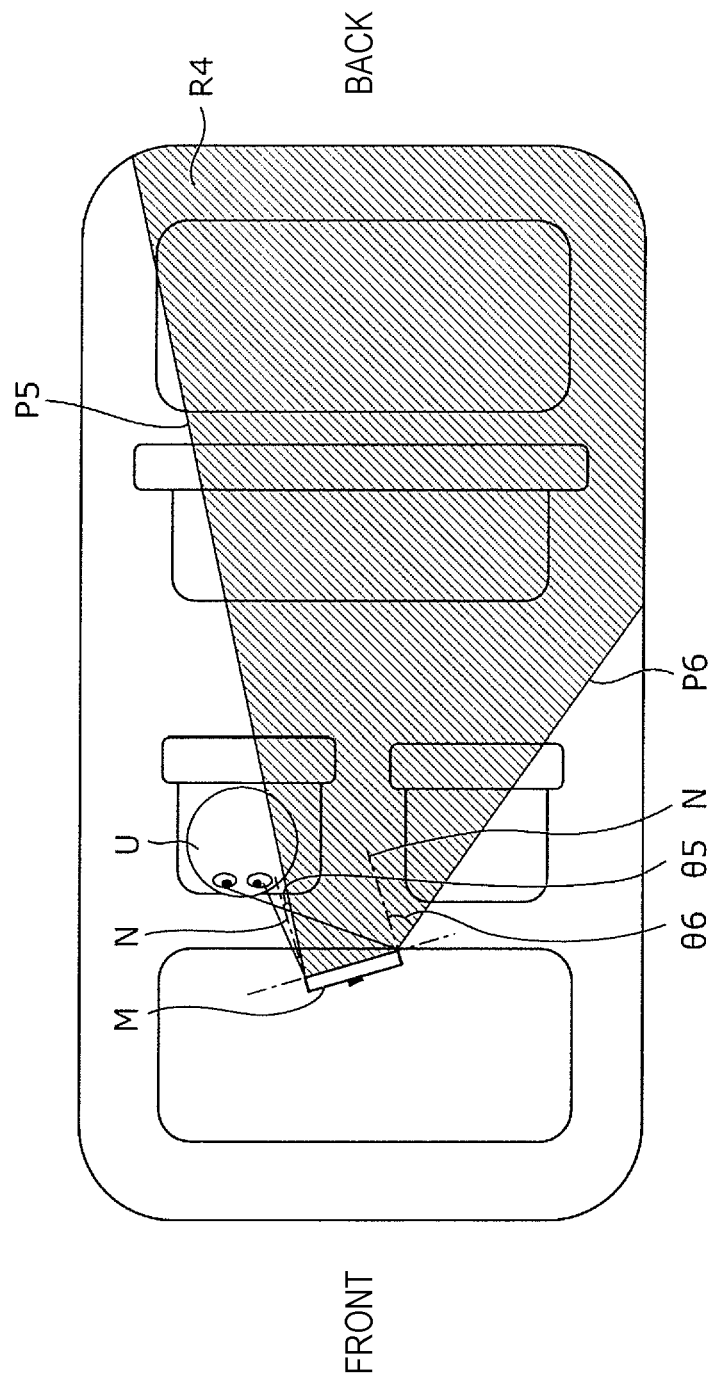
FIG. 7 is a descriptive diagram, as the vehicle is viewed from the above, illustrating a region that a user can visually recognize via a rearview mirror according to an embodiment.

In FIG. 7, the region that the user U can visually recognize via the rearview mirror M is a region R4 between an optical path P5 and an optical path P6. The region R4 is a maximum region that can be seen by at least one of the left eye and the right eye of the user U. In other words, the user U can visually recognize the area inside the region R4 via the rearview mirror M and cannot visually recognize the area outside the region R4.

The optical path P5 is an optical path of light coming from the left eye of the user U and reflected by the right end of the rearview mirror M. The optical path P5 and the normal N of the rearview mirror M form an angle having an angle θ5. In addition, the optical path P6 is an optical path of light coming from the right eye of the user U and reflected by the left end of the rearview mirror M. The optical path P6 and the normal N of the rearview mirror M form an angle having an angle θ6.

The left end and the right end of the rearview mirror M may be, respectively, a left end portion and a right end portion thereof. The left end portion and the right end portion of the rearview mirror M refer to the areas extending several millimeters from the left end and the right end, respectively, on the reflective surface of the rearview mirror M (refer to FIG. 4B).

Figure 8:
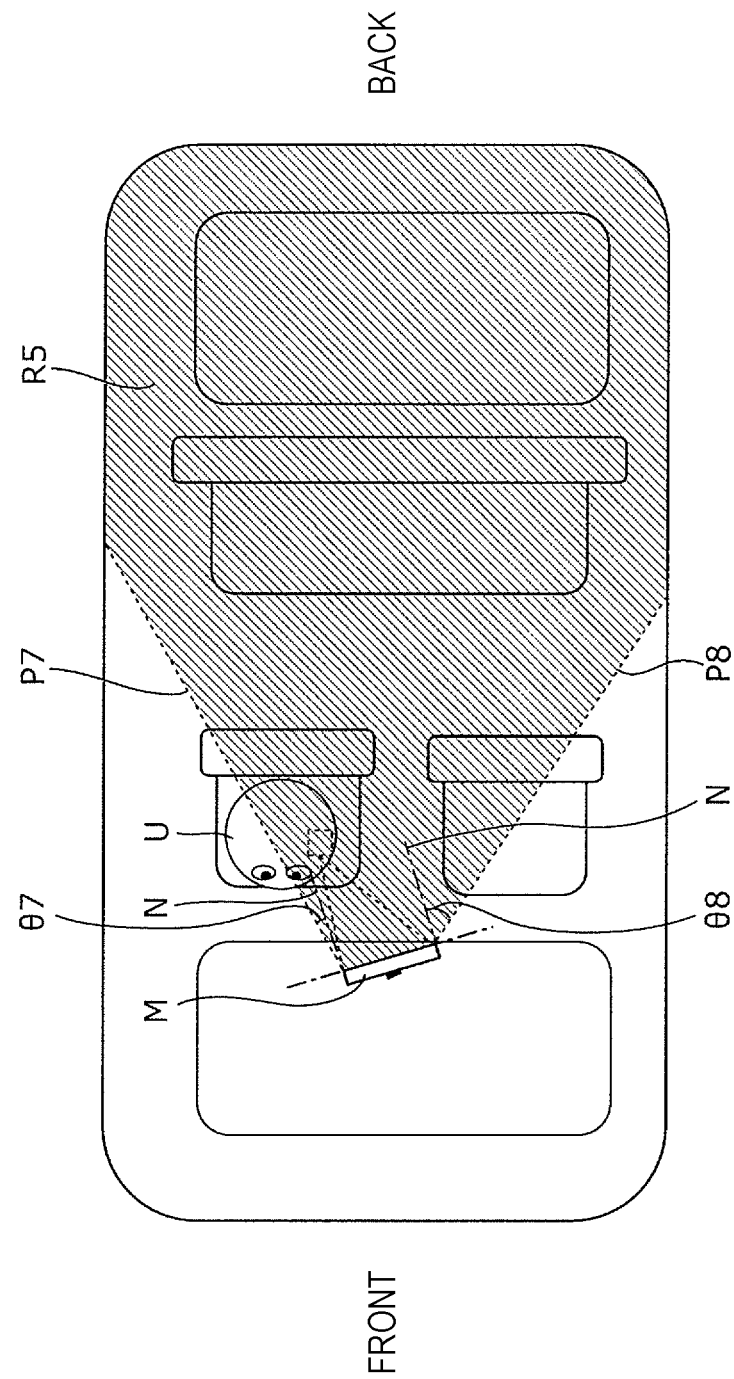
FIG. 8 is a descriptive diagram, as the vehicle is viewed from a side, illustrating a region in which a visible light imaging unit can be disposed and in which the visible light imaging unit can capture an image of a cheek of a user via a rearview mirror according to an embodiment.

FIG. 8 is a descriptive diagram, as the vehicle is viewed from the above, illustrating a region in which the visible light imaging unit 102 can be installed and in which the visible light imaging unit 102 can capture an image of a cheek of the user U via the rearview mirror M according to the present embodiment.

In FIG. 8, the position of the visible light imaging unit 102 at which the visible light imaging unit 102 can capture an image of a cheek of the user U is in a region R5 between an optical path P7 and an optical path P8. In other words, the visible light imaging unit 102 installed within the region R5 can capture an image of a cheek of the user U.

The optical path P7 is an optical path of light coming from a cheek of the user U and reflected by the right end portion of the rearview mirror M. The optical path P7 and the normal N of the rearview mirror M form an angle having an angle θ7. In addition, the optical path P8 is an optical path of light coming from a cheek of the user U and reflected by the left end portion of the rearview mirror M. The optical path P8 and the normal N of the rearview mirror M form an angle having an angle θ8.

Figure 9B:
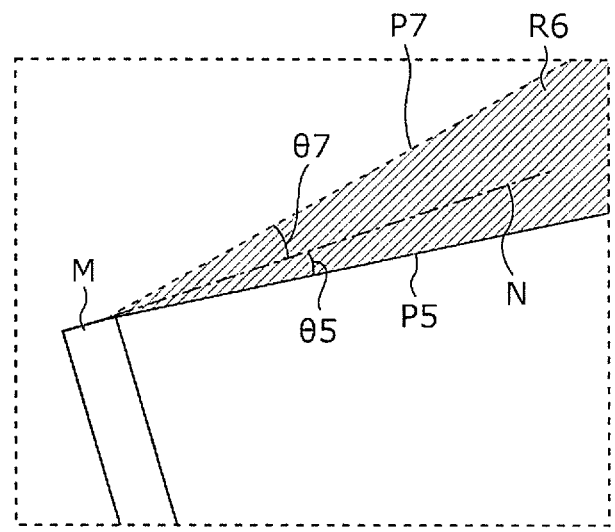
FIG. 9B is a fragmentary enlarged view, as the vehicle is viewed from the above, illustrating a region in which a visible light imaging unit can be installed according to an embodiment.

FIG. 9A and FIG. 9B are descriptive diagrams, as the vehicle is viewed from the above, illustrating a region in which the visible light imaging unit 102 (to be more specific, the first surface, or the surface 102A) can be installed and in which the visible light imaging unit 102 can capture an image of a cheek of the user U via the rearview mirror M and is not visually recognized by the user U according to the present embodiment. FIG. 9A illustrates the vehicle as a whole, and FIG. 9B is a fragmentary enlarged view of the vicinity of the rearview mirror M. The optical paths, the angles, and the regions illustrated in FIG. 9A and FIG. 9B are identical to those indicated by the identical reference characters in FIG. 7 and FIG. 8.

In FIG. 9A and FIG. 9B, the region in which an image of a cheek of the user U can be captured via the rearview mirror M and that is not visually recognized by the user U is a region R6 between the optical path P5 and the optical path P7. In other words, the region R6 is a region within the region R5 excluding the region R4.

Thus, when the visible light imaging unit 102 is installed within the region R6, the visible light imaging unit 102 can acquire an image of a cheek of the user U via the rearview mirror M, and the user U does not visually recognize the visible light imaging unit 102. Therefore, the user U can drive without being distracted by the visible light imaging unit 102, and the pulse wave measuring apparatus 140 can acquire the pulse wave of the user U while driving.

As described thus far, when the visible light imaging unit 102 is installed within the region R3 as the vehicle is viewed from a side (FIG. 6A) or within the region R6 as the vehicle is viewed from the above (FIG. 9A and FIG. 9B), the user U can drive without paying attention to the camera constituted by the visible light imaging unit 102, and the pulse wave measuring apparatus 140 can acquire the pulse wave of the user U while driving. The expression "the region R3 as the vehicle is viewed from a side or the region R6 as the vehicle is viewed from the above" can also be stated as a region of a union of the region R3 as the vehicle is viewed from a side and the region R6 as the vehicle is viewed from the above. This region is also referred to as a "suitable region."

Although FIG. 9A and FIG. 9B illustrate a case in which the eyes and the cheeks of the user are regarded as points, when the eyes and the cheeks of the user are each regarded as a region having a finite size, the following description holds.

Figure 9C:
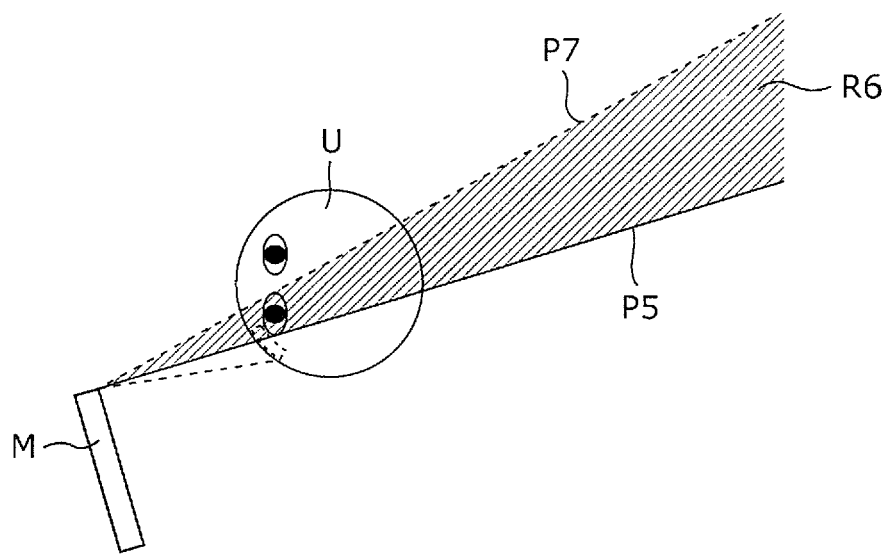
FIG. 9C is a descriptive diagram illustrating a case in which, with regard to the region illustrated in FIG. 9A, the eyes and the cheek of the user are each regarded as a region having a finite size.

FIG. 9C is a descriptive diagram illustrating a case in which, with regard to the regions illustrated in FIG. 9A and FIG. 9B, the eyes and the cheeks of the user are each regarded as a region having a finite size.

In a case in which the eyes and the cheeks of the user are each regarded as a region having a finite size, the optical path P5 in the above description is considered to be an optical path of light coming from the left end of the left eye (the corner of the left eye) of the user U and reflected by the right end of the rearview mirror M. In addition, the optical path P7 in the above description is considered to be an optical path of light coming from the left end of a cheek of the user U and reflected by the right end portion of the rearview mirror M. With the optical paths P5 and P7 set in this manner, the region R6 serving as a suitable region is set.

While the position of the visible light imaging unit 102 as the vehicle is viewed from a side is being restricted, the visible light imaging unit 102 may be installed at a position, as viewed from the above, at which the visible light imaging unit 102 can capture an image of the eyes of the user U. In a case in which the visible light imaging unit 102 is installed in the region R6 as viewed from the above (FIG. 9A and FIG. 9B), when the ceiling of the vehicle is relatively low or when the sitting height of the user U is relatively high, the rearview mirror M is behind the head of the user U as viewed from the visible light imaging unit 102, and an image of the rearview mirror M may not be captured. In such a case, the installation position of the visible light imaging unit 102 may be restricted to a region, as viewed from a side, from which an image of the eyes of the user U cannot be captured but an image of a cheek of the user U can be captured and to a region, as viewed from the above, that is not behind the head of the user U and from which an image of a cheek of the user U can be captured. Thus, even in a case in which the driver changes to a user with a high sitting height, the pulse wave can be acquired from a cheek by shifting the installation position.

The method of installing the visible light imaging unit 102 will now be described. As described above, the visible light imaging unit 102 needs to be installed at a position that is not visually recognized by the user U via the rearview mirror M. According to the method described hereinafter, the position at which the visible light imaging unit 102 should be installed is determined on the basis of the region that the user U visually recognizes via the rearview mirror M.

Figure 10A:
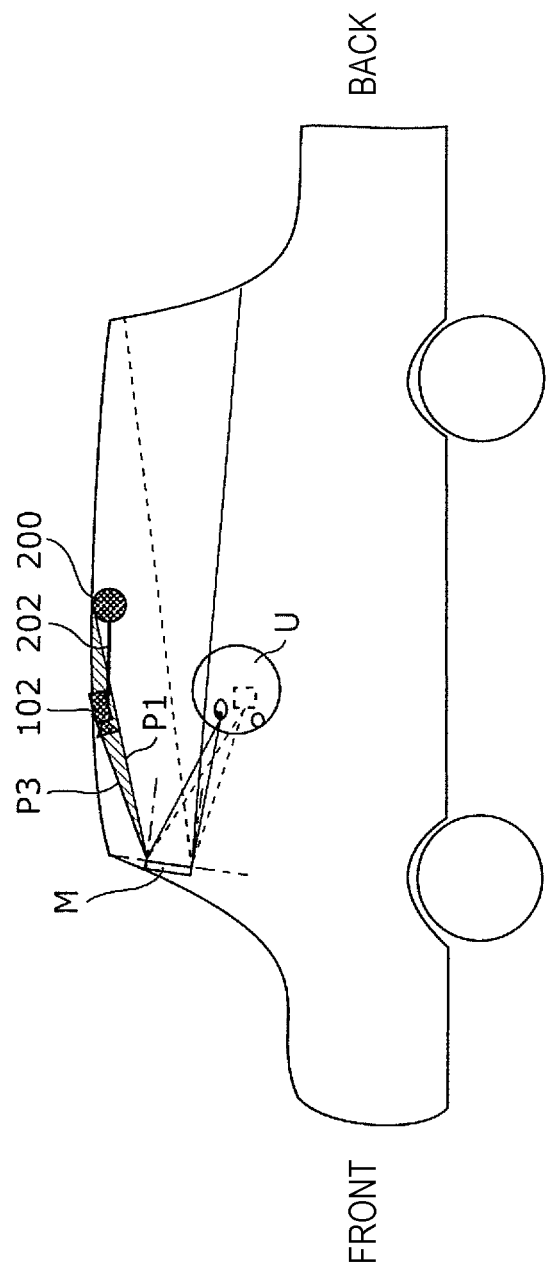
FIGS. 10A and 10B are illustrations for describing a method of installing a camera according to an embodiment.
Figure 10B:
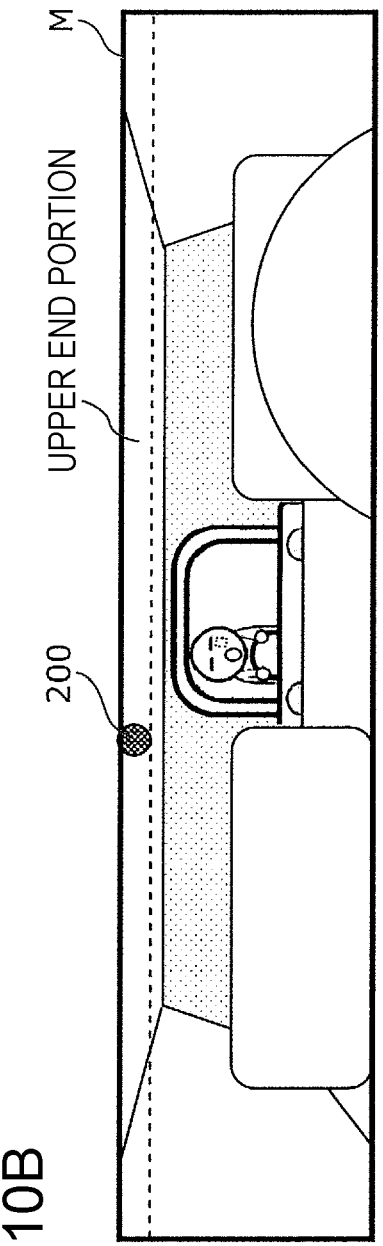

First, as illustrated in FIGS. 10A and 10B, a mark 200 is placed at a position that the user U visually recognizes via the upper end portion of the rearview mirror M. In other words, the mark 200 is placed at a position in the optical path P1 of the light coming from the eyes of the user U and reflected by the upper end portion of the rearview mirror M, such as an intersection of the optical path P1 and the ceiling of the interior space of the vehicle. The mark 200 may be placed by coloring with a marker or the like, may be placed with a seal or the like being affixed thereto, or may be a coupling member or an engagement member such as a screw or a hook.

Then, an arm 202 is attached to the mark 200. The arm 202 is fixed at one end to the mark 200, and a camera constituted by the visible light imaging unit 102 is attached to another end of the arm 202. The arm 202 is, for example, a stick having a predetermined length (the length L in (a) of FIG. 11A, which is approximately 10 cm, for example). The stated predetermined length corresponds to a first distance. Constituting the mark 200 by a coupling member or an engagement member provides an advantage in that fixing of the one end of the arm 202 to the mark 200 is facilitated.

In this manner, the visible light imaging unit 102 is provided by using the arm 202 at a position that is above the optical path P1 and that is to the front of the vehicle by the first distance from the position in the optical path P1.

When the mark 200 hinders the field of view of the user U, the mark 200 may be removed after the camera is installed.

This installation method provides an advantage in that the user U can carry out the installation alone. The user U places the mark 200 and attaches the camera to the front with respect to the mark 200, and thus the user U can install the camera in the suitable region with ease. After the installation, when the user U checks whether the user U can visually recognize vehicles behind via the rearview mirror M, the pulse wave measuring apparatus 140 may check whether the pulse wave can be acquired and may present the result through the information presentation unit 110. Thus, the user U can find whether the pulse wave measuring apparatus 140 can acquire the pulse wave while adjusting the field of view via the rearview mirror M and can take an appropriate action for an improvement as necessary.

Furthermore, after the adjustment is completed, the visible light imaging unit 102 may store the attitude held at the position at which the adjustment is completed, or more specifically, may store the angle in the up and down direction and the angle in the right and left direction. For example, the visible light imaging unit 102 may include an angle sensor for two directions. In addition, the pulse wave measuring apparatus 140 may store the angle held when the visible light waveform computing unit 105 is confirmed to be able to acquire the pulse wave and the adjustment of the rearview mirror M is completed. In this case, the stated angle may be stored along with an image of the face, the eyes, or the nose of the user U, and thus the angle of the camera may be set automatically to the stored angle when the identical user is on board the vehicle. Thus, the amount by which the angle of the rearview mirror M is to be adjusted each time the user U is on board the vehicle is reduced, which can save trouble for the user U.

Figure 11A:
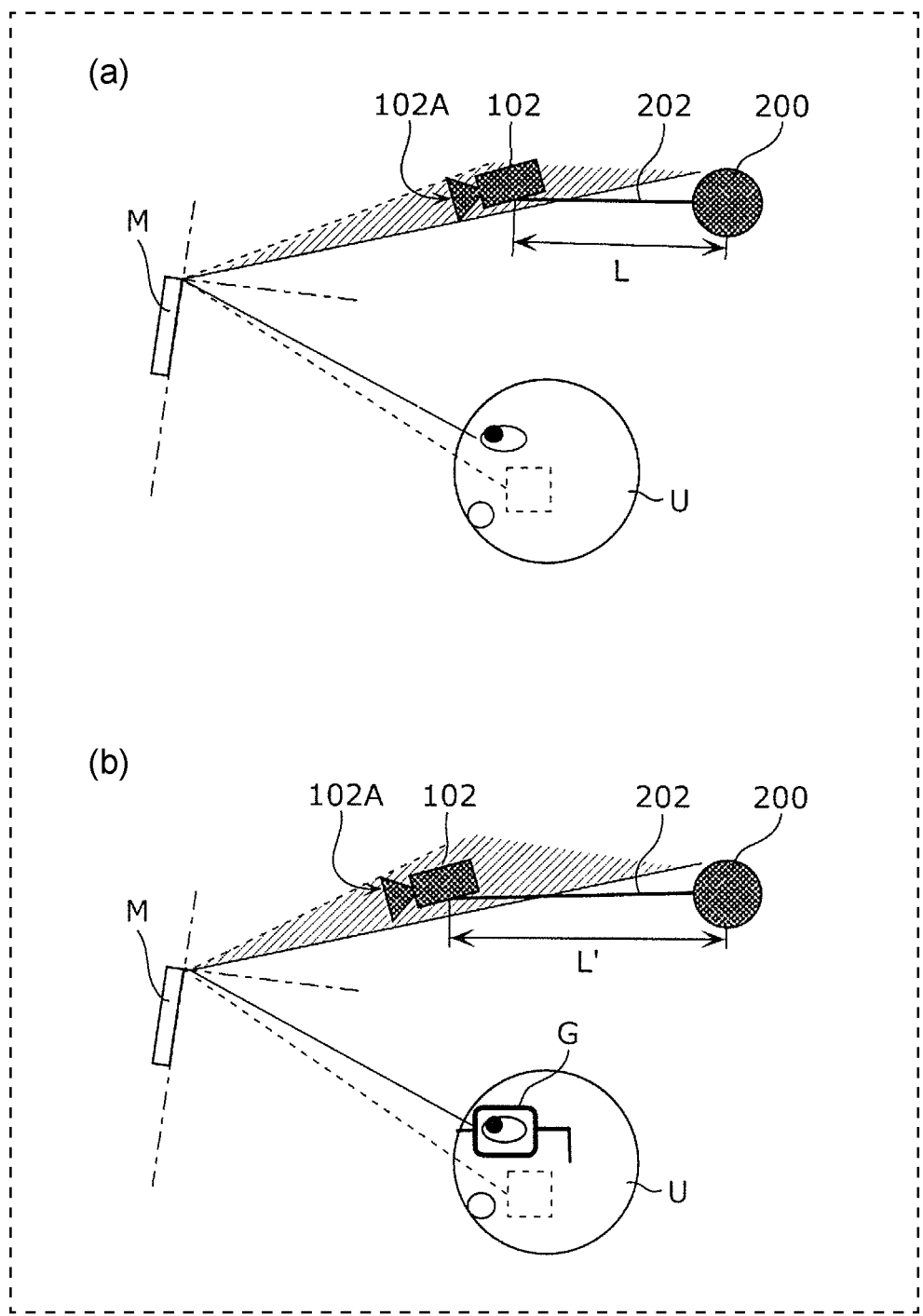
FIG. 11A is an illustration for describing a method of installing a camera in a case in which a user wears eyeglasses according to an embodiment.

Furthermore, when the user U wears eyeglasses G, the eyeglasses G may overlap a region of a cheek (refer to FIG. 11A). Therefore, as compared to a user U who does not wear eyeglasses G, in the case of the user U wearing the eyeglasses G, the pulse wave may be acquired by capturing an image of a relatively lower region of a cheek with the visible light imaging unit 102.

The section (a) of FIG. 11A illustrates a position of the visible light imaging unit 102 (to be more specific, the first surface, or the surface 102A) in a case in which the user U does not wear the eyeglasses G, and the section (b) of FIG. 11A illustrates a position of the visible light imaging unit 102 in a case in which the user U wears the eyeglasses G.

When (a) and (b) of FIG. 11A are compared, in (b) of FIG. 11A, the region of the cheek of which the visible light imaging unit 102 captures an image is located downward since the user U wears the eyeglasses G. Therefore, the visible light imaging unit 102 for acquiring the pulse wave of the user U wearing the eyeglasses G needs to be installed further to the front as compared to the case of the user U who does not wear the eyeglasses G.

Thus, in the case in which the user U wears the eyeglasses G, the pulse wave measuring apparatus 140 may install the camera of the visible light imaging unit 102 with the length of the arm 202 set to a length greater than the aforementioned predetermined length (the length L' in (b) of FIG. 11A, which is 20 cm, for example). In addition, a configuration in which the length of the arm 202 can be varied with a mechanism for expansion and contraction or the like may be employed. The stated length greater than the predetermined length corresponds to a second distance. The determination as to whether the user U wears the eyeglasses G can be made, for example, through image processing on a face image of the user U captured by the visible light imaging unit 102.

To be more specific, the pulse wave measuring apparatus 140 may include a determiner 300 that determines whether the user U wears the eyeglasses G through image processing, and a mover 400 that, in a case in which the determiner 300 has determined that the user U wears the eyeglasses G, causes the camera to be located at a position that is above the optical path P3 and that is to the front of the vehicle by the second distance that is greater than the first distance from the position in the optical path P3, as the vehicle is viewed from a side.

Thus, even the user U wearing the eyeglasses G can drive without paying attention to the camera, and the pulse wave measuring apparatus 140 can acquire the pulse wave information of the user U while driving.

There is a variety of types of vehicles. The shape of the vehicle and the positions of the eyes and cheeks of the user differ for different types of vehicles, and thus the installation position of the visible light imaging unit 102 differs accordingly. Thus, the installation position of the visible light imaging unit 102 for different types of vehicles will be described by way of examples.

Figure 11B:
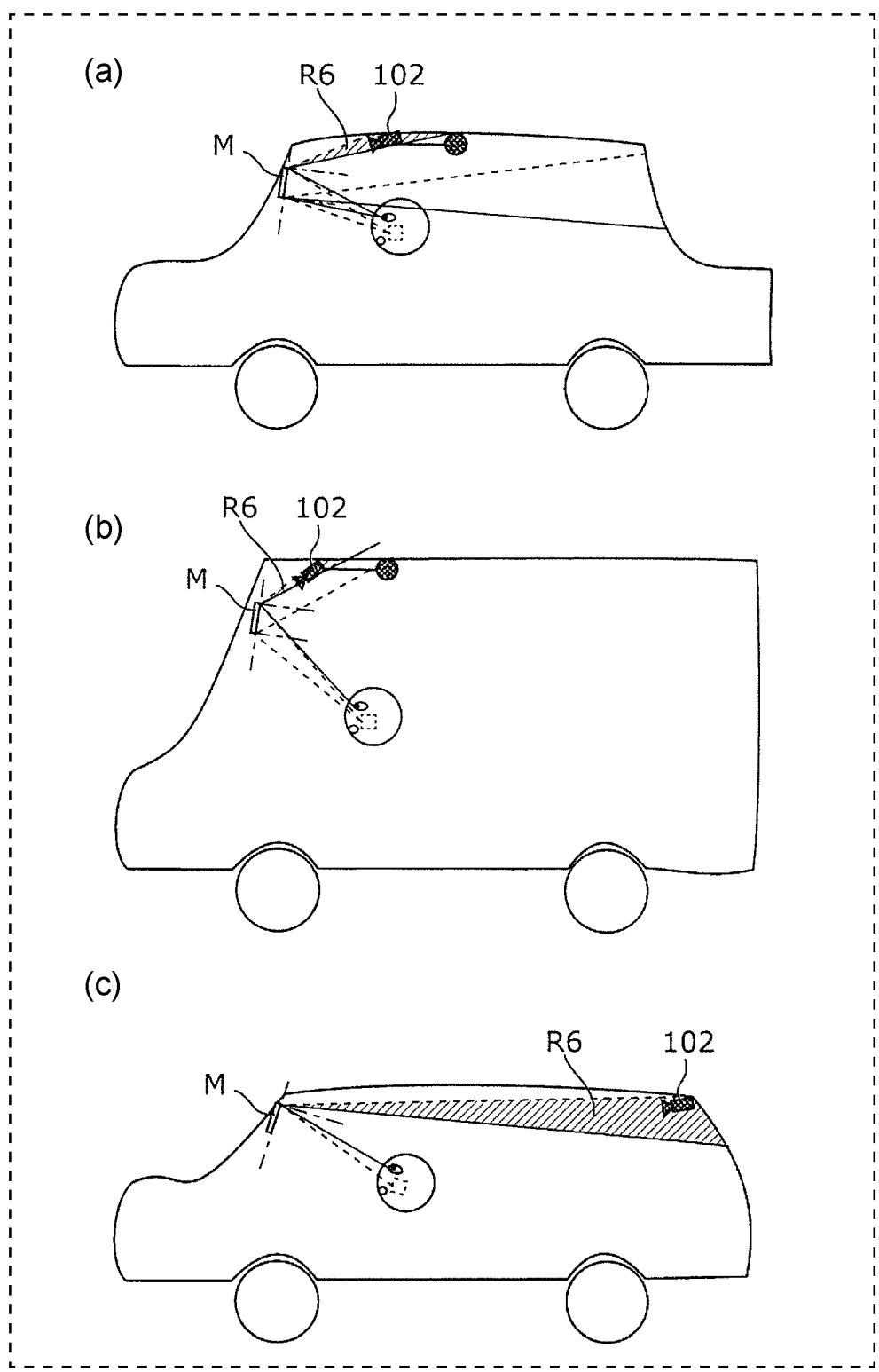
FIG. 11B is a descriptive diagram illustrating examples of an installation position of a visible light imaging unit for different types of vehicles according to an embodiment.

FIG. 11B is a descriptive diagram illustrating examples of the installation position of the visible light imaging unit 102 for different types of vehicles according to the present embodiment. In FIG. 11B, (a) illustrates a region R3 in a sedan type vehicle, (b) illustrates a region R3 in a van type vehicle, and (c) illustrates a region R3 in a sports car type vehicle.

To the sedan type vehicle illustrated in (a) of FIG. 11B, what has been described thus far applies.

In the case of the van type vehicle illustrated in (b) of FIG. 11B, the ceiling inside the vehicle is higher than that of a sedan type vehicle, and the position of a rearview mirror is high. In addition, the region R3 serving as a suitable region in which the visible light imaging unit 102 can be installed is narrower than that in a sedan type vehicle.

In the case of the sports car type vehicle illustrated in (c) of FIG. 11B, the ceiling inside the vehicle is lower than that of a sedan type vehicle, and the angle of the rearview mirror is oriented downward. In addition, the region R3 serving as a suitable region in which the visible light imaging unit 102 can be installed is broader than that in a sedan type vehicle.

In this manner, the region R3 serving as a suitable region differs for different types of vehicles. The visible light imaging unit 102 is installed at different positions for different types of vehicles and can capture an image of a user.

Infrared Light Imaging Unit 103

The infrared light imaging unit 103 captures an image of an irradiation target irradiated by the infrared light source 104 with infrared light in the infrared light range. The infrared light imaging unit 103 is provided in a region including a region in an optical path of light coming from the user U and reflected by the rearview mirror M and excluding a region that the user U can see via the rearview mirror M. This can be rephrased as follows. That is, the infrared light imaging unit 103 is provided at a position in an optical path of light coming from a cheek of the user U and reflected by the rearview mirror M and excluding a position in an optical path of light coming from the eyes of the user U and reflected by the rearview mirror M. The infrared light imaging unit 103 corresponds to an infrared light receiver.

Specifically, the infrared light imaging unit 103 outputs an infrared light image obtained by capturing an image of the skin of the user U serving as an irradiation target in the infrared light range (e.g., in monochrome) to the infrared light waveform computing unit 106 of the pulse wave measuring apparatus 140. The infrared light imaging unit 103 captures an image of the same site as the visible light imaging unit 102. The infrared light imaging unit 103 outputs, for example, a skin image obtained by capturing an image of the skin including the face or a hand of a person as the infrared light image. A reason for this is that, as the infrared light imaging unit 103 and the visible light imaging unit 102 capture the images of the same site, similar pulse waves can be acquired in the visible light range and the infrared light range, which makes it easier to compare the feature amounts.

For capturing the images of the same site, a region of interest (ROI) is set to have the same size in the visible light imaging unit 102 and the infrared light imaging unit 103. Then, the images within the ROI captured by the visible light imaging unit 102 and the infrared light imaging unit 103 may be compared, for example, with the use of pattern recognition to determine whether the same site has been captured. In addition, the same site may be identified by carrying out face recognition in each of the visible light image obtained by the visible light imaging unit 102 and the infrared light image obtained by the infrared light imaging unit 103, acquiring the coordinates and the size of a feature point at an eye, a nose, a mouse, or the like, and computing the coordinates (the relative position) from the feature point such as the eye, the nose, the mouse, or the like with the ratio of the size of the eye, the nose, the mouse, or the like taken into consideration.

The skin image obtained by the infrared light imaging unit 103 is an image obtained by capturing images of a given site on the skin including the face or a hand of a person at a plurality of temporally successive timings and is constituted, for example, by a moving image or a plurality of still images, in a similar manner to the skin image obtained by the visible light imaging unit 102.

The installation position of the infrared light imaging unit 103 is determined in a similar manner to that of the visible light imaging unit 102. Specifically, the infrared light imaging unit 103 is installed within the region R3 as the vehicle is viewed from a side (FIG. 6A) or within the region R6 as the vehicle is viewed from the above (FIG. 9A and FIG. 9B), or in other words, installed within a suitable region. Thus, the user U can drive without paying attention to the camera constituted by the infrared light imaging unit 103, and the pulse wave measuring apparatus 140 can acquire the pulse wave of the user U while driving.

The visible light imaging unit 102 and the infrared light imaging unit 103 may be disposed side by side inside the housing of the pulse wave imaging device 130. A reason for this is that, as the infrared light imaging unit 103 and the visible light imaging unit 102 acquire images of the same site as much as possible, a more appropriate pulse wave can be acquired.

When the infrared light imaging unit 103 and the visible light imaging unit 102 are to be disposed side by side, there is a possibility that the infrared light imaging unit 103 or the visible light imaging unit 102 goes outside the suitable region. In that case, the infrared light imaging unit 103 and the visible light imaging unit 102 may be disposed side by side in the right and left direction with their heights in the up and down direction being flush with each other. For example, in a case in which the width of the suitable region in the up and down direction is sufficient only for one camera, the two cameras (the infrared light imaging unit 103 and the visible light imaging unit 102) may be disposed side by side in the right and left direction. Thus, a situation in which only one of the cameras of the infrared light imaging unit 103 and the visible light imaging unit 102 can be installed can be avoided, and switching from imaging with visible light to imaging with infrared light becomes possible.

The method of installing the infrared light imaging unit 103 is the same as the method of installing the visible light imaging unit 102 described above.

Infrared Light Source 104

The infrared light source 104 irradiates the user U with infrared light. The quantity of light that the infrared light source 104 emits is adjusted by the light source controlling unit 108. Specifically, the infrared light source 104 is implemented, for example, by an infrared LED or the like that emits light in the wavelength range of from 800 nm to 2500 nm.

Since there is a possibility that the eyesight deteriorates if the eyes of a person keep being irradiated with infrared light, the face of the user U may be irradiated within a limited ROI. For example, when the face of the user U is to be irradiated with light, it is easier to acquire the pulse wave from the cheeks in particular. In this case, the face recognition may be carried out with the image captured by the infrared light imaging unit 103, and an area underneath the eyes may be irradiated. In addition, in a case in which the power of the infrared light is at a predetermined threshold value or higher and a predetermined period of time or more has passed, the quantity of light may be reduced.

In a similar manner to the visible light source 101, a driving unit may be provided, and when the quantity of infrared light has exceeded a predetermined threshold value in the light source controlling unit 108 and the feature points of the pulse wave have not been able to be acquired in the infrared light waveform computing unit 106, the face of the user U may be identified with the use of a face recognition program with respect to the image obtained by the infrared light imaging unit 103, and the irradiation direction of the light may be changed to the direction toward the face.

As described above, since infrared light may influence the eyesight of the user U, the location of the cheeks may be identified through the face recognition of the user U, and the irradiation region may be restricted so that the cheeks of the user U are irradiated with infrared light.

The infrared light source 104 may be disposed, for example, at a position closer to the center line of the vehicle in the right and left direction than to the seat (driver's seat) on which the user U sits. For example, the infrared light source 104 is installed on the edge portion of the display screen of the car navigation device used by the user U. Thus, when the user U is facing toward the front (forward) while driving, the infrared light source 104 can irradiate the user U from a side with light, which thus provides a feature that the pulse wave can be acquired with ease.

Visible Light Waveform Computing Unit 105

The visible light waveform computing unit 105 acquires a visible light image from the visible light imaging unit 102 and extracts a visible light waveform, which is a waveform that represents the visible light pulse wave of the user U, from the acquired visible light image. The visible light waveform computing unit 105 may extract a plurality of first feature points, which are predetermined feature points in the extracted visible light waveform. The predetermined feature point is, for example, a peak point, which is a crest or a trough, in the waveform within one cycle of the pulse wave of the user U. The visible light waveform computing unit 105 corresponds to a pulse wave calculator.

The visible light waveform computing unit 105 acquires a timing of the pulse wave as a feature point of the visible light waveform and computes a heartbeat interval time from adjacent timings of the pulse wave. In other words, the visible light waveform computing unit 105 calculates, for each of the plurality of extracted first feature points, the time between a given first feature point and another first feature point adjacent to the given first feature point as a first heartbeat interval time.

Specifically, the visible light waveform computing unit 105 extracts a visible light waveform on the basis of a change over time in the luminance extracted from a plurality of visible light images that are each associated with a timing at which the visible light image has been captured. In other words, each of the plurality of visible light images acquired from the visible light imaging unit 102 is associated with a time point at which the visible light image has been captured in the visible light imaging unit 102. The visible light waveform computing unit 105 acquires the interval between predetermined feature points of the visible light waveform and thus acquires the timing of the pulse wave of the user U (hereinafter, also referred to as a pulse wave timing). Then, the visible light waveform computing unit 105 calculates, for each of the plurality of obtained pulse wave timings, the interval between a given pulse wave timing and another pulse wave timing following the given pulse wave timing as the heartbeat interval time.

For example, the visible light waveform computing unit 105 identifies the timing at which the luminance changes the most by using the extracted visible light waveform and identifies the identified timing as the pulse wave timing. Alternatively, the visible light waveform computing unit 105 identifies the position of the face or a hand in a plurality of visible light images by using a pattern of the face of a hand stored in advance and identifies the visible light waveform by using the change over time in the luminance at the identified position. The visible light waveform computing unit 105 calculates the pulse wave timing by using the identified visible light waveform. Here, the pulse wave timing is a time point at a predetermined feature point in the temporal waveform of the luminance, or in other words, in the temporal waveform of the pulse wave. The predetermined feature point is, for example, a peak position in the temporal waveform of the luminance (the time point of the crest). The peak position can be identified, for example, by using a well-known local search method including a method that employs hill climbing, autocorrelation, and a differential function.

Typically, the pulse wave is a change in the blood pressure or the volume within a peripheral blood vessel system in association with pulsation of the heart. In other words, the pulse wave is a change in the volume of the blood vessel as the heart contracts to pump out the blood from the heart and the blood reaches the face, a hand, or the like. When the volume of the blood vessel in the face, a hand, or the like changes in this manner, the amount of blood passing through the blood vessel changes, and the color of the skin changes depending on the amount of components, such as hemoglobin, in the blood. Therefore, the luminance of the face or a hand in a captured image changes in accordance with the pulse wave. In other words, information pertaining to the movement of the blood can be acquired by using the change over time in the luminance of the face or a hand obtained from the images of the face or a hand captured at a plurality of timings. In this manner, the visible light waveform computing unit 105 acquires the pulse wave timing by computing the information pertaining to the movement of the blood from the plurality of images captured in time series.

To acquire the pulse wave timing in the visible light range, an image that captures the luminance in the wavelength range of green in the visible light image may be used. In the image captured in the visible light range, the change associated with the pulse wave appears prominently in the luminance in the wavelength range around green. In a visible light image including a plurality of pixels, the luminance in the wavelength range of green in a pixel corresponding to the face or a hand in a state in which a large amount of blood has flowed therein is lower than the luminance in the wavelength range of green in a pixel corresponding to the face or a hand in a state in which a small amount of blood has flowed therein.

Figure 12A:
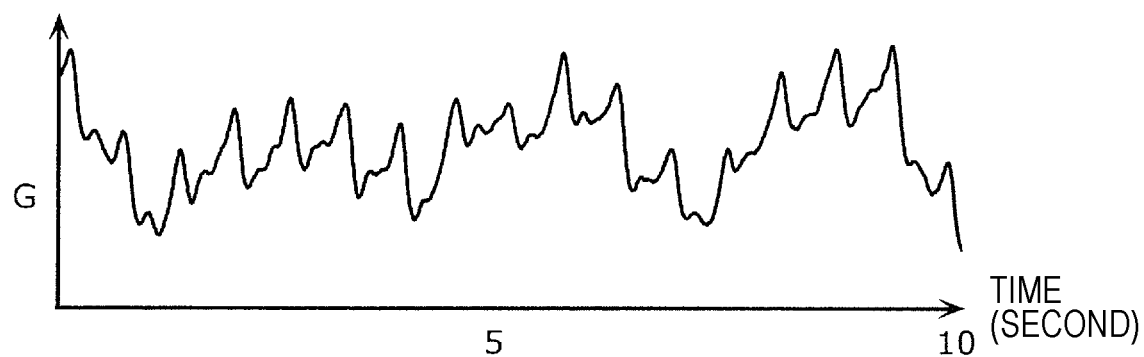
FIGS. 12A and 12B are graphs illustrating an example of a change in the luminance of a visible light image and an infrared light image according to an embodiment.

FIG. 12A is a graph illustrating an example of a change in the luminance in a visible light image, or in particular, a change in the luminance in green, according to the present embodiment. Specifically, FIG. 12A illustrates the change in the luminance of a green component (G) in the cheek region of the user U in the visible light image captured by the visible light imaging unit 102. In the graph illustrated in FIG. 12A, the horizontal axis represents the time, and the vertical axis represents the luminance of the green component (G). The change in the luminance illustrated in FIG. 12A reveals that the luminance changes periodically in association with the pulse wave.

In a usual environment, that is, in a case in which an image of the skin is captured in the visible light range, a visible light image includes noise associated with scattered light of illumination or a variety of causes. Therefore, the visible light waveform computing unit 105 may subject the visible light image acquired from the visible light imaging unit 102 to signal processing using a filter or the like and obtain a visible light image that includes a large amount of change in the luminance of the skin associated with the pulse wave. An example of the filter used in the signal processing is a low-pass filter. In other words, the visible light waveform computing unit 105 carries out extraction processing of a visible light waveform by using the change in the luminance of the green component (G) through a low-pass filter according to the present embodiment.

Figure 13A:
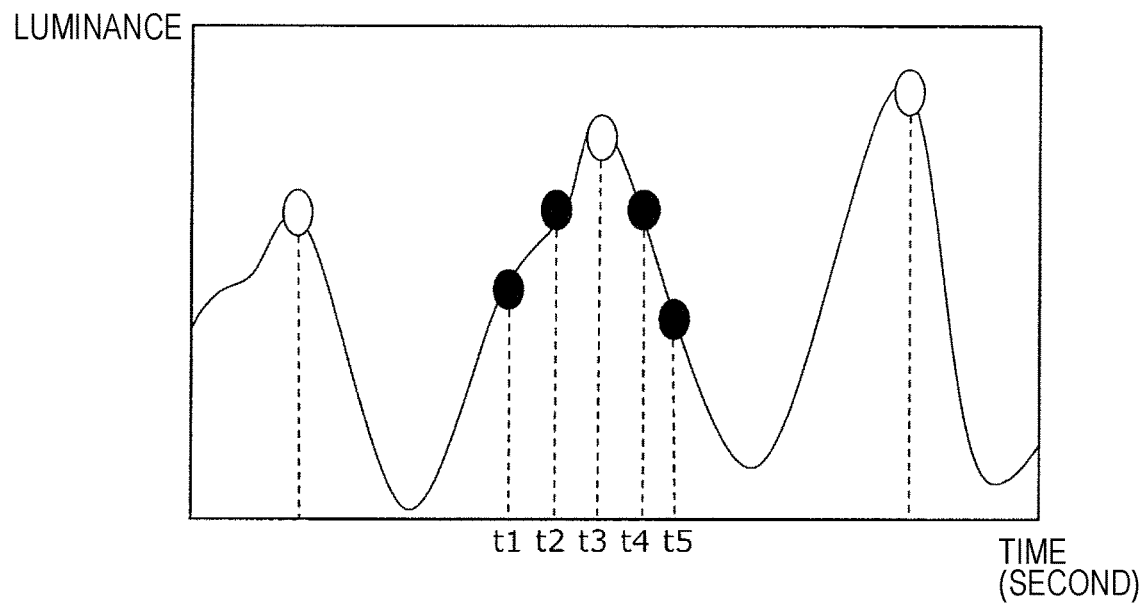
FIGS. 13A and 13B are graphs illustrating an example of a calculation of a pulse wave timing according to an embodiment.

FIG. 13A is a graph illustrating an example of the calculation of the pulse wave timing according to the present embodiment. In the graph illustrated in FIG. 13A, the horizontal axis represents the time, and the vertical axis represents the luminance. In the temporal waveform of the graph illustrated in FIG. 13A, points at respective time points t1 to t5 are each a point of inflection or a crest. The points on the temporal waveform of the graph include a point of inflection and a peak point (a crest and a trough) as feature points. A crest is a point with a maximum value in an upward displacement in the temporal waveform, and a trough is a point with a minimum value in a downward displacement in the temporal waveform. At each point described above included in the temporal waveform, the time point of a given point (crest) at which the luminance is higher than those of the points appearing temporally across the given point or the time point of a given point (trough) at which the luminance is lower than those of the points appearing temporally across the given point is the pulse wave timing.

With reference to the temporal waveform of the luminance in the graph illustrated in FIG. 13A, a method of identifying the position of a crest, or in other words, a method of searching for a peak will be described. The visible light waveform computing unit 105 sets a current reference point to the point at the time point t2 in the temporal waveform of the luminance. The visible light waveform computing unit 105 compares the point at the time point t2 and the point at the time point t1 preceding the time point t2 by one time point, and compares the point at the time point t2 and the point at the time point t3 following the time point t2 by one time point. When the luminance at the reference point is higher than the luminance of each of the point that precedes the point by one time point and the point that follows the point by one time point, the visible light waveform computing unit 105 makes a determination of true. In other words, in this case, the visible light waveform computing unit 105 determines that the reference point is a peak point (crest) and the time point of that reference point is a pulse wave timing.

On the other hand, when the luminance at the reference point is lower than the luminance of at least either of the point that precedes the point by one time point and the point that follows the point by one time point, the visible light waveform computing unit 105 makes a determination of false. In other words, in this case, the visible light waveform computing unit 105 determines that the reference point is not a peak point (crest) and the time point of the reference point is not a pulse wave timing.

Figure 13B:
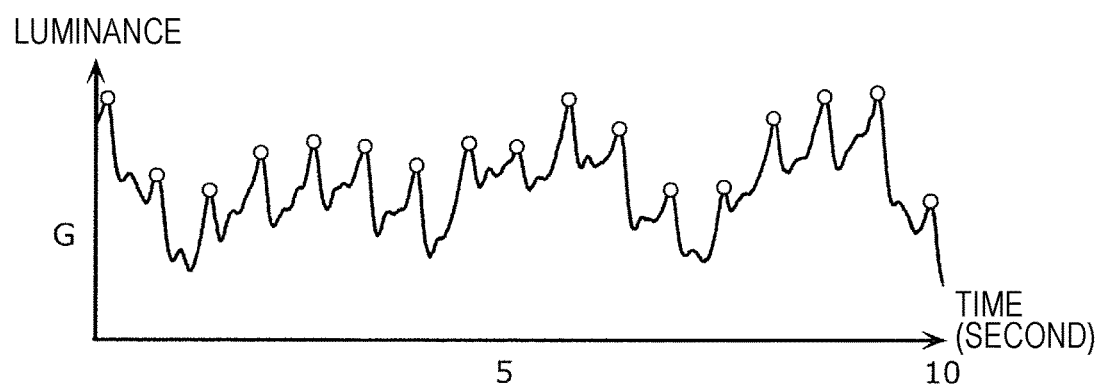

In FIG. 13A, the luminance at the point at the time point t2 is higher than the luminance at the point at the time point t1, but the luminance at the point at the time point t2 is lower than the luminance at the point at the time point t3. Thus, the visible light waveform computing unit 105 makes a determination of false for the point at the time point t2. Next, the visible light waveform computing unit 105 increments the reference point by one and sets the point at the following time point t3 as the reference point. The luminance at the point at the time point t3 is higher than the luminance at the point at the time point t2 preceding the time point t3 by one time point and the luminance at the point at the time point t4 following the time point t3 by one time point. Thus, the visible light waveform computing unit 105 makes a determination of true for the point at the time point t3. The visible light waveform computing unit 105 outputs, to the correlation degree computing unit 107, the time point of the point for which a determination of true has been made as a pulse wave timing. Thus, as illustrated in FIG. 13B, the time points with open circles are identified as the pulse wave timings.

When identifying the pulse wave timing, the visible light waveform computing unit 105 may identify the pulse wave timing in consideration of a feature that the heartbeat interval time falls, for example, between 333 ms and 1000 ms on the basis of the knowledge on a typical heart rate (e.g., from 60 bpm to 180 bpm). By taking the typical heartbeat interval time into consideration, the visible light waveform computing unit 105 does not need to carry out the comparison of the luminance as described above at every point and can identify an appropriate pulse wave timing by comparing the luminances at some of the points. In other words, the visible light waveform computing unit 105 may compare the luminances as described above by using, as the reference point, each of the points that fall within a range of from 333 ms to 1000 ms from a pulse wave timing acquired most recently. In this case, the visible light waveform computing unit 105 can identify a subsequent pulse wave timing without comparing the luminances by using a point preceding the stated range as the reference point. Therefore, a robust acquisition of pulse wave timings in a usual environment can be achieved.

Furthermore, the visible light waveform computing unit 105 calculates the heartbeat interval time by calculating the time difference between obtained pulse wave timings that are adjacent to each other. The heartbeat interval time varies in time series. Therefore, by comparing the stated heartbeat interval time with the heartbeat interval time of the pulse wave identified from the infrared light waveform acquired in the same time period, the result can be used to compute the degree of correlation between a predetermined feature point in the visible light waveform and a predetermined feature point in the infrared light waveform.

Figure 14:
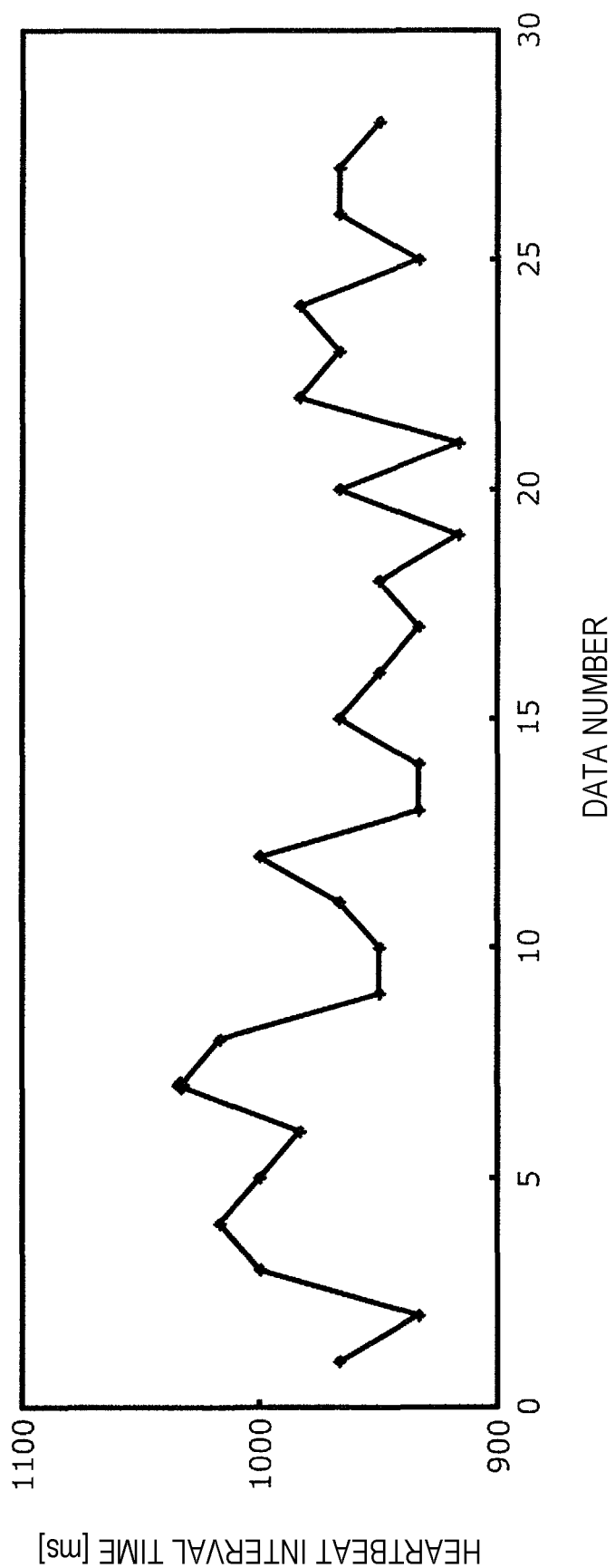
FIG. 14 is a graph illustrating an example of a heartbeat interval time acquired in time series.

FIG. 14 is a graph illustrating an example of a heartbeat interval time acquired in time series. In the graph illustrated in FIG. 14, the horizontal axis represents the data number associated with the heartbeat interval time acquired in time series, and the vertical axis represents the heartbeat interval time. FIG. 14 reveals that the heartbeat interval time varies depending on the time point. The data number indicates the order in which the pieces of data (here, the heartbeat interval times) are stored in the memory. In other words, the data number corresponding to the heartbeat interval time stored in an n-th order (n is a natural number) is "n."

Furthermore, the visible light waveform computing unit 105 may extract the time point of a point of inflection immediately after a pulse wave timing in the visible light waveform. Specifically, the visible light waveform computing unit 105 acquires a minimum point of the visible light differential luminance by calculating a first derivative of the luminance value of the visible light waveform and calculates the time point of the minimum point as the time point of the point of inflection (hereinafter, referred to as an inflection point timing). In other words, the visible light waveform computing unit 105 may extract a plurality of points of inflection between a crest and a trough as predetermined feature points.

When calculating the inflection point timing as well, the visible light waveform computing unit 105 may calculate the inflection point timing in consideration of a feature that the heartbeat interval time falls, for example, between 333 ms and 1000 ms on the basis of the knowledge on a typical heart rate. Thus, even when a point of inflection completely unrelated to the heartbeat is included in the visible light waveform, this point of inflection is not identified, and thus the inflection point timing can be calculated more accurately.

Figure 15A:
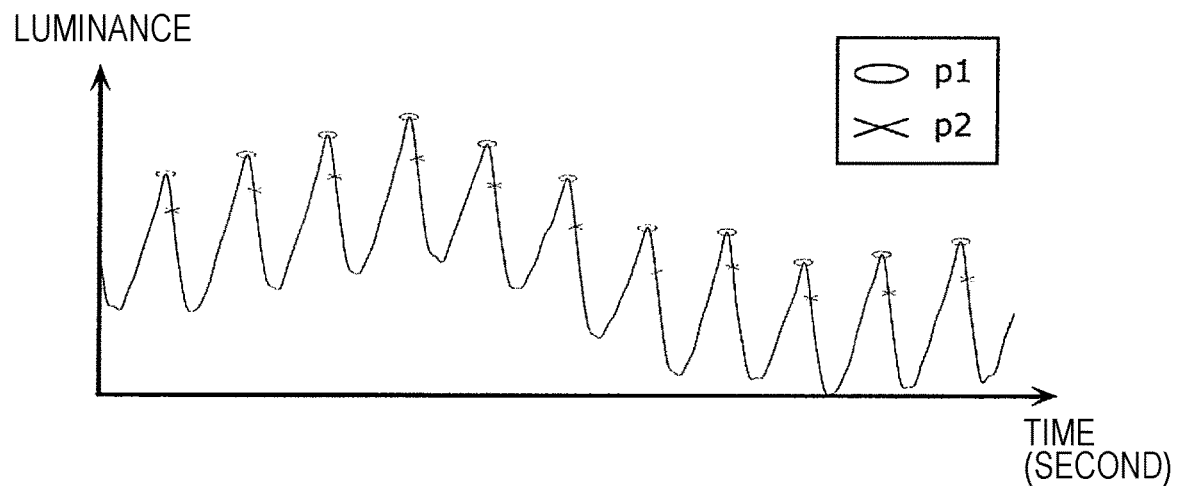
FIGS. 15A and 15B are graphs for describing a method of extracting a point of inflection from a pulse wave.
Figure 15B:
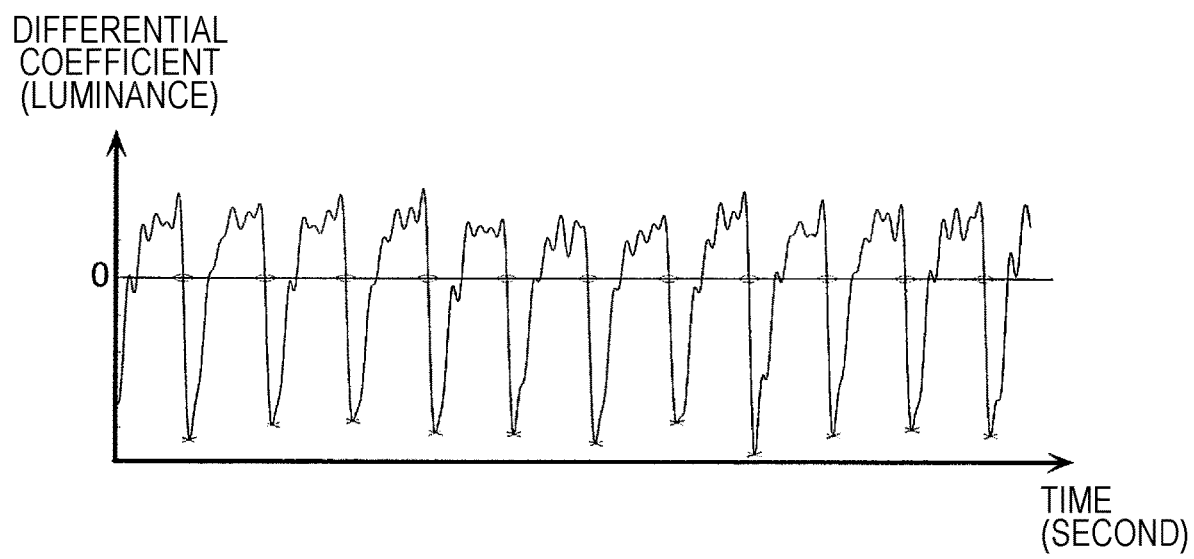

FIGS. 15A and 15B are graphs for describing a method of extracting a point of inflection from the pulse wave. Specifically, FIG. 15A is a graph illustrating a visible light waveform obtained from a visible light image, and FIG. 15B is a graph on which first derivatives are plotted. In FIG. 15A, the circles indicate the crests among the peak points, and the crosses indicate the points of inflection. In FIG. 15B, the circles indicate the points corresponding to the crests indicated in FIG. 15A, and the crosses indicate the points corresponding to the points of inflection indicated in FIG. 15A. In the graph illustrated in FIG. 15A, the horizontal axis represents the time, and the vertical axis represents the luminance value. In the graph illustrated in FIG. 15B, the horizontal axis represents the time, and the vertical axis represents the differential coefficient of the luminance value.

To extract the visible light waveform, in particular, a visible light image in which an image of green light is captured is used as described above. The principle of the extraction of this visible light waveform will be described. When the amount of blood in a blood vessel of a face, a hand, or the like increases or decreases in accordance with a pulse wave, the amount of hemoglobin in the blood increases or decreases in accordance with the amount of blood. In other words, the amount of hemoglobin that absorbs light in the wavelength range of green increases or decreases in accordance with an increase or a decrease in the amount of blood in the blood vessel. Therefore, in the visible light image captured by the visible light imaging unit 102, the color of the skin in the vicinity of a blood vessel changes in accordance with an increase or a decrease in the amount of blood, and the luminance value of, in particular, the green component of the visible light changes. Specifically, since hemoglobin absorbs green light, the luminance value in the visible light image decreases by the amount absorbed by hemoglobin.

Furthermore, the visible light waveform has characteristics that the gradient from a trough to a crest is less steep than the gradient from the crest to a subsequent trough. Therefore, an influence of noise is relatively greater in a segment from a trough to a crest. On the other hand, since the gradient is steep in a segment from the crest to a subsequent trough, an influence of noise is smaller. Therefore, an inflection point timing present in a segment from a crest to a trough is less prone to an influence of noise and can be acquired relatively stably. On the basis of the above, the visible light waveform computing unit 105 may calculate the time difference between the points of inflection present in a segment from a crest to a trough as the heartbeat interval time.

In addition, the peak point in the visible light waveform described above is a portion at which the differential coefficient becomes zero immediately before a point of inflection. Specifically, as illustrated in FIG. 15B, it can be seen that the time point of the point at which the differential coefficient immediately preceding a cross serving as a point of inflection becomes zero is the time point with a circle indicating a crest in FIG. 15A. With the use of this feature, the visible light waveform computing unit 105 may limit a crest to be acquired from the visible light waveform to a crest immediately preceding a point of inflection.

Furthermore, the visible light waveform computing unit 105 calculates the slope from a crest to a trough of the visible light waveform. In other words, the visible light waveform computing unit 105 calculates the slope from a crest to a trough in a waveform within one cycle of the pulse wave of the user U defined by the heartbeat interval time in the visible light waveform. It is preferable that the slope be greater. A reason for this is that, as the slope is greater, the kurtosis of the crest in the visible light waveform increases, and the temporal deviation in the pulse wave timing associated with filter processing or the like decreases.

Figure 16:
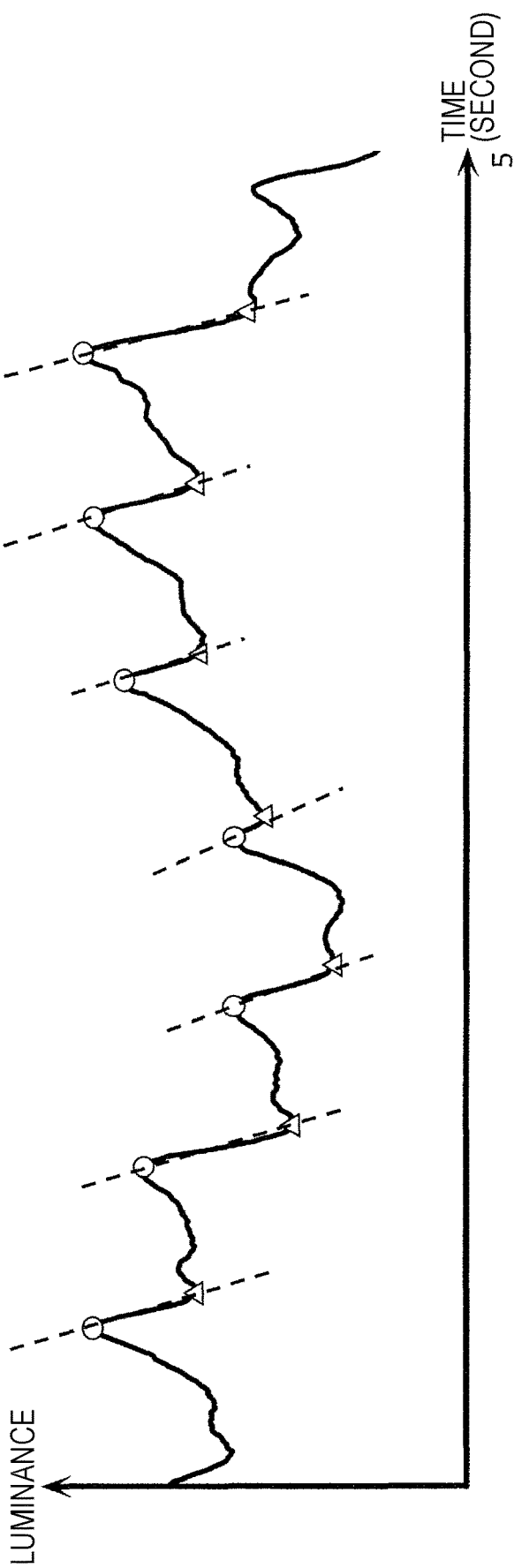
FIG. 16 is a graph illustrating a visible light waveform for describing a method of computing the slope from a crest to a trough in the visible light waveform.

FIG. 16 is a graph illustrating a visible light waveform for describing a method of computing the slope from a crest to a trough in the visible light waveform. In the graph illustrated in FIG. 16, the horizontal axis represents the time, and the vertical axis represents the luminance value, in which the circles indicate the crests and the triangles indicate the troughs. The visible light waveform computing unit 105 connects a crest (circle) to a trough (triangle) following the crest with a straight line and calculates the slope of that straight line. The calculated slope differs in accordance with the quantity of light emitted by a light source in the visible light source 101, the site on the skin of the user U captured by the visible light imaging unit 102, and so on. Therefore, the quantity of light of the visible light source 101 and the ROI corresponding to the site on the user U in the visible light imaging unit 102 are each set such that the pulse wave can be acquired clearly, or for example, such that the heartbeat interval time can continue to be acquired from 333 ms to 1000 ms, and the slope information is recorded to allow the slope information to be compared with the slope information of the infrared light pulse wave. In addition, the visible light waveform computing unit 105 records, as a first slope A, the slope from a crest to a trough in the visible light waveform in an initial state, or in other words, in a state in a period from when the visible light source 101 is turned ON to when the quantity of light of the visible light of the visible light source 101 or the quantity of light of the infrared light of the infrared light source 104 is changed by the light source controlling unit 108 into a memory. The pulse wave measuring apparatus 140 gradually brings the quantity of light of the visible light source 101 to zero and gradually increases the quantity of light of the infrared light source 104 while comparing the feature points in the visible light waveform and the infrared light waveform. In this manner, since the quantity of light of the visible light is reduced gradually, the slope from a crest to a trough in the visible light waveform is greatest in the initial state.

Infrared Light Waveform Computing Unit 106

The infrared light waveform computing unit 106 acquires an infrared light image from the infrared light imaging unit 103 and extracts an infrared light waveform, which is a waveform that indicates the pulse wave of the user U, from the acquired infrared light image. The infrared light waveform computing unit 106 may extract a plurality second feature points, which are predetermined feature points in the extracted infrared light waveform. The predetermined feature point is, for example, a peak point, which is a crest or a trough, in a waveform within one cycle of the pulse wave of the user U.

In a similar manner to the visible light waveform computing unit 105, the infrared light waveform computing unit 106 acquires the timing of the pulse wave as a feature point of the infrared light waveform and computes the heartbeat interval time from the timings of adjacent pulse waves. In other words, the infrared light waveform computing unit 106 calculates, for each of the plurality of extracted second feature points, the time between a given second feature point and another second feature point adjacent to the given second feature point as a second heartbeat interval time. Specifically, the infrared light waveform computing unit 106 extracts an infrared light waveform on the basis of the change over time in the luminance extracted from a plurality of infrared light images. In other words, each of the plurality of infrared light images acquired from the infrared light imaging unit 103 is associated with a time point at which the infrared light image has been captured in the infrared light imaging unit 103. The infrared light waveform computing unit 106 acquires the pulse wave timing of the user U by acquiring the interval of predetermined feature points in the infrared light waveform. Then, the infrared light waveform computing unit 106 calculates, for each of the plurality of obtained pulse wave timings, the interval between a given pulse wave timing and another pulse wave timing following the given pulse wave timing as the heartbeat interval time.

Here, the infrared light waveform computing unit 106 can identify the peak position serving as the predetermined feature point in the infrared light waveform, in a similar manner to the visible light waveform computing unit 105, by using, for example, a well-known local search method including a method that employs hill climbing, autocorrelation, and a differential function.

Typically, in an infrared light image, in a similar manner to a visible light image, the luminance of the skin region, such as a face or a hand, in the image changes depending on the amount of components in blood, such as hemoglobin. In other words, information pertaining to the movement of the blood can be acquired by using the change over time in the luminance of the face or a hand obtained from the images of the face or the hand captured at a plurality of timings. In this manner, the infrared light waveform computing unit 106 acquires the pulse wave timing by computing the information pertaining to the movement of the blood from the plurality of images captured in time series.

To acquire the pulse wave timing in the infrared light range, the image that captures the luminance in the wavelength range of no less than 800 nm in the infrared light image may be used. In the image captured in the infrared light range, the change associated with the pulse wave appears prominently in the luminance in the wavelength range of from around 800 nm to 950 nm.

Figure 12B:
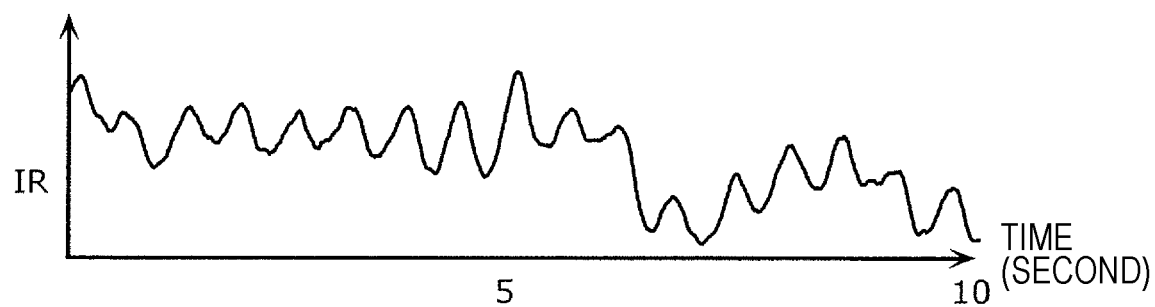

FIG. 12B is a graph illustrating an example of a change in the luminance in an infrared light image according to the present embodiment. Specifically, FIG. 12B illustrates the change in the luminance in the cheek region of the user U in the infrared light image captured by the infrared light imaging unit 103. In the graph illustrated in FIG. 12B, the horizontal axis represents the time, and the vertical axis represents the luminance. The change in the luminance illustrated in FIG. 12B reveals that the luminance changes periodically in association with the pulse wave.

However, when an image of the skin is captured in the infrared light range, the amount of infrared light absorbed by hemoglobin is small, as compared to the case in which an image of the skin is captured in the visible light range. In other words, an infrared light image captured in the infrared light range is more likely to include noise resulting from a variety of causes such as the body movement. Therefore, by subjecting the captured infrared light image to signal processing using a filter or the like and by irradiating the skin region of the user U with infrared light of an appropriate quantity of light, an infrared light image that includes a large amount of change in the luminance of the skin resulting from the pulse wave may be obtained. An example of the filter used in the signal processing is a low-pass filter. In other words, the infrared light waveform computing unit 106 carries out extraction processing of an infrared light waveform by using the change in the luminance of the infrared light that has passed through a low-pass filter according to the present embodiment. A method of determining the quantity of light of the infrared light from the infrared light source 104 will be described along with the correlation degree computing unit 107 or the light source controlling unit 108.

Next, a method of searching for a peak by the infrared light waveform computing unit 106 will be described. To search for a peak in an infrared light waveform, a method similar to the method of searching for a peak in a visible light waveform can be used.

When identifying the pulse wave timing, in a similar manner to the visible light waveform computing unit 105, the infrared light waveform computing unit 106 may identify the pulse wave timing in consideration of a feature that the heartbeat interval time falls, for example, between 333 ms and 1000 ms on the basis of the knowledge on a typical heart rate (e.g., from 60 bpm to 180 bpm). By taking the typical heartbeat interval time into consideration, the infrared light waveform computing unit 106 does not need to carry out the comparison of the luminance as described above at every point and can identify an appropriate pulse wave timing by comparing the luminances at some of the points. In other words, the infrared light waveform computing unit 106 may compare the luminances as described above by using, as the reference point, each of the points that fall within a range of from 333 ms to 1000 ms from a pulse wave timing acquired most recently. In this case, the infrared light waveform computing unit 106 can identify the subsequent pulse wave timing without comparing the luminances by using a point preceding the stated range as the reference point.

In a similar manner to the visible light waveform computing unit 105, the infrared light waveform computing unit 106 calculates the heartbeat interval time by calculating the time difference between obtained pulse wave timings that are adjacent to each other. Furthermore, the infrared light waveform computing unit 106 may extract the time point of the point of inflection immediately following the pulse wave timing in the infrared light waveform. Specifically, the infrared light waveform computing unit 106 acquires a minimum point of the infrared light differential luminance by calculating a first derivative of the luminance value of the infrared light waveform and calculates the time point of the minimum point as the time point of the point of inflection (inflection point timing). In other words, the infrared light waveform computing unit 106 may extract a plurality of points of inflection between a crest and a trough as predetermined feature points.

In addition, in a similar manner to the visible light waveform computing unit 105, the infrared light waveform computing unit 106 computes the slope from a crest to a trough of the infrared light waveform.

As described thus far, the infrared light waveform computing unit 106 extracts a plurality of second feature points as predetermined feature points by carrying out similar processing to the visible light waveform computing unit 105. However, as compared to the visible light waveform, the infrared light waveform changes greatly depending on the quantity of light of the infrared light emitted by a light source. In other words, the infrared light waveform is more prone to an influence of the quantity of light of the light source than the visible light waveform.

Figure 17A:
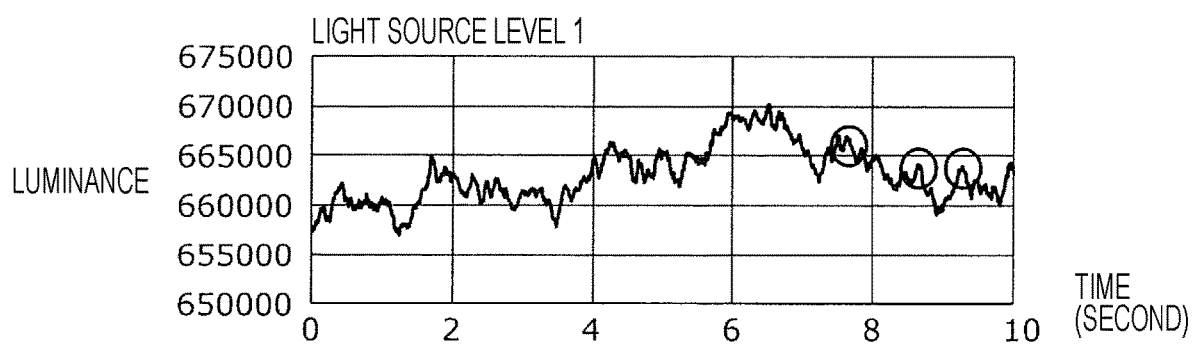
FIGS. 17A, 17B, 17C, and 17D are graphs illustrating an infrared light waveform of a case in which a skin image of a person is acquired with an infrared light camera with the level of the quantity of light of an infrared light source being varied.
Figure 17B:
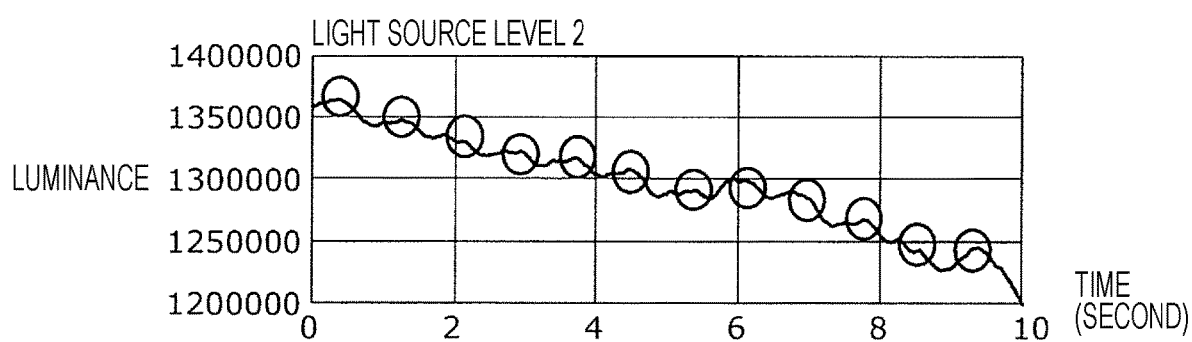
Figure 17C:
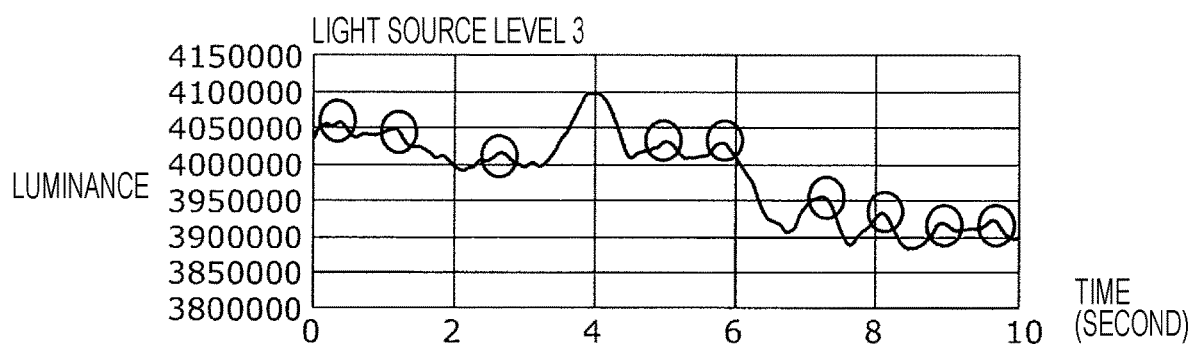
Figure 17D:
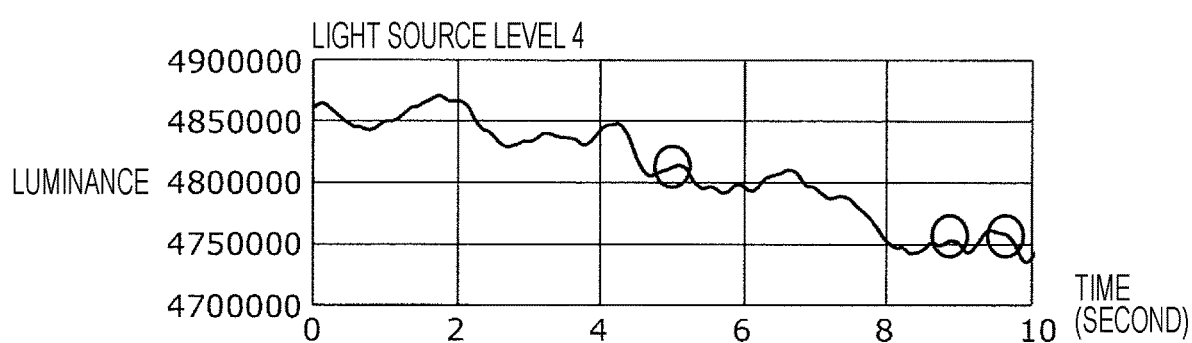

FIGS. 17A to 17D are graphs illustrating an infrared light waveform obtained in a case in which an image of the skin of a person is acquired by an infrared light camera with the level of the quantity of light of the infrared light source being varied. In FIGS. 17A to 17D, the level of the quantity of light of the infrared light source is increased successively from FIG. 17A to FIG. 17D. In other words, the light source level indicates that the quantity of light is smallest at the light source level 1, the quantity of light increases as the light source level increases, and the quantity of light is largest at the light source level 4. The light source level indicates that the control voltage of the light source increases by approximately 0.5 V as the level increases by one. The circles in each of the graphs in FIGS. 17A to 17D indicate the peak positions (crests) of the pulse wave. As illustrated in FIG. 17A, when the quantity of light at the light source is small, noise dominates over the infrared light from the infrared light source, which makes it difficult to identify the pulse wave timing. Meanwhile, as illustrated in FIG. 17C and FIG. 17D, when the quantity of light at the light source is large, the change in the luminance of the skin corresponding to the pulse wave is buried in the quantity of light, and the shape of the pulse wave becomes small, which makes it difficult to identify the pulse wave timing.

When the pulse wave is to be acquired by using an image captured in the visible light range by irradiating with visible light, even if the user U is irradiated with visible light at the quantity of light that is not too large for the eyes of the user U, the pulse wave can be acquired sufficiently with that irradiation amount. However, when the pulse wave is to be acquired by using an image captured in the infrared light range by irradiating with infrared light, even if the quantity of light of the infrared light is controlled, noise may be included, or the quantity of light of the infrared light may become too large, as described above. Therefore, it is difficult to acquire the pulse wave outside a fairly limited range of the quantity of light. In addition, even if the quantity of light of the infrared light source is set to a predetermined value in advance, the quantity of light changes depending on the site on the skin to be acquired and/or the skin type, the skin color, or the like of the user U, and thus it is difficult to determine an appropriate quantity of light in advance. Therefore, control needs to be carried out by the correlation degree computing unit 107, which will be described next, such that the quantity of light of the infrared light becomes an appropriate value while the quantity of light of the visible light is regulated so that the visible light waveform and the infrared light waveform coincide with each other.

Correlation Degree Computing Unit 107

The correlation degree computing unit 107 computes the degree of correlation between the visible light waveform obtained from the visible light waveform computing unit 105 and the infrared light waveform obtained from the infrared light waveform computing unit 106. Then, the correlation degree computing unit 107 determines an instruction for adjusting the quantity of light of the visible light source 101 and the quantity of light of the infrared light source 104 in accordance with the calculated degree of correlation and transmits the determined instruction to the light source controlling unit 108.

The correlation degree computing unit 107 acquires, as the feature amounts, a plurality of first heartbeat interval times calculated from the visible light waveform and a plurality of second heartbeat interval times calculated from the infrared light waveform from the visible light waveform computing unit 105 and the infrared light waveform computing unit 106, respectively. Then, the correlation degree computing unit 107 computes the degree of correlation between the plurality of first heartbeat interval times and the plurality of second heartbeat interval times that correspond to each other in time series.

Figure 18:
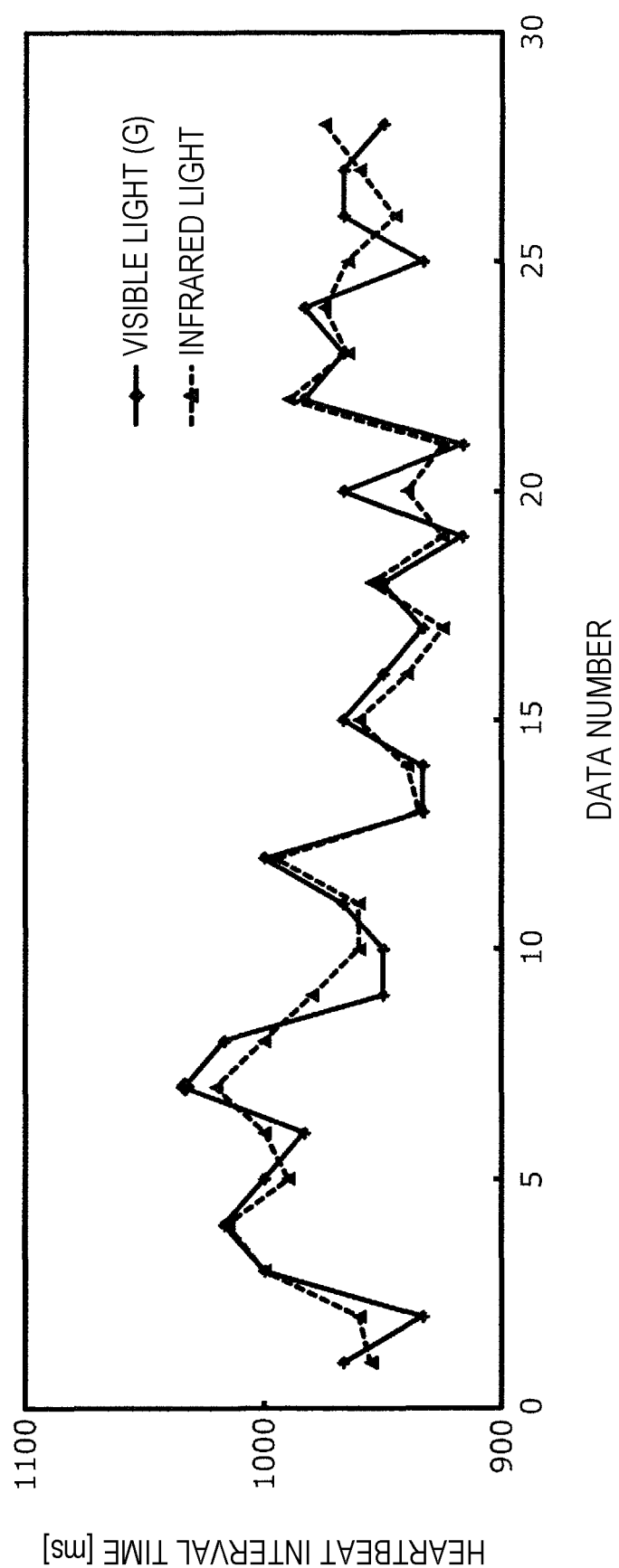
FIG. 18 is a graph in which data of a first heartbeat interval time and data of a second heartbeat interval time are plotted in time series.

FIG. 18 is a graph in which the data of the first heartbeat interval times and the data of the second heartbeat interval times are plotted in time series. In the graph illustrated in FIG. 18, the horizontal axis represents the data number in time series, and the vertical axis represents the heartbeat interval times corresponding to the respective data numbers. The data number indicates the order in which the data of the heartbeat interval times is stored into the memory. In other words, in the first heartbeat interval times, the data number corresponding to the heartbeat interval time stored at an n-th order (n is a natural number) is "n." In addition, in the second heartbeat interval times, the data number corresponding to the heartbeat interval time stored at an n-th order (n is a natural number) is "n." Furthermore, since the first heartbeat interval times and the second heartbeat interval times are the results obtained by measuring the pulse waves at the same timing, as a general rule, unless there is a measurement error, the pieces of data with the same data number are the results obtained by measuring the pulse waves at substantially the same timing. In other words, the plurality of first heartbeat interval times and the plurality of second heartbeat interval times include a pair of a first heartbeat interval time and a second heartbeat interval time that correspond to each other in time series.

The correlation degree computing unit 107 computes the degree of correlation between the plurality of first heartbeat interval times and the plurality of second heartbeat interval times by using a correlation method. The correlation degree computing unit 107, for example, determines that the plurality of first heartbeat interval times and the plurality of second heartbeat interval times substantially coincide with each other if the correlation coefficient serving as the degree of correlation is no less than a second threshold value, which is 0.8, for example, and transmits, to the light source controlling unit 108, a "TRUE" signal, for example, as a signal indicating that the plurality of first heartbeat interval times and the plurality of second heartbeat interval times substantially coincide with each other. On the other hand, the correlation degree computing unit 107 determines that the plurality of first heartbeat interval times and the plurality of second heartbeat interval times do not coincide with each other if the correlation coefficient is less than the second threshold value, which is 0.8, for example, and transmits, to the light source controlling unit 108, a "FALSE" signal, for example, as a signal indicating that the plurality of first heartbeat interval times and the plurality of second heartbeat interval times do not coincide with each other.

In addition, the correlation degree computing unit 107 determines whether the degree of correlation between the first heartbeat interval times and the second heartbeat interval times is appropriate, also determines whether each of the heartbeat interval times is appropriate, and transmits the determination results to the light source controlling unit 108. Specifically, the correlation degree computing unit 107 determines whether an absolute error between a first heartbeat interval time and a second heartbeat interval time that correspond to each other in time series, among the plurality of first heartbeat interval times and the plurality of second heartbeat interval times, exceeds a third threshold value (e.g., 200 ms). The correlation degree computing unit 107, for example, calculates the absolute error between the first heartbeat interval time and the second heartbeat interval time that have the same data number and determines whether the absolute error exceeds the third threshold value. Then, the correlation degree computing unit 107 determines that there are an excess number of peak points in either of the visible light waveform and the infrared light waveform if, for example, it is determined that the absolute error exceeds the third threshold value. Then, the correlation degree computing unit 107 transmits, to the light source controlling unit 108, the waveform that includes an excess number of peak points (the visible light waveform or the infrared light waveform). The absolute error is computed through the following expression (1).

$$e = RRI_{RGB} - RRI_{IR} \tag{1}$$

In the expression (1), e represents the absolute error between a first heartbeat interval time and a corresponding second heartbeat interval time, $RRI_{RGB}$ represents the first heartbeat interval time, and $RRI_{IR}$ represents the second heartbeat interval time.

In addition, the correlation degree computing unit 107 determines that there are an excess number of peak points in the visible light if e is smaller than (−1)×the third threshold value (e.g., −200 ms) and determines that there is an excess number of peak points in the infrared light if e is greater than the third threshold value (e.g., 200 ms). Then, the correlation degree computing unit 107 transmits, to the light source controlling unit 108, information indicating whether the waveform that includes an excess number of peak points is the visible light waveform or the infrared light waveform as the determination result. In this manner, in which waveform an excess number of peak points have been acquired or acquisition of a peak point has failed can be identified from a mismatch between the heartbeat interval times corresponding to the two waveforms.

The correlation degree computing unit 107 transmits a "False, RGB" signal indicating the result of the determination to the light source controlling unit 108 if, for example, it is determined that the absolute error between a first heartbeat interval time and a corresponding second heartbeat interval time exceeds the third threshold value and an excess number of peak points have been acquired in the visible light waveform. The correlation degree computing unit 107 transmits a "False, IR" signal indicating the result of the determination to the light source controlling unit 108 if it is determined that the absolute error exceeds the third threshold value and an excess number of peak points have been acquired in the infrared light waveform.

Figure 19A:
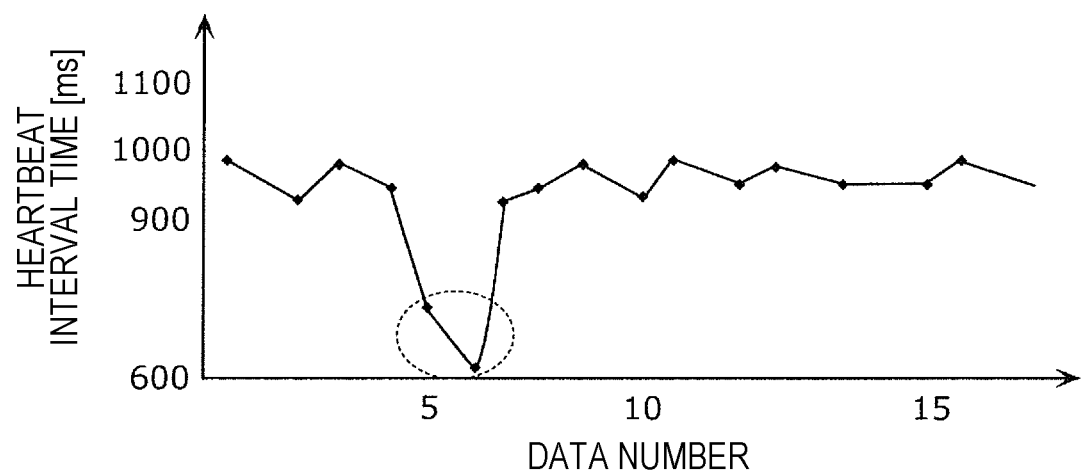
FIGS. 19A and 19B are illustrations for describing a specific example of a determination as to whether a heartbeat interval time is appropriate.
Figure 19B:
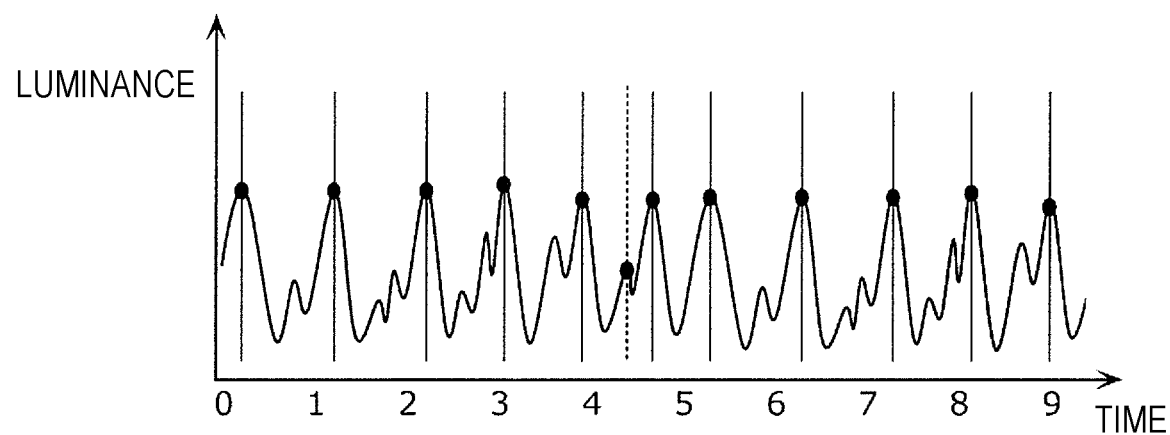

FIGS. 19A and 19B are illustrations for describing a specific example of determining whether a heartbeat interval time is appropriate. FIG. 19A is a graph illustrating a case in which a plurality of acquired heartbeat interval times are not appropriate. FIG. 19B, which corresponds to FIG. 19A, is a graph illustrating an example of a visible light waveform or an infrared light waveform. In the graph illustrated in FIG. 19A, the horizontal axis represents the data number in time series, and the vertical axis represents the heartbeat interval times corresponding to the respective data numbers. In the graph illustrated in FIG. 19B, the horizontal axis represents the time, and the vertical axis represents the luminance in the image.

In FIG. 19A, the two heartbeat interval times enclosed by a dotted line correspond to a portion that is not appropriate. Although the heartbeat interval time typically varies with fluctuations, the value of the heartbeat interval time rarely varies sharply. For example, in a region outside the portion enclosed by the dotted line as illustrated in FIG. 19A, the mean value is approximately 950 ms, and the variance is approximately 50 ms. However, the values of the two heartbeat interval times enclosed by the dotted line sharply change to approximately 600 ms to 700 ms. This occurs because the portion indicated by the dashed line in FIG. 19B is acquired as a peak point. In other words, this occurs because an excess number of peak points have been acquired in the visible light waveform computing unit 105 or the infrared light waveform computing unit 106.

When the result such as the one illustrated in FIGS. 19A and 19B is obtained in either the visible light waveform computing unit 105 or the infrared light waveform computing unit 106, a comparison between the number of pieces of data in the plurality of first heartbeat interval times and the number of pieces of data in the plurality of second heartbeat interval times leads to a mismatch in the number of pieces of data.

Figure 20:
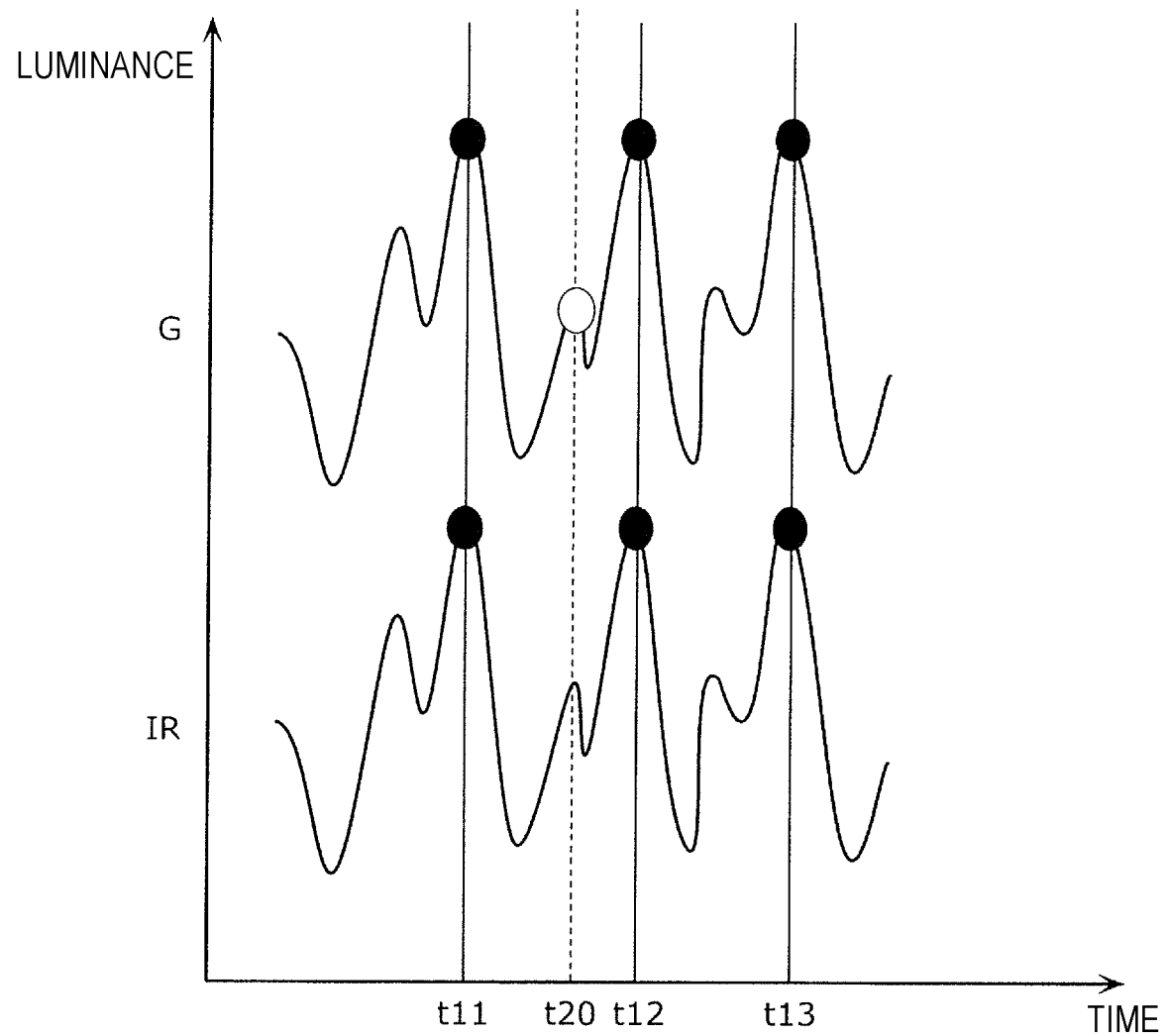
FIG. 20 is an illustration for describing an example of a case in which an excess number of peak points are acquired in a visible light waveform but the peak points are not acquired in excess in a corresponding infrared light waveform.

FIG. 20 illustrates this situation. FIG. 20 is an illustration for describing an example of a case in which an excess number of peak points are acquired in a visible light waveform but the peak points are not acquired in excess in a corresponding infrared light waveform.

The data of the plurality of first or second heartbeat interval times is stored, for example, in the format of (data No., heartbeat interval time). The pieces of data representing the plurality of first heartbeat interval times acquired in a visible light waveform are, for example, (x, t20−t11), (x+1, t12−t20), and (x+2, t13−t12). The pieces of data representing the plurality of second heartbeat interval times acquired in an infrared light waveform are, for example, (x, t12−t11) and (x+1, t13−t12). Thus, when the data acquired in the visible light waveform and the data acquired in the infrared light waveform are compared with each other, the numbers of pieces of data differ although both data are acquired in the same time period of from t11 to t13. Thus, the correspondence relationship between the data of the first heartbeat interval times and the data of the second heartbeat interval times is all mismatched thereafter, and the degree of correlation of the changes over time in the heartbeat interval times becomes inappropriate.

Therefore, when the absolute error of the heartbeat interval times in the data numbers of the first heartbeat interval times and the second heartbeat interval times obtained by the visible light waveform computing unit 105 and the infrared light waveform computing unit 106, respectively, is no less than the third threshold value, which is 200 ms, for example, the correlation degree computing unit 107 deletes one pulse wave peak from the data having a greater number of peak points. Then, the correlation degree computing unit 107 carries out processing of subtracting one from each of the data numbers following the data number corresponding to the deleted peak.

In other words, when it has been determined that an excess number of peak points (i.e., predetermined feature points) have been acquired as described above, the correlation degree computing unit 107 may exclude a predetermined feature point that has served as a reference for computing the heartbeat interval time in a waveform having a larger number of predetermined feature points (a visible light waveform or an infrared light waveform) from a computation target of the heartbeat interval time. In other words, when e is smaller than (−1)×the third threshold value, the correlation degree computing unit 107 excludes the peak point that has served as a reference for computing $RRI_{RGB}$ used to calculate the stated e from the computation target of the first heartbeat interval time. When e is greater than the third threshold value, the correlation degree computing unit 107 excludes the peak point that has served as a reference for computing $RRI_{IR}$ used to calculate the stated e from the computation target of the second heartbeat interval time.

In addition, an excess number of peak points are acquired because an acquired waveform (visible light waveform or infrared light waveform) includes a large amount of noise. Therefore, it is determined whether the waveform that includes an excess number of acquired peak points is a visible light waveform or an infrared light waveform, a signal such as the "FALSE, RGB" signal described above is generated, for example, and the generated signal is transmitted to the light source controlling unit 108. In other words, if the light source controlling unit 108 receives the "FALSE, RGB" signal, the light source controlling unit 108 can determine that the heartbeat interval times do not match between the visible light waveform and the infrared light waveform and that the waveform causing this mismatch is the visible light waveform. In this manner, a mismatch between the data for acquiring the peak points in the visible light waveform and the data for acquiring the infrared light waveform can be found, and the information indicating the result of the finding can be transmitted to the light source controlling unit 108. Thus, the pulse wave of the user U in the visible light waveform and the infrared light waveform can be acquired more accurately.

Although the correlation degree computing unit 107 determines the degree of correlation between the first heartbeat interval times and the second heartbeat interval times with the second threshold value set to 0.8, this is not a limiting example. Specifically, the second threshold value may be changed in accordance with the accuracy of the biometric information to be measured by the user U. For example, in a case in which the user U wants to acquire more accurate biometric information, including information on the heartbeat and/or the blood pressure, during sleep by extracting the exact pulse wave with infrared light while the user U is sleeping, the second threshold value that serves as the determination reference may be increased to, for example, 0.9 or the like.

In addition, when the second threshold value of the correlation coefficient that serves as a reference is adjusted, the reliability of the acquired data corresponding to the adjusted second threshold value may be displayed on the information presentation unit 110. For example, when the feature amounts do not easily match between the visible light waveform and the infrared light waveform and when the quantity of light from a light source for visible light cannot be reduced while sleeping or the like, the second threshold value of the correlation coefficient serving as a reference may be changed to a value smaller than 0.8, such as 0.6 or the like. In this case, the accuracy related to the degree of correlation is lowered, and thus the information presentation unit 110 may display information indicating that the reliability has decreased.

When the correlation coefficient of the first and second heartbeat interval times acquired from the visible light waveform and the infrared light waveform in time series is smaller than the second threshold value or when an excess number of peak points in a first predetermined time period are acquired in the visible light waveform computing unit 105 and the infrared light waveform computing unit 106, the correlation degree computing unit 107 may determine the degree of correlation between the visible light waveform and the infrared light waveform by using a point of inflection in each of the visible light waveform and the infrared light waveform. Specifically, as described above, when the correlation coefficient of the first and second heartbeat interval times in the visible light waveform and the infrared light waveform is smaller than the second threshold value, which is 0.8, for example, or when the numbers of the peak points acquired in the visible light waveform computing unit 105 and in the infrared light waveform computing unit 106 do not match in a first predetermined segment (e.g., five seconds) and the number of the peak points in at least one of the waveforms exceeds a first threshold value (e.g., 10), the correlation degree computing unit 107 may determine the degree of correlation of the time interval information between the points of inflection in the respective waveforms by using the points of inflection in the two waveforms of the visible light waveform and the infrared light waveform.

In other words, the correlation degree computing unit 107 determines whether the number of the peak points in the visible light waveform or the infrared light waveform exceeds the first threshold value in the first predetermined time period. When it is determined that the number of the stated peak points exceeds the first threshold value in the first predetermined time period, the correlation degree computing unit 107 may carry out the following processing. Specifically, the correlation degree computing unit 107 causes the visible light waveform computing unit 105 to extract, as first feature points, a plurality of points of inflection from a crest to a trough in the visible light waveform. The correlation degree computing unit 107 causes the infrared light waveform computing unit 106 to extract, as second feature points, a plurality points of inflection from a crest to a trough in the infrared light waveform. In addition, the correlation degree computing unit 107 causes the visible light waveform computing unit 105 to calculate, for each of the plurality of extracted first feature points, the time between a given first feature point and another first feature point adjacent to the given first feature point as the first heartbeat interval time. In addition, the correlation degree computing unit 107 causes the infrared light waveform computing unit 106 to calculate, for each of the plurality of extracted second feature points, the time between a given second feature point and another second feature point adjacent to the given second feature point as the second heartbeat interval time. Then, the correlation degree computing unit 107 computes, as the degree of correlation, the degree of correlation between the plurality of first heartbeat interval times and the plurality of second heartbeat interval times that correspond to each other in time series.

Figure 21A:
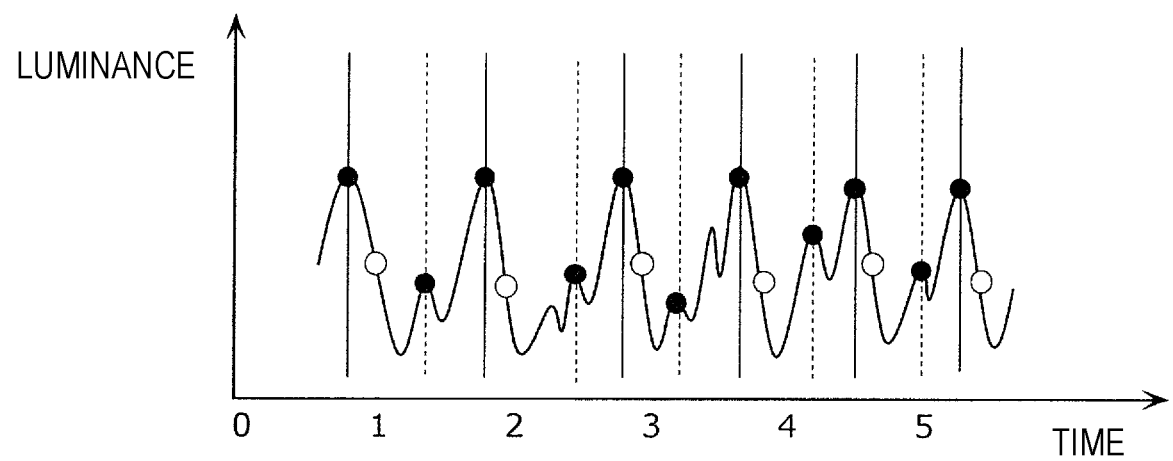
FIGS. 21A and 21B are illustrations for describing a case in which the degree of correlation is calculated by using a point of inflection.
Figure 21B:
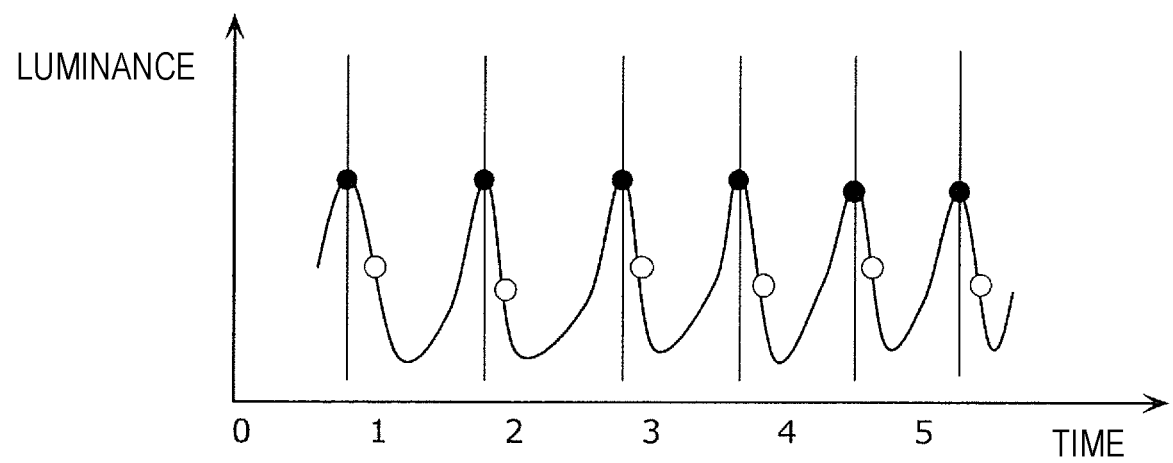

FIGS. 21A and 21B are illustrations for describing a case in which the degree of correlation is calculated by using a point of inflection. FIG. 21A is a graph illustrating peak points (crests) acquired in a visible light waveform, and FIG. 21B is a graph illustrating peak points (crests) acquired in an infrared light waveform. In both FIG. 21A and FIG. 21B, the horizontal axis represents the time, the vertical axis represents the luminance, the solid circles represent the acquired crests, and the open circles represent the acquired points of inflection.

FIG. 21A reveals that an excess number of peak points are acquired in the visible light waveform and there are ten or eleven peak points in the first predetermined time period (five seconds)-these numbers are equal to or greater than the first threshold value. Meanwhile, in FIG. 21B, the peak points are acquired at a constant heartbeat interval time in the infrared light waveform, and the variance is no greater than 100 ms. In this case, there arises a mismatch in the data numbers of time series indicating the first and second heartbeat interval times in the visible light waveform and the infrared light waveform.

Therefore, the correlation degree computing unit 107 may compute the degree of correlation between the visible light waveform and the infrared light waveform by using the points of inflection present between a crest and a trough of the respective pulse waves acquired by the visible light waveform computing unit 105 and the infrared light waveform computing unit 106. For example, the correlation degree computing unit 107 causes the visible light waveform computing unit 105 and the infrared light waveform computing unit 106 to calculate the first heartbeat interval time and the second heartbeat interval time calculated with the use of the points of inflection and computes the degree of correlation between the first and second heartbeat interval times. As a specific computing method, the degree of correlation is evaluated on the basis of the correlation and/or the absolute error of the heartbeat interval times between the point of inflection in the visible light waveform and the point of inflection in the infrared light waveform.

Although the correlation degree computing unit 107 computes the degree of correlation between the visible light waveform and the infrared light waveform by using the heartbeat interval time between the points of inflection when the correlation coefficient of the heartbeat interval times in the visible light waveform and the infrared light waveform is smaller than the second threshold value or when the number of peak points in the visible light waveform and the infrared light waveform in the first predetermined time period is greater than the first threshold value at least in one of the waveforms, this is not a limiting example. For example, the correlation degree computing unit 107 may compute the degree of correlation between the visible light waveform and the infrared light waveform by using the heartbeat interval time between the points of inflection from the beginning, without using the peak points. Thus, even in a case in which the peak points cannot be acquired from the visible light waveform or the infrared light waveform with high accuracy, the time similar to the heartbeat interval time can be calculated by calculating the heartbeat interval time between the points of inflection. The heartbeat interval time between the points of inflection is less prone to noise as compared to the heartbeat interval time that can be acquired from the peak points, but the point of inflection is more likely to fluctuate between a crest and a trough. In other words, the heartbeat interval time between a crest and another crest is stable, the variance is, for example, within 100 ms, and the time error is likely to be smaller than that of the heartbeat interval time between a point of inflection and another point of inflection. Therefore, in the present disclosure, unless otherwise indicated, the heartbeat interval time computed from the peak points is used preferentially.

In addition, aside from the above, when the following condition is satisfied, the correlation degree computing unit 107 may use the heartbeat interval time between the points of inflection, in place of the heartbeat interval time computed from the peak points, to compute the degree of correlation. The stated condition is, for example, that, of a plurality of heartbeat interval times and another plurality of heartbeat interval times, the variance of the heartbeat interval times corresponding to one of the waveforms of the visible light waveform and the infrared light waveform in which the number of peak points is smaller is no greater than a fourth threshold value (e.g., 100 ms). When a determination as to whether an excess number of peak points have been acquired is made on the basis of the number of the peak points in the first predetermined time period, there is a possibility that a peak point acquired in excess is overlooked because the condition that the number of the peak points in the first predetermined time period exceeds the first threshold value is not satisfied even though there are an excess number of peak points.

Figure 22A:
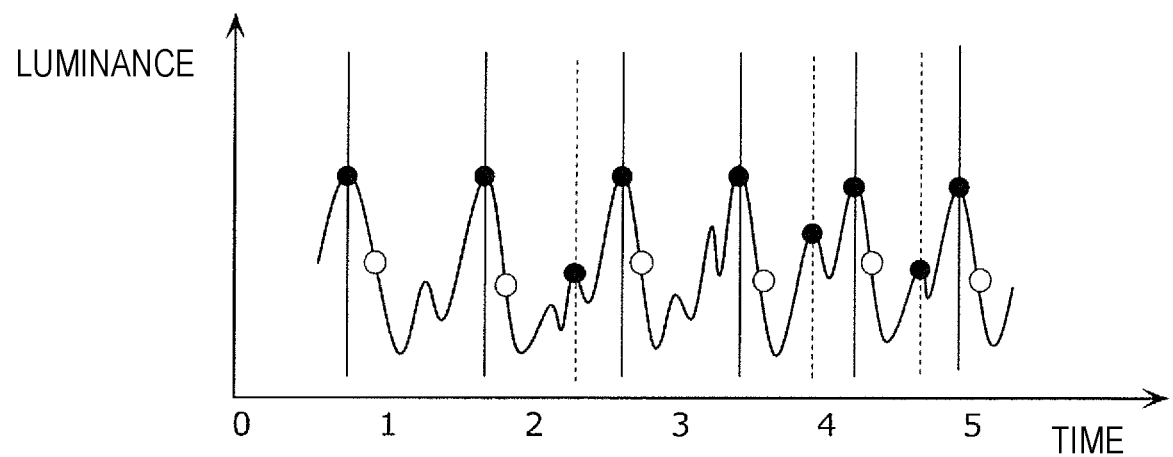
FIGS. 22A and 22B are illustrations for describing an example in which the condition that, even though there are an excess number of peak points, the number of the peak points in a first predetermined time period exceeds a first threshold value is not met.
Figure 22B:
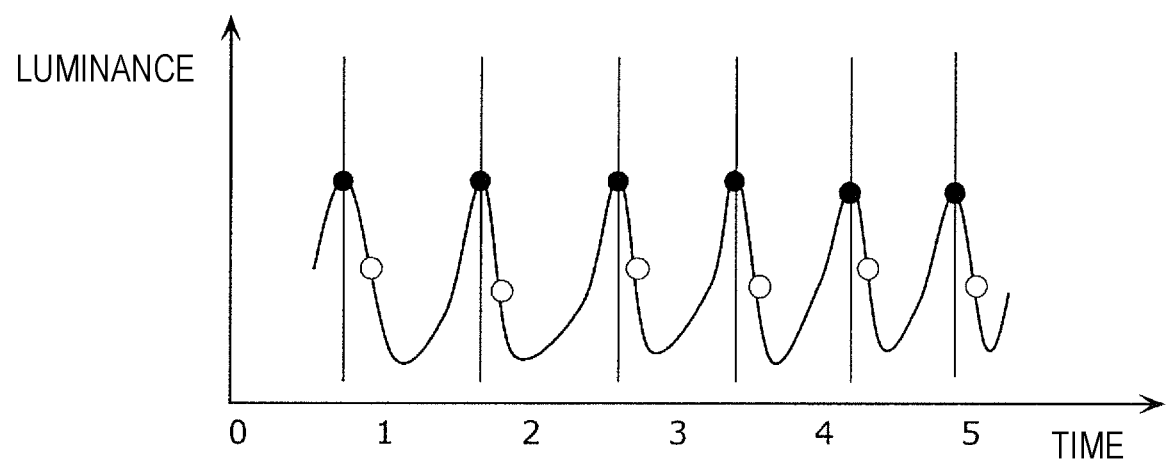

For example, FIGS. 22A and 22B are illustrations for describing an example in which the condition that the number of the peak points in the first predetermined time period exceeds the first threshold value is not met even though there are an excess number of peak points. In both FIG. 22A and FIG. 22B, the horizontal axis represents the time, the vertical axis represents the luminance, the solid circles represent the acquired crests, and the open circles represents the acquired points of inflection.

As illustrated in FIG. 22A, when the number of the peak points acquired in five seconds is eight in the visible light waveform, the condition that the number of the peak points in the first predetermined time period exceeds the first threshold value is not met, but the number of the acquired peak points differs from the number of the peak points acquired in the infrared light waveform illustrated in FIG. 22B. In this case, as described above, if even a single excess peak point is acquired, there arises a problem in that the data numbers of the first heartbeat interval times and the data numbers of the second heartbeat interval times are mismatched by one. Thus, if it is possible to show that the heartbeat interval times in one of the visible light waveform and the infrared light waveform are substantially constant, the peak points can be adjusted (deleted) in accordance with the number of the peak points in that waveform. The details of the adjustment of the peak points are as described with reference to FIG. 20.

When the variance of the heartbeat interval times in the first predetermined time period exceeds the fourth threshold value in both waveforms of the visible light waveform and the infrared light waveform, the correlation degree computing unit 107 determines that an appropriate pulse wave timing cannot be acquired from either waveform and transmits, to the light source controlling unit 108, a "False, Both" signal indicating that an appropriate pulse wave timing cannot be acquired from either waveform.

When the pulse wave measuring apparatus 140 starts being used and when the peak points in the first predetermined time period can be acquired appropriately by the visible light waveform computing unit 105 (i.e., when the variance of the heartbeat interval times is smaller than the fourth threshold value), the correlation degree computing unit 107 stores, into a memory, the result obtained by causing the visible light waveform computing unit 105 to carry out computation with the slope between a crest and a trough of the visible light waveform set as a first slope A. Then, each time the quantity of light of the visible light source 101 or the infrared light source 104 is changed by the light source controlling unit 108, the correlation degree computing unit 107 transmits an instruction to the light source controlling unit 108 so that a second slope between a crest and a trough of the infrared light waveform becomes the first slope A. Furthermore, the correlation degree computing unit 107 does not need to use the peak point acquired while the quantity of light of the light sources are adjusted by the light source controlling unit 108 to compute the degree of correlation between the visible light waveform and the infrared light waveform.

Figure 23:
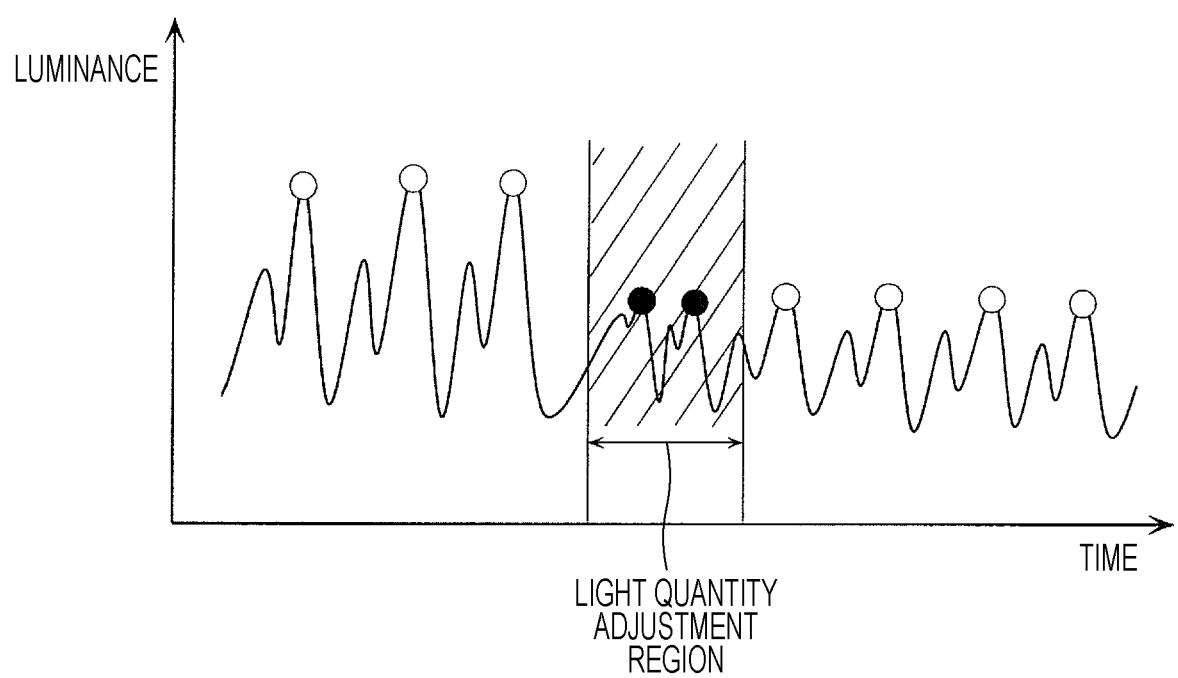
FIG. 23 illustrates an example for describing a case in which a peak point acquired while the quantity of light of a light source is adjusted is not used to compute the degree of correlation between a visible light waveform and an infrared light waveform.

FIG. 23 illustrates an example for describing a case in which a peak point acquired while the quantity of light of the light sources is adjusted is not used to compute the degree of correlation between a visible light waveform and an infrared light waveform. In the graph illustrated in FIG. 23, the horizontal axis represents the time, the vertical axis represents the luminance, and the region with slanted lines indicates that the quantity of light of the light sources is adjusted. In addition, the open circles and the solid circles indicate the acquired peak points.

As illustrated in FIG. 23, as the quantity of light of the light sources is adjusted, the gain of the luminance of the visible light waveform or the infrared light waveform changes, and the kurtosis of the peak point changes in accordance with that change. When the peak point of which the kurtosis has changed is subjected to filtering in the visible light waveform computing unit 105 or the infrared light waveform computing unit 106, the position of the peak point changes along the time axis depending on the kurtosis of the peak of the raw waveform that has not been subjected to filtering. When the heart rate is to be calculated to obtain biometric information, this error does not cause a problem, but an influence of this error is large in a case in which the blood pressure is calculated from the pulse wave transit time or the like. Therefore, in the pulse wave measuring apparatus 140 according to the present disclosure, a predetermined feature point (i.e., a peak point) does not need to be extracted from the visible light waveform or the infrared light waveform acquired while the quantity of light of the visible light source 101 or the infrared light source 104 is controlled through a control signal.

Although the correlation degree computing unit 107 determines that one or both of the waveforms include an excess number of peak points when the correlation coefficient of the heartbeat interval times in the visible light waveform and the infrared light waveform is smaller than the second threshold value, then calculates the error of the heartbeat interval times and/or the variance of the heartbeat interval times, and uses the heartbeat interval time between the points of inflection from a crest to a trough in the waveform when the predetermined condition is satisfied, this is not a limiting example. For example, when the peak points in both waveforms can be acquired appropriately (e.g., the variances of the heartbeat interval times in both waveforms are no greater than the fourth threshold value) even in a case in which the correlation coefficient of the first heartbeat interval times and the second heartbeat interval times is smaller than the second threshold value, the correlation degree computing unit 107 transmits a "False" signal to the light source controlling unit 108.

In this manner, the correlation degree computing unit 107 transmits, to the light source controlling unit 108, a signal (e.g., any one of "True," "False," "False, RGB," "False, IR," and "False, Both") corresponding to the computed degree of correlation and the result of extracting the predetermined feature points from the visible light waveform and the infrared light waveform.

Light Source Controlling Unit 108

The light source controlling unit 108 controls the quantity of light of the visible light and the infrared light emitted by the visible light source 101 and the infrared light source 104, respectively, in accordance with a signal received from the correlation degree computing unit 107.

In addition, when the light source controlling unit 108 receives, for example, a "False, IR" signal, the light source controlling unit 108 can determine that the infrared light waveform computing unit 106 cannot acquire a predetermined feature point in the infrared light waveform appropriately. In other words, for example, the "False, IR" signal indicates that the infrared light waveform contains a large amount of noise. Therefore, the light source controlling unit 108 increases the quantity of light of the infrared light source 104 without adjusting the quantity of the light of the visible light source 101.

In addition, when the light source controlling unit 108 receives a "False, RGB" signal, the light source controlling unit 108 can determine that the visible light waveform computing unit 105 cannot acquire a predetermined feature point in the visible light waveform appropriately. In this case, the light source controlling unit 108 cannot determine whether the infrared light waveform computing unit 106 can acquire a predetermined feature point in the infrared light waveform appropriately. Therefore, the light source controlling unit 108, for example, reduces the quantity of light of the light source in the visible light source 101 if the variance of the heartbeat interval times in the first predetermined time period in the infrared light waveform is no greater than the fourth threshold value and increases the quantity of light of the light source in the infrared light source 104 until the slope from a crest to a trough of the infrared light waveform reaches A. In addition, if the stated variance in the infrared light waveform exceeds the fourth threshold value, the light source controlling unit 108 determines that the signals cannot be acquired in either waveform and changes the signal to a "False, Both" signal.

When the light source controlling unit 108 receives a "False, Both" signal, the light source controlling unit 108 can determine that a predetermined feature point cannot be acquired in either of the visible light waveform and the infrared light waveform. In this case, the light source controlling unit 108 increases the quantity of light of the visible light source 101 until the slope from a crest to a trough in the visible light waveform reaches the first slope A. If the initial quantity of light of the visible light waveform is stored in a memory, the light source controlling unit 108 may increase the quantity of light of the visible light source 101 to reach the initial quantity of light. In addition, the light source controlling unit 108 reduces the quantity of light of the infrared light source 104 to zero. In other words, when a predetermined feature point cannot be acquired in either of the visible light waveform and the infrared light waveform, the light source controlling unit 108 sets the quantity of light of the visible light source 101 and the quantity of light of the infrared light source 104 to the initial states, which are the state in which the predetermined feature point can be acquired most reliably, and readjusts the quantity of light.

In other words, when the variance of the plurality of first heartbeat interval times exceeds the fourth threshold value and the variance of the plurality of second heartbeat interval times also exceeds the fourth threshold value and when the difference between the first heartbeat interval times and the second heartbeat interval times that correspond to each other in time series is smaller than a fifth threshold value ((−1)× the third threshold value), the light source controlling unit 108 reduces the quantity of light of the visible light in the visible light source 101 and increases the quantity of light of the infrared light in the infrared light source 104, and when increasing the quantity of light of the infrared light, increases the quantity of light of the infrared light until the second slope in the infrared light waveform reaches the first slope A stored in the memory.

In addition, when the variance of the plurality of first heartbeat interval times exceeds the fourth threshold value and the variance of the plurality of second heartbeat interval times also exceeds the fourth threshold value and when the difference between the first heartbeat interval times and the second heartbeat interval times that correspond to each other in time series is greater than a sixth threshold value (i.e., the third threshold value), the light source controlling unit 108 increases the quantity of light of the infrared light in the infrared light source 104, and when increasing the quantity of light of the infrared light, increases the quantity of light of the infrared light until the second slope in the infrared light waveform reaches the first slope A stored in the memory.

In addition, when the variance of the plurality of first heartbeat interval times exceeds the fourth threshold value and the variance of the plurality of second heartbeat interval times also exceeds the fourth threshold value and when the difference between the first heartbeat interval times and the second heartbeat interval times that correspond to each other in time series is a value that falls between the fifth threshold value and the sixth threshold value, the light source controlling unit 108 increases the quantity of light of the visible light in the visible light source 101 and reduces the quantity of light of the infrared light in the infrared light source 104.

Although the light source controlling unit 108 increases the quantity of light of the infrared light source 104 until the second slope of the infrared light waveform reaches the first slope A in cases other than the case in which the predetermined feature point cannot be acquired in either of the visible light waveform and the infrared light waveform as indicated by the "False, Both" signal or the like, this is not a limiting example. For example, when the mean luminance value in the ROI exceeds a seventh threshold value, which is 240, for example, the quantity of light of the light source is too large and thus causes an image captured of the skin of the user U to be buried in noise information. Therefore, in this case, it is considered that the second slope of the infrared light waveform exceeds the first slope A, and thus the light source controlling unit 108 may reduce the quantity of light of the infrared light until the second slope falls to the first slope A.

Figure 24:
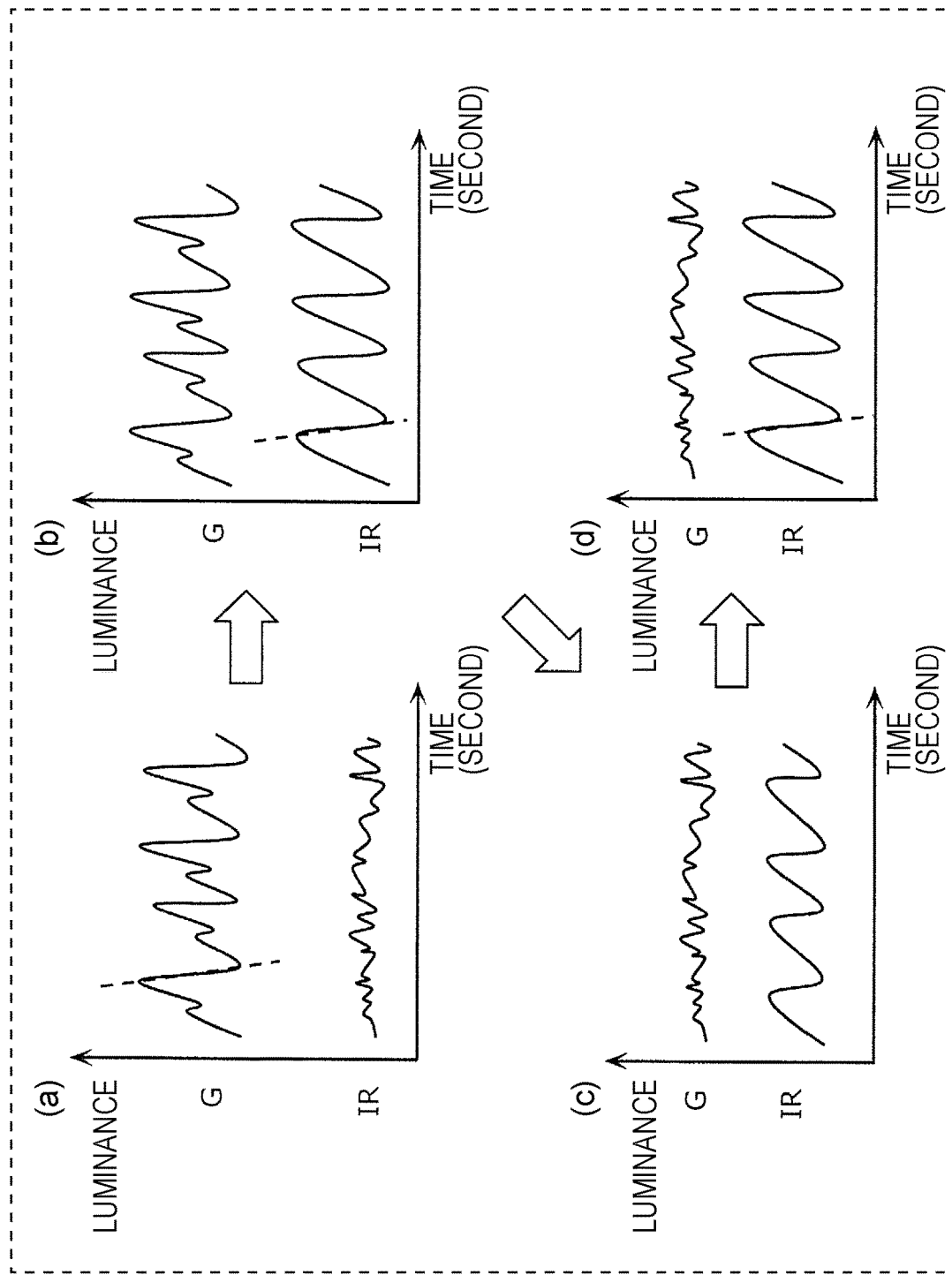
FIG. 24 illustrates an example of the simplest steps for reducing the quantity of light of a visible light source to zero and for increasing the quantity of light of an infrared light source to an appropriate quantity of light by using a pulse wave measuring apparatus.

FIG. 24 illustrates an example of the simplest steps for reducing the quantity of light of the visible light source 101 to zero and for increasing the quantity of light of the infrared light source 104 to an appropriate quantity of light by using the pulse wave measuring apparatus 140. In each of the graphs illustrated in (a) to (d) of FIG. 24, the horizontal axis represents the time, and the vertical axis represents the luminance. In addition, in FIG. 24, the visible light waveform is indicated by RGB, and the infrared light waveform is indicated by IR.

The section (a) of FIG. 24 illustrates a visible light waveform and an infrared light waveform acquired in an initial state in which the user U has turned ON the visible light source 101 with the pulse wave measuring apparatus 140. The visible light waveform illustrated in (a) of FIG. 24 is the waveform in which the slope from a crest to a trough is largest among the visible light waveforms illustrated in (a) to (d) of FIG. 24. Therefore, the slope from the crest to the trough of the visible light waveform at this time is stored into a memory as the first slope A.

In addition, the infrared light source 104 is OFF at this time. Therefore, the infrared light waveform is hardly acquired. In this state, the correlation degree computing unit 107 transmits, for example, a "False, IR" signal to the light source controlling unit 108. Therefore, the light source controlling unit 108 increases the quantity of light of the infrared light in the infrared light source 104. At this point, as the quantity of light of the infrared light source 104 is increased, the infrared light waveform computing unit 106 becomes able to acquire a predetermined feature point of the infrared light waveform and can acquire the second heartbeat interval times. In addition, the variance of the acquired second heartbeat interval times falls within the fourth threshold value. Then, as illustrated in (b) of FIG. 24, while the state in which the variance of the second heartbeat interval times falls within the fourth threshold value is retained, the quantity of light of the infrared light source 104 is increased until the second slope between a crest and a trough of the infrared light waveform reaches the first slope A. When the second slope reaches the first slope A, the correlation degree computing unit 107 transmits, for example, a "TRUE, AMP=A" signal to the light source controlling unit 108. Thus, the light source controlling unit 108 suspends the adjustment of the light sources upon receiving the "TRUE, AMP=A" signal.

Next, the light source controlling unit 108 reduces the quantity of light of the visible light source in the visible light source 101 from that in the state illustrated in (b) of FIG. 24. The section (c) of FIG. 24 illustrates a state in which the variance of the heartbeat interval times is no greater than the fourth threshold value in the infrared light waveform computing unit 106 and the light source in the visible light source 101 is OFF. In addition, (d) of FIG. 24 illustrates a state in which the light source in the visible light source 101 is OFF and the second slope of the infrared light waveform is the first slope A, or in other words, a state that is to be achieved in the end.

In the process of shifting from the state illustrated in (b) of FIG. 24 to the state illustrated in (c) of FIG. 24, the quantity of light of the visible light is reduced at a constant interval of, for example, 1 W. Then, each time the quantity of light of the visible light is reduced, the infrared light waveform computing unit 106 and the correlation degree computing unit 107 check whether a predetermined feature point can be acquired appropriately in the infrared light waveform. In addition, when the infrared light waveform computing unit 106 and the correlation degree computing unit 107 can confirm that the predetermined feature point can be acquired appropriately in the infrared light waveform, as illustrated in (d) of FIG. 24, the quantity of light of the light source in the infrared light source 104 is increased until the second slope of the infrared light waveform reaches the first slope A.

Thus, in the process of shifting from the state illustrated in (b) of FIG. 24 to the state illustrated in (c) of FIG. 24, the correlation degree computing unit 107 transmits a "True" signal or a "False, IR" signal to the light source controlling unit 108, and the light source controlling unit 108 adjusts the quantity of light of the infrared light source 104 each time the light source controlling unit 108 receives a "False, IR" signal until the state becomes "True." Then, when the light source controlling unit 108 receives a "False, RGB" signal from the correlation degree computing unit 107 as the light source controlling unit 108 reduces the quantity of light of the visible light source 101, the light source controlling unit 108 terminates this process.

Alternatively, in the process of shifting from the state illustrated in (c) of FIG. 24 to the state illustrated in (d) of FIG. 24, the correlation degree computing unit 107 transmits a "False, RGB" signal to the light source controlling unit 108, and the light source controlling unit 108 continues to increase the quantity of light of the light source in the infrared light source 104 until the second slope of the infrared light waveform reaches the first slope A and terminates the control of the quantity of light of the light source when, for example, the visible light waveform cannot be acquired and the light source controlling unit 108 receives a "False, RGB, AMP=A" signal indicating that the second slope has reached the first slope A from the correlation degree computing unit 107.

In addition, the light source controlling unit 108 has a feature of carrying out the control of the light sources after two or more consecutive predetermined feature points can be acquired from each of the waveforms of the visible light waveform and the infrared light waveform in the visible light waveform computing unit 105 and the infrared light waveform computing unit 106. In other words, the light source controlling unit 108 refrains from outputting a control signal for controlling the quantity of light of the visible light in the visible light source 101 or outputting a control signal for controlling the quantity of light of the infrared light in the infrared light source 104 until two or more consecutive predetermined feature points are extracted within a second predetermined time period from each of the waveforms of the visible light waveform and the infrared light waveform.

Figure 25:
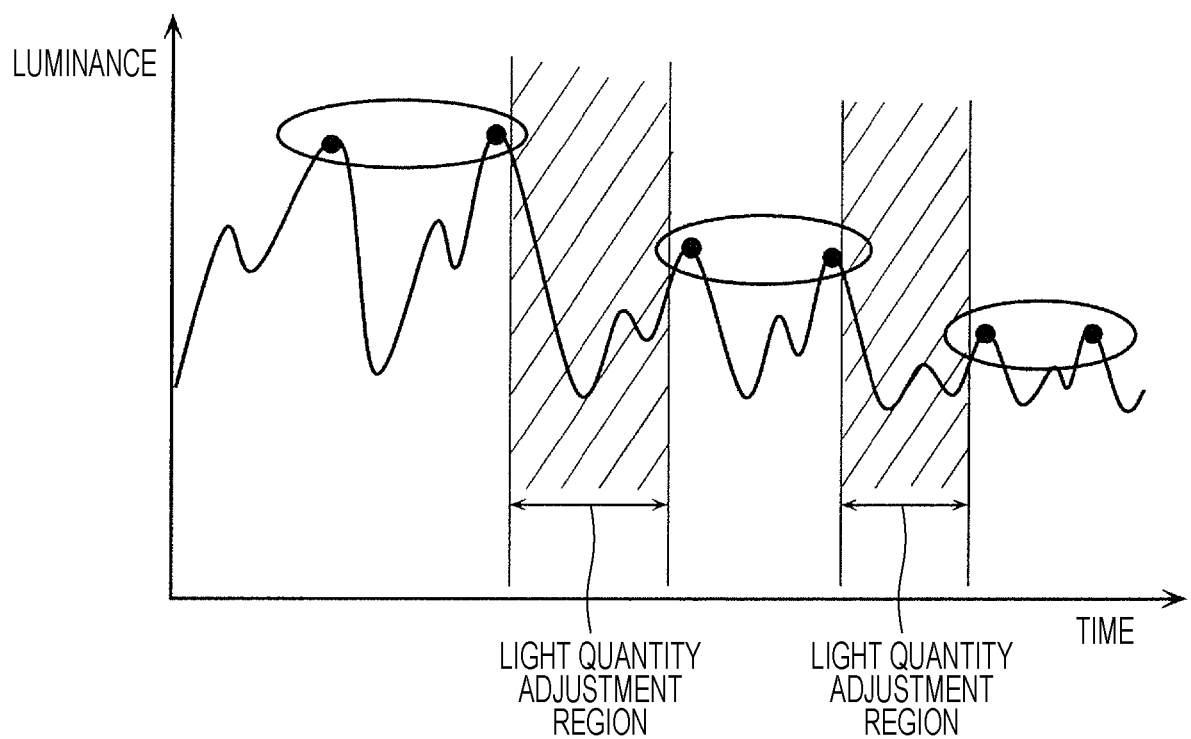
FIG. 25 is an illustration for describing a case in which light source control is put on hold until two or more consecutive predetermined feature points are extracted from each of a visible light waveform and an infrared light waveform within a second predetermined time period.

FIG. 25 is an illustration for describing a feature that the light source control is put on hold until two or more consecutive predetermined feature points are extracted within the second predetermined time period from each of the waveforms of the visible light waveform and the infrared light waveform. The graph illustrated in FIG. 25 presents the visible light waveform or the infrared light waveform. In the graph illustrated in FIG. 25, the horizontal axis represents the time, and the vertical axis represents the luminance.

When the light source controlling unit 108 changes the quantity of light of the visible light source 101 or the infrared light source 104, the gain of the luminance of the visible light waveform or the infrared light waveform changes. Then, when the gain of the luminance changes, the position of the pulse wave timing shifts, and thus a large error is produced in calculating the timing such as the heartbeat interval time. In the present disclosure, the heartbeat interval time is primarily used as a material for determining the degree of correlation between the visible light waveform and the infrared light waveform, and two consecutive peak points are necessary for calculating the heartbeat interval time. Therefore, as illustrated in FIG. 25, the light source controlling unit 108 adjusts the quantity of the light source after confirming that two or more consecutive peak points have been obtained in the visible light waveform or the infrared light waveform.

Biometric Information Calculating Unit 109

The biometric information calculating unit 109 calculates the biometric information of the user U by using either one of the feature amount of the visible light waveform acquired by the visible light waveform computing unit 105 and the feature amount of the infrared light waveform acquired by the infrared light waveform computing unit 106. Specifically, the biometric information calculating unit 109 acquires the first heartbeat interval time from the visible light waveform computing unit 105 when the visible light source 101 is ON and when the visible light waveform can be acquired in the visible light waveform computing unit 105. Then, the biometric information calculating unit 109 calculates the biometric information, such as the heart rate and the stress index, for example, by using the first heartbeat interval time.

Meanwhile, the biometric information calculating unit 109 acquires the second heartbeat interval time from the infrared light waveform computing unit 106 when the visible light source 101 is OFF or the visible light waveform cannot be acquired by the visible light waveform computing unit 105 and when the infrared light waveform can be acquired by the infrared light waveform computing unit 106. Then, in a similar manner, the biometric information calculating unit 109 calculates the biometric information, such as the heart rate and the stress index, for example, by using the second heartbeat interval time.

The biometric information calculating unit 109 calculates the biometric information by using the first heartbeat interval time from the visible light waveform computing unit 105 when the feature amounts (heartbeat interval times) of the waveforms (the visible light waveform and the infrared light waveform) can be extracted in both the visible light waveform computing unit 105 and the infrared light waveform computing unit 106. This is because the visible light exhibits higher robustness to noise caused by body movement or the like and is more reliable than the infrared light.

Although the biometric information to be calculated includes the heart rate and the stress index, these are not limiting examples. For example, the acceleration pulse wave may be calculated from the obtained pulse wave, and the arteriosclerosis index may be calculated. In addition, the pulse wave timings may be acquired accurately from two different sites on the user U, and the blood pressure may be estimated from the time difference therebetween (pulse wave transit time). In addition, the predominance of sympathetic nerve or parasympathetic nerve may be calculated from the variation in the heartbeat interval time, and the sleepiness of the user U may be calculated.

Information Presentation Unit 110

The information presentation unit 110 presents a face image of the user U captured by the visible light imaging unit 102 and presents an instruction to the user U so that the face of the user U can be captured by the visible light imaging unit 102. In addition, the information presentation unit 110 presents the biometric information obtained from the biometric information calculating unit 109. Specifically, the information presentation unit 110 displays, on the display screen, the heart rate, the stress index, or the sleepiness information of the user U or the like obtained from the biometric information calculating unit 109. The display screen on which the information presentation unit 110 presents the stated information may be a dedicated display screen provided for the pulse wave measuring apparatus 140, or the display screen of the car navigation device may also serve as the stated display screen. When the display screen of the car navigation device is also used as the display screen of the information presentation unit 110, the pulse wave measuring apparatus 140 includes a transmitting unit (not illustrated) that transmits the information to be displayed to the car navigation device. When the display screen of the car navigation device is also used as the display screen of the information presentation unit 110, as described above, there is an advantage in that this display screen can further function as the visible light source 101.

In addition, the information presentation unit 110 may present the information to a mobile terminal of the user U by communicating with the mobile terminal of the user U. The pulse wave measuring apparatus 140 may include an information storing unit (not illustrated) to record and accumulate the obtained biometric information therein, and the user U may be able to check the biometric information obtained during sleep and/or before and after sleep at a later time.

Although the information presentation unit 110 presents the biometric information obtained from the biometric information calculating unit 109, this is not a limiting example. For example, the information presentation unit 110 may continuously present the quantity of light of the light emitted by the visible light source 101 or the quantity of light of the light emitted by the infrared light source 104. In addition, the information presentation unit 110 may present the degree of match at a present moment obtained from the correlation degree computing unit 107 in percentage as the reliability, for example. Specifically, the information presentation unit 110 may present the correlation coefficient between the visible light waveform and the infrared light waveform.

Figure 26:
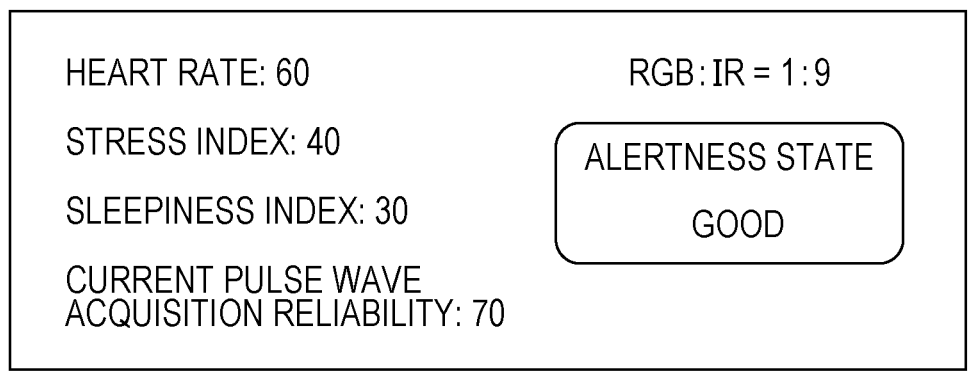
FIG. 26 illustrates a display example on a presentation device.

FIG. 26 illustrates a display example on the information presentation unit 110. In FIG. 26, the information presentation unit 110 displays the heart rate, the stress index, and the sleepiness index of the user U, the current pulse wave acquisition reliability (the reliability of the pulse wave acquired currently), the ratio of the quantity of light of the visible light source 101 and the quantity of light of the infrared light source 104, and the alertness state of the user U. Here, the current pulse wave acquisition reliability indicates the correlation coefficient in the degree of match between the heartbeat interval times in the visible light pulse wave and the heartbeat interval times in the infrared light pulse wave. In addition, the ratio of the quantity of light of the visible light source 101 and the quantity of light of the infrared light source 104 is the ratio of the intensity of the quantity of light of the visible light source 101 and the intensity of the quantity of light of the infrared light source 104 at a present moment. The alertness state of the user U is the alertness state in the driving of the user U determined from each piece of the information described above. For example, the alertness state is considered to be "GOOD" when the heart rate is no higher than 65, the stress index is no higher than 40, and the sleepiness index is no higher than 40. These contents may be displayed and may additionally be provided through sounds or the like, for example. In addition, when the alertness index of the user U decreases, the user U may be warned with an alarm sound or the like. This is because, since the user U is driving the vehicle, it is more appropriate to provide the information in the form of sounds or the like than in the form of visual data.

Figure 27:
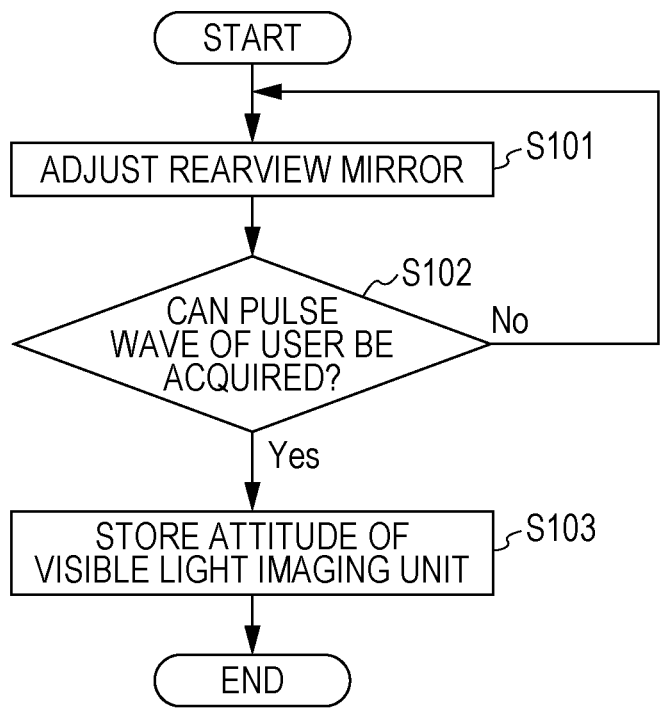
FIG. 27 is a flowchart illustrating a processing flow for an initial setting of a pulse wave measuring apparatus according to an embodiment.

FIG. 27 is a flowchart illustrating a processing flow for the initial setting of the pulse wave measuring apparatus 140 according to the present embodiment.

In step S101, the user U adjusts the rearview mirror M in order to ensure the rearward field of view via the rearview mirror M. This adjustment is an action taken by the user U in order to drive the vehicle appropriately regardless of whether the pulse wave measuring apparatus 140 is installed in the vehicle.

In step S102, it is determined whether the pulse wave of the user U can be acquired in the visible light imaging unit 102 or the infrared light imaging unit 103. If it is determined that the pulse wave of the user U can be acquired, the processing proceeds to step S103. If it is determined that the pulse wave cannot be acquired, the processing returns to step S101 (readjustment of the rearview mirror M).

In step S103, the pulse wave measuring apparatus 140 stores the attitude of the visible light imaging unit 102. Specifically, the attitude of the visible light imaging unit 102 is defined by the orientation of the visible light imaging unit 102 in the up and down direction and the orientation thereof in the right and left direction. This step is for reducing the adjustment amount when the same user is on board the vehicle next time.

Figure 28:
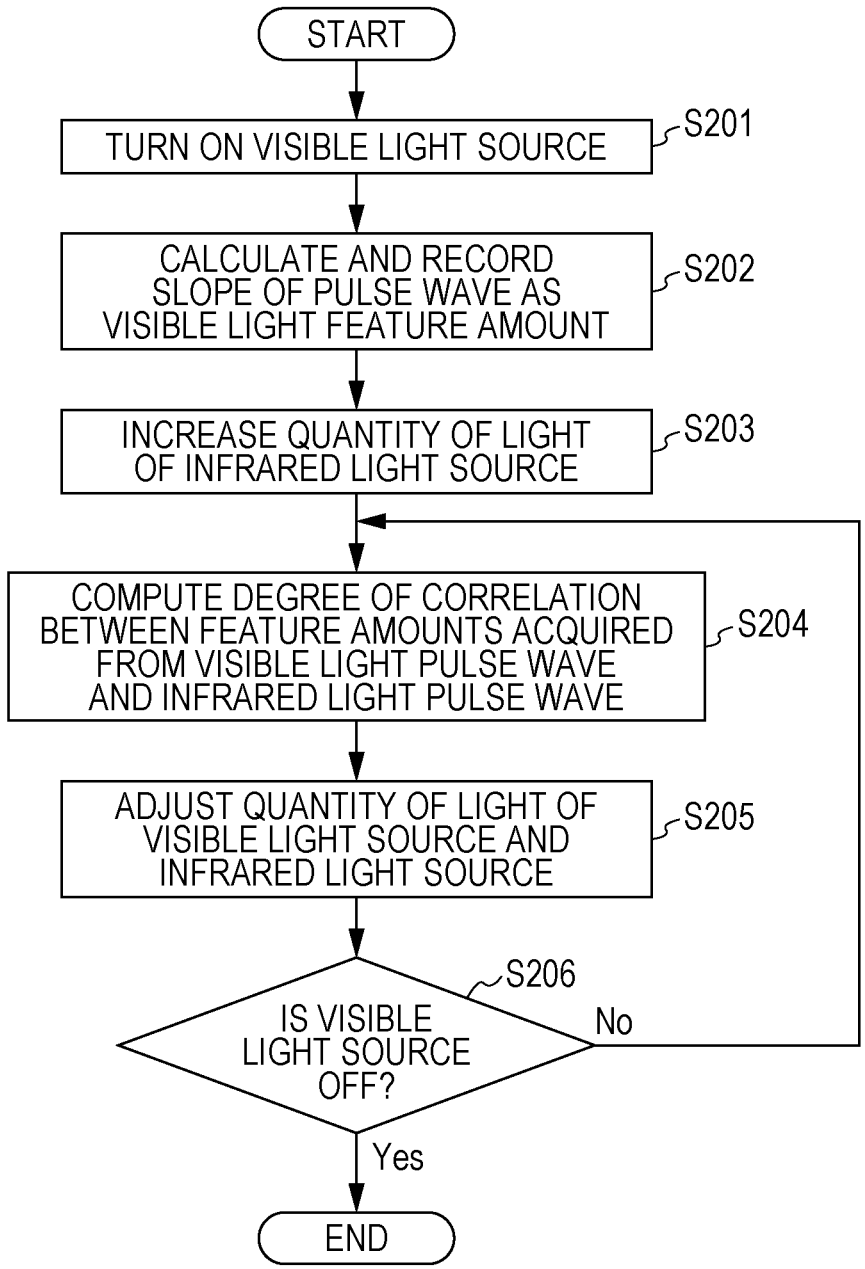
FIG. 28 is a flowchart illustrating a processing flow of a pulse wave measuring apparatus according to an embodiment.

FIG. 28 is a flowchart illustrating a processing flow of the pulse wave measuring apparatus 140 according to the present embodiment.

In step S201, the visible light source 101 is started upon the user U getting on board the vehicle, upon the rearview mirror M being adjusted, or upon the user U carrying out an explicit ON operation.

In step S202, the visible light imaging unit 102 captures a skin image of the face, a hand, or the like of the user U, and the visible light waveform computing unit 105 calculates and records the slope between a peak and a bottom of the visible light pulse wave.

In step S203, the infrared light source 104 increases the quantity of infrared light to be emitted on the basis of the control by the light source controlling unit 108.

In step S204, the correlation degree computing unit 107 computes the degree of correlation of the feature amounts, such as the heartbeat interval times, acquired by the visible light waveform computing unit 105 and the infrared light waveform computing unit 106.

In step S205, the light source controlling unit 108 adjusts the quantity of light of the visible light emitted by the visible light source 101 and the quantity of light of the infrared light emitted by the infrared light source 104 on the basis of the degree of correlation obtained in step S204 and the pulse wave peak acquisition rate.

In step S206, it is determined whether the power source of the visible light source 101 is OFF. If it is determined that the power source of the visible light source 101 is OFF (Yes in step S206), the processing is terminated. Meanwhile, if it is determined that the power source of the visible light source 101 is not OFF (i.e., the power source is ON) (No in step S206), the processing returns to step S204.

The pulse wave measuring apparatus 140 described thus far is for measuring the pulse wave of a user appropriately by using a visible light pulse wave and an infrared light pulse wave. In the present disclosure, not all the constituent elements of the pulse wave measuring apparatus 140 are essential, and the effect can be obtained with some of the constituent elements. A minimum configuration that provides the effect in the present disclosure will be described hereinafter through modifications.

Modifications of Embodiments

In the present modification, essential constituent elements of the pulse wave measuring apparatus according to the embodiment described above will be illustrated.

Figure 29:
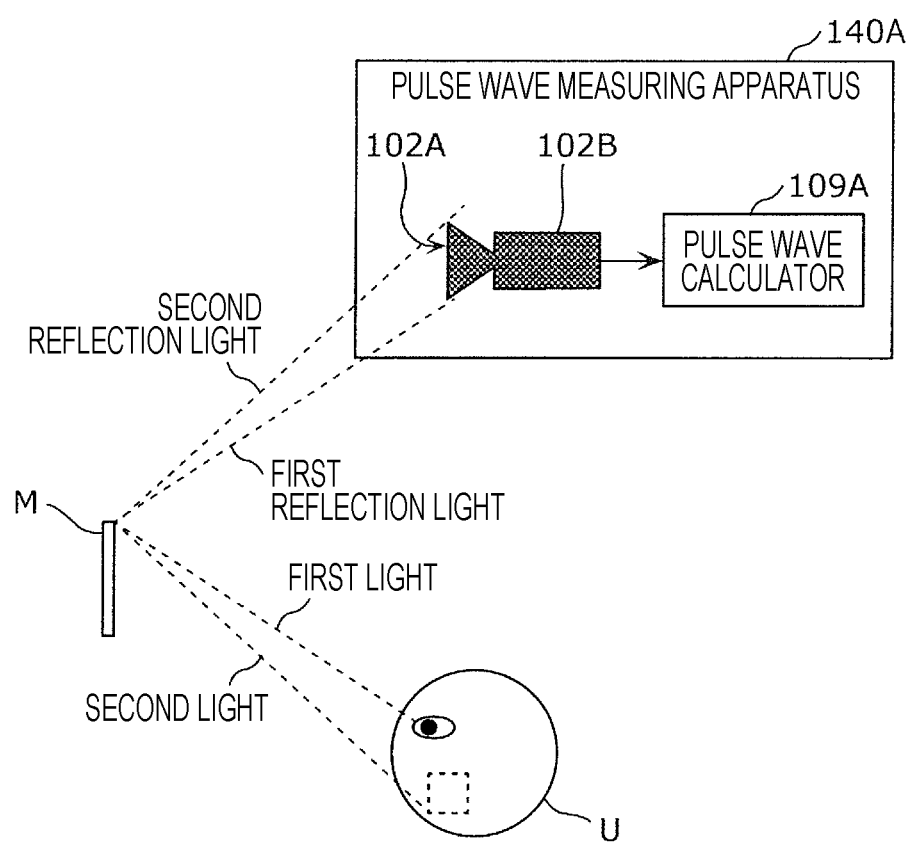
FIG. 29 is a block diagram illustrating a configuration of a pulse wave measuring apparatus according to a modification of an embodiment.

FIG. 29 is a block diagram illustrating a configuration of a pulse wave measuring apparatus 140A according to the present modification.

As illustrated in FIG. 29, the pulse wave measuring apparatus 140A includes a visible light receiver 102B and a pulse wave calculator 109A. When a vehicle provided with the visible light receiver 1026 is viewed from a side, a first surface (i.e., a surface 102A) is located in a first region between a first optical path of first reflection light and a second optical path of second reflection light. First light comes from an eye of a user sitting on a seat of the vehicle, and second light comes from a cheek of the user. An upper end of an interior front mirror (i.e., a rearview mirror M) of the vehicle reflects the first light to produce the first reflection light. The stated upper end reflects the second light to produce the second reflection light. The pulse wave calculator 109A calculates a pulse wave of the user on the basis of a waveform of visible light received by the visible light receiver 102B via the first surface and outputs the calculated pulse wave.

The visible light receiver 1026 corresponds to the visible light imaging unit 102 according to the embodiment. In addition, the pulse wave calculator 109A corresponds to the visible light waveform computing unit 105 and the biometric information calculating unit 109 according to the embodiment. As the pulse wave measuring apparatus 140A is configured as described above, the pulse wave can be measured by capturing an image of the user with a simpler configuration.

As described thus far, with the pulse wave measuring apparatus according to the present embodiment, the visible light receiver can acquire an image of the user via the rearview mirror, and the user does not visually recognize the visible light receiver. Thus, the user can drive without being distracted by a camera constituted by the visible light receiver, and the pulse wave measuring apparatus can acquire the pulse wave of the user while driving. Here, the rearview mirror is typically adjusted by the user for driving (specifically, in order to ensure the rearward field of view or the like). Thus, the user does not need to adjust the attitude of the rearview mirror in order to acquire the pulse wave. In addition, the rearview mirror is a typical rearview mirror mounted in a vehicle and is not a rearview mirror providing any special performance or function exceeding that of a typical rearview mirror. In this manner, the pulse wave measuring apparatus can measure the pulse wave by capturing an image of the user with a simpler configuration.

In addition, in a similar manner to the visible light receiver, an infrared light receiver can acquire an image of the user via the rearview mirror, and the user does not visually recognize the infrared light receiver. Thus, the user can drive without being distracted by a camera constituted by the infrared light receiver, and the pulse wave measuring apparatus can acquire the pulse wave of the user while driving.

In addition, the feature that the visible light receiver can acquire an image of a cheek of the user via the rearview mirror and the user does not visually recognize the visible light receiver is achieved specifically by the position of the visible light receiver as the vehicle is viewed from a side.

In addition, the feature that the infrared light receiver can acquire an image of a cheek of the user via the rearview mirror and the user does not visually recognize the infrared light receiver is achieved specifically by the position of the infrared light receiver as the vehicle is viewed from a side.

According to the above aspect, the feature that the visible light receiver can acquire an image of a cheek of the user via the rearview mirror and the user does not visually recognize the visible light receiver is achieved specifically by the position of the visible light receiver as the vehicle is viewed from the above.

According to the above aspect, the feature that the infrared light receiver can acquire an image of a cheek of the user via the rearview mirror and the user does not visually recognize the infrared light receiver is achieved specifically by the position of the infrared light receiver as the vehicle is viewed from the above.

In addition, the pulse wave measuring apparatus can irradiate, of the face of the user, a region suitable for measuring the pulse wave of the user with irradiation light (infrared light) for capturing an image of the user with infrared light by the infrared light receiver. The region suitable for measuring the pulse wave of the user is a region that includes, for example, a cheek within the face of the user. In addition, typically, a controller or the like for a car navigation device or for an air conditioner is disposed at the center of the vehicle in the right and left direction. Thus, there is an advantage in that it is relatively easy to add the infrared light source to such devices or to dispose the infrared light source in the vicinity of such devices. Another reason is that the signal wires and the electric power wires of the vehicle are integrated.

In addition, the feature that the visible light receiver can acquire an image of a cheek of the user via the rearview mirror and the user does not visually recognize the visible light receiver can be achieved specifically. In particular, the position in an optical path of light coming from an eye of the user and reflected by the upper end portion of the rearview mirror is the position on which the user can place a mark by checking the rearview mirror. Thus, there is an advantageous effect that the user can determine the position of the visible light receiver with ease.

In addition, even in a case in which the user wears eyeglasses, the pulse wave of the user can be measured appropriately. When the user wears eyeglasses, the frame of the eyeglasses may overlap the cheeks in the image for measuring the pulse wave, but the above-described configuration prevents such an overlap.

Each of the constituent elements included in the pulse wave measuring apparatus and so on may be a circuit. These circuits may constitute a single circuit as a whole or may each be configured as a separate circuit. In addition, these circuits may each be a general purpose circuit or a dedicated circuit. In other words, in each of the above embodiments, each constituent element may be constituted by a dedicated hardware piece or may be implemented by executing a software program suitable for each constituent element.

In addition, each constituent element may be implemented as a program executing unit, such as a CPU or a processor, reads out a software program recorded on a recording medium, such as a hard disk or a semiconductor memory, and executes the software program. Here, software that implements the pulse wave measuring method and so on of each of the embodiments described above is a program such as the one described below.

Specifically, this program causes a computer to execute a pulse wave measuring method that includes a visible light receiving step of receiving visible light with a visible light receiver provided in a region including a region in an optical path of light coming from a user and reflected by a rearview mirror of a vehicle and excluding a region that the user can see via the rearview mirror and a pulse wave calculating step of calculating a pulse wave of the user on the basis of a waveform of the visible light received in the visible light receiving step and outputting the calculated pulse wave.

Thus far, a pulse wave measuring apparatus and so on according to one or a plurality of aspects have been described on the basis of the embodiments, but the present disclosure is not limited to these embodiments. Unless departing from the spirit of the present disclosure, an embodiment obtained by making various modifications that are conceivable by a person skilled in the art to the present embodiments or an embodiment obtained by combining constituent elements in different embodiments may also be included within the scope of one or a plurality of aspects.

For example, in the embodiments described above, processing executed by a specific constituent element may be executed by another constituent element in place of the specific constituent element. In addition, the order of the plurality of processes may be modified, or a plurality of processes may be executed in parallel.

The present disclosure is effectively used in a pulse wave measuring apparatus or the like that contactlessly acquires the pulse wave of a user inside a vehicle.

What is claimed is:

1. A The pulse wave measuring method comprising:
    (a) positioning a first surface of a visible light receiver in a first region in an interior of a vehicle, the first region being located between a first optical path of a first ray and a second optical path of a second ray included in reflection light from an interior front mirror of the vehicle in response to incident light on the interior front mirror, the incident light including first light and second light, the first light coming from a direction where an eye of a user is located, the second light coming from a direction where a cheek of the user is located, the first light including a third ray and the second light including a fourth ray, the eye and the cheek being a right eye and a right cheek of the user when the user is sitting at a left-hand steering wheel of the vehicle and facing toward a front of the vehicle, and the eye and the cheek being a left eye and a left cheek of the user when the user is sitting at a right-hand steering wheel and facing toward the front of the vehicle, wherein the first optical path and the second optical path are defined with the vehicle being viewed from a side of the vehicle;
    (b) positioning a second surface of an infrared light receiver in the first region in the interior of the vehicle;
    (c) receiving, with the visible light receiver, visible light via the first surface;
    (d) receiving, with the infrared light receiver, a waveform of infrared light via the second surface; and
    (e) calculating, with a processor, a pulse wave of the user on the basis of a waveform of the received visible light and the waveform of the received infrared light and outputting the calculated pulse wave.

2. A The pulse wave measuring method comprising:
    (a) positioning a first surface of a visible light receiver in a first region in an interior of a vehicle, the first region being located between a first optical path of a first ray and a second optical path of a second ray included in reflection light from an interior front mirror of the vehicle in response to incident light on the interior front mirror, the incident light including first light and second light, the first light coming from a direction where an eye of a user is located, the second light coming from a direction where a cheek of the user is located, the first light including a third ray and the second light including a fourth ray, the eye and the cheek being a right eye and a right cheek of the user when the user is sitting at a left-hand steering wheel of the vehicle and facing toward a front of the vehicle, and the eye and the cheek being a left eye and a left cheek of the user when the user is sitting at a right-hand steering wheel and facing toward the front of the vehicle, wherein the first optical path and the second optical path are defined with the vehicle being viewed from a side of the vehicle;

(b) receiving, with the visible light receiver, visible light via the first surface;

(c) calculating, with a processor, a pulse wave of the user on the basis of a waveform of the received visible light and outputting the calculated pulse wave; and (d) positioning an infrared light source in the interior of the vehicle at a position closer to a center of the vehicle in a lateral direction than a seat on which the user sits.

3. A The pulse wave measuring method comprising:

(a) positioning a first surface of a visible light receiver in a first region in an interior of a vehicle, the first region being located between a first optical path of a first ray and a second optical path of a second ray included in reflection light from an interior front mirror of the vehicle in response to incident light on the interior front mirror, the incident light including first light and second light, the first light coming from a direction where an eye of a user is located, the second light coming from a direction where a cheek of the user is located, the first light including a third ray and the second light including a fourth ray, the eye and the cheek being a right eye and a right cheek of the user when the user is sitting at a left-hand steering wheel of the vehicle and facing toward a front of the vehicle, and the eye and the cheek being a left eye and a left cheek of the user when the user is sitting at a right-hand steering wheel and facing toward the front of the vehicle, wherein the first optical path and the second optical path are defined with the vehicle being viewed from a side of the vehicle;

(b) receiving, with the visible light receiver, visible light via the first surface; and (c) calculating, with a processor, a pulse wave of the user on the basis of a waveform of the received visible light and outputting the calculated pulse wave, wherein the positioning of the first surface of the visible light receiver comprises positioning the first surface above the first optical path and toward the front of the vehicle by a first distance with the vehicle being viewed from the side of the vehicle.

4. A The pulse wave measuring method comprising:

(a) positioning a first surface of a visible light receiver in a first region in an interior of a vehicle, the first region being located between a first optical path of a first ray and a second optical path of a second ray included in reflection light from an interior front mirror of the vehicle in response to incident light on the interior front mirror, the incident light including first light and second light, the first light coming from a direction where an eye of a user is located, the second light coming from a direction where a cheek of the user is located, the first light including a third ray and the second light including a fourth ray, the eye and the cheek being a right eye and a right cheek of the user when the user is sitting at a left-hand steering wheel of the vehicle and facing toward a front of the vehicle, and the eye and the cheek being a left eye and a left cheek of the user when the user is sitting at a right-hand steering wheel and facing toward the front of the vehicle, wherein the first optical path and the second optical path are defined with the vehicle being viewed from a side of the vehicle;

(b) receiving, with the visible light receiver, visible light via the first surface; and (c) calculating, with a processor, a pulse wave of the user on the basis of a waveform of the received visible light and outputting the calculated pulse wave, wherein the first ray and the second ray come from an upper end of the interior front mirror of the vehicle, the third ray and the fourth ray reach the upper end of the interior front mirror of the vehicle, and the upper end of the interior front mirror is defined with the vehicle being viewed from the side of the vehicle.

* * * * *